US009090874B2

(12) United States Patent
Roisen et al.

(10) Patent No.: US 9,090,874 B2
(45) Date of Patent: Jul. 28, 2015

(54) OLFACTORY EPITHELIAL-DERIVED STEM CELLS AND METHODS OF USE THEREFOR

(75) Inventors: Fred J. Roisen, Prospect, KY (US);
Chengliang Lu, Louisville, KY (US);
Meng Wang, Louisville, KY (US);
Mengsheng Qiu, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 86 days.

(21) Appl. No.: 13/127,142

(22) PCT Filed: Nov. 2, 2009

(86) PCT No.: PCT/US2009/062962
§ 371 (c)(1),
(2), (4) Date: Jul. 27, 2011

(87) PCT Pub. No.: WO2010/051531
PCT Pub. Date: May 6, 2010

(65) Prior Publication Data
US 2011/0280846 A1 Nov. 17, 2011

Related U.S. Application Data

(60) Provisional application No. 61/278,840, filed on Oct. 13, 2009, provisional application No. 61/197,896, filed on Oct. 31, 2008.

(51) Int. Cl.
C12N 5/0793 (2010.01)
A61K 35/12 (2015.01)

(52) U.S. Cl.
CPC .............. C12N 5/0619 (2013.01); A61K 35/12 (2013.01); C12N 2501/01 (2013.01); C12N 2501/38 (2013.01); C12N 2501/385 (2013.01); C12N 2501/41 (2013.01); C12N 2501/60 (2013.01); C12N 2510/00 (2013.01)

(58) Field of Classification Search
None
See application file for complete search history.

(56) References Cited

U.S. PATENT DOCUMENTS

| 5,648,235 | A | 7/1997 | Zurr et al. |
| 5,660,827 | A | 8/1997 | Thorpe et al. |
| 5,733,876 | A | 3/1998 | O'Reilly et al. |
| 5,753,230 | A | 5/1998 | Brooks et al. |
| 5,762,918 | A | 6/1998 | Thorpe |
| 5,766,591 | A | 6/1998 | Brooks et al. |
| 5,776,427 | A | 7/1998 | Thorpe et al. |
| 2004/0214324 | A1 | 10/2004 | Isacson et al. |
| 2004/0235096 | A1 | 11/2004 | Perlmann et al. |
| 2006/0171935 | A1 | 8/2006 | Abeliovich et al. |
| 2006/0233771 | A1 | 10/2006 | Arenas et al. |
| 2006/0275744 | A1 | 12/2006 | Abeliovich et al. |

FOREIGN PATENT DOCUMENTS

| WO | WO 01/53461 | 7/2001 |
| WO | WO03/064601 | 8/2003 |
| WO | WO 2004/029229 | 4/2004 |
| WO | WO2008/027848 | 3/2008 |

OTHER PUBLICATIONS

Fawcett et al. (1999) The glial scar and central nervous system repair. Brain Research Bulletin 49(6): 377-391.*
Rossi and Cattaneo (2002) Neural stem cell therapy for neurological diseases: dreams and reality. Nature Reviews Neuroscience 3: 401-409.*
Stem Cells: Scientific Progress and Future Research Directions. Chapter 2, pp. 5-10. Department of Health and Human Services. Jun. 2001. http://www.nih.gov/news/stemcell/scireport.htm.*
Zhang et al. (2006) Induction of neuronal differentiation of adult human olfactory neuroepithelial-derived progenitors. Brain Research 1073-1074: 109-119.*
Kim et al. Neuopathology 33:491-504, 2013.*
Zhang et al., "Role of transcription factors in motoneuron differentiation of adult human olfactory neuroepithelial-derived progenitors," *Stem Cells*, Feb. 2006, 24(2):434-442.
Supplementary European Search Report, App. No. EP 09 82 4217, completed Nov. 11, 2011, 7 pages.
Anderson and Caldwell. "Human neural progenitor cell transplants into the subthalamic nucleus lead to functional recovery in a rat model of Parkinson's disease," *Neurobiol Dis.*, 2007, 27:133-140.
Andersson et al.. Identification of Intrinsic Determinants of Midbrain Dopamine Neurons, *Cell*, Jan. 27, 2006, vol. 124, No. 2, pp. 393-405.
Blesch et al. "Neurotrophic factors, gene therapy, and neural stem cells for spinal cord repair," *Brain Research Bulletin*, Apr. 2002, vol. 57, No. 6, pp. 833-838.
Borlongan, "Transplantation therapy for Parkinson's disease," *Expert.Opin.Investig.Drugs*, 2000, 9:2319-2330.
Brederlau et al., "Transplantation of human embryonic stem cell-derived cells to a rat model of Parkinson's disease: effect of in vitro differentiation on graft survival and teratoma formation," *Stem Cells*, 2006, 24:1433-1440.
Carter, "Site-directed mutagenesis," *Biochem J.*, 1986,237:1-7.
Daadi, "Activation and Differentiation of Endogenous Neural Stem Cell Progeny in the Rat Parkinson Animal Model," *Methods Mol Biol.*, 2002, 198:265-271.
Deumens et al., "Modeling Parkinson's disease in rats: an evaluation of 6-OHDA lesions of the nigrostriatal pathway," *Exp Neurol.*, 2002, 175:303-317.

(Continued)

Primary Examiner — Marcia S Noble
(74) Attorney, Agent, or Firm — Fish & Richardson P.C.

(57) ABSTRACT

The presently disclosed subject matter provides recombinant dopaminergic neurons and/or recombinant progenitors thereof that include one or more transgenes encoding a nurr-1 polypeptide, a pitx3 polypeptide, an Imxi a polypeptide, a biologically active fragment thereof, a biologically active derivative thereof, and/or any combination thereof. Also provided are methods for producing a recombinant dopaminergic neuron or recombinant progenitor thereof, methods for producing lineage primed cells, methods for ameliorating at least one symptom associated with a neurological disorder, methods for transplantation, methods for inducing growth, repair, ancllor regeneration of a neuron, for delivering a cytokine or a growth factor to the central nervous system, methods for providing a dopaminergic neuron function, and cell cultures that include recombinant olfactory epithelial-derived stem cells and/or a differentiated derivatives thereof.

12 Claims, 14 Drawing Sheets

(56) References Cited

OTHER PUBLICATIONS

Doss et al., "Embryonic stem cells: a promising tool for cell replacement therapy," *J Cell Mol Med.*, 2004, 8:465-473.
Dubois et al. "Monoclonal antibody A2B5, which detects cell surface antigens, binds to ganglioside $GT_3$ ($II^3$ $(NeuAc)_3LacCer$) and to its 9-O-acetylated derivative," *J Biol Chem.*, 1990, 265:2797-2803.
Freed et al., "Transplantation of Embryonic Dopamine Neurons for Severe Parkinson's Disease," *N Engl J Med.*, 2001, 344:710-719.
Freeman et al., "Bilateral fetal nigral transplantation into the postcommissural putamen in Parkinson's disease," *Ann Neurol.*, 1995, 38:379-388.
Hornykiewicz, "Dopamine in the Basal Ganglia: Its Role and Therapeutic Implications (Including the Clinical Use of L-DOPA)," *Br Med Bull.*, 1973, 29:172-178.
Hornykiewicz, "Parkinson's disease: from brain homogenate to treatment," *Fed Proc.*, 1973, 32:183-190.
Iancu et al., "Behavioral characterization of a unilateral 6-OHDA-lesion model of Parkinson's disease in mice," *Behav Brain Res.*, 2005, 162:1-10.
Lang & Lozano, "Parkinson's Disease. First of Two Parts," *N Engl J Med.*, 1998, 339:1044-1053.
Li et al., "Repair of adult rat corticospinal tract by transplants of olfactory ensheathing cells," *Science*, 1997, 277:2000-2002.
Lindvall et al., "Fetal dopamine-rich mesencephalic grafts in Parkinson's disease," *Lancet*, 1988, 2:1483-1484.
Lindvall et al., "Stem cell therapy for human neurodegenerative disorders—how to make it work," *Nat Med.*, 2004, 10 Suppl:S42-S50.
Lindvall et al., "Transplantation of fetal dopamine neurons in Parkinson's disease: one-year clinical and neurophysiological observations in two patients with putaminal implants," *Ann Neurol.*, 1992, 31:155-165.
Madrazo et al., "Transplantation of fetal substantia nigra and adrenal medulla to the caudate nucleus in two patients with Parkinson's disease," *N Engl J Med.*, 1988, 318:51.
Marshall et al., "The therapeutic potential of human olfactory-derived stem cells," *Histol Histopathol.*, 2006, 21:633-643.
Mendez et al., "Cell type analysis of functional fetal dopamine cell suspension transplants in the striatum and substantia nigra of patients with Parkinson's disease," *Brain*, 2005, 128:1498-1510.
Metz et al., "The unilateral 6-OHDA rat model of Parkinson's disease revisited: an electromyographic and behavioural analysis," *Eur J Neurol.*, 2005, 22:735-744.
Miljan et al., "Implantation of c-mycERTAM Immortalized Human Mesencephalic-Derived Clonal Cell Lines Ameliorates Behavior Dysfunction in a Rat Model of Parkinson's Disease," *Stem Cells Devel.*, 2009, 18:307-320.
Olanow et al., "A double-blind controlled trial of bilateral fetal nigral transplantation in Parkinson's disease," *Ann Neurol.*, 2003, 54:403-414.
Olsson et al., "Forelimb akinesia in the rat Parkinson model: differential effects of dopamine agonists and nigral transplants as assessed by a new stepping test," *Journal of Neuroscience*, 1995, 15:3863-3875.
Othman et al., "Clonal analysis of adult human olfactory neurosphere forming cells," *Biotech Histochem.*, 2005, 80:189-200.
Othman et al., "Immunomagnetic separation of adult human olfactory neural progenitors," *Biotech Histochem.*, 2005, 80:177-188.
Redmond et al., "Behavioral improvement in a primate Parkinson's model is associated with multiple homeostatic effects of human neural stem cells," *Proc Natl Acad Sci USA*, 2007, 104:12175-12180.
Roisen et al., "Adult human olfactory stem cells," *Brain Res.*, 2001, 890:11-22.
Snyder & Olanow, "Stem cell treatment for Parkinson's disease: an update for 2005," *Curr Opin Neurol.*, 2005, 18:376-385.
Sonntag et al., "Stem cells may reshape the prospect of Parkinson's disease therapy," *Brain Res Mol Brain Res.*, 2005, 134:34-51.
Stahel, *Newron Pharmaceut Ann Rep.*, 2006, 123 pages.
Tian et al., "Localization of changes in beta-actin expression in remodeled canine myocardium ," *J Mol Cell Cardiol.*, 1999, 31:751-760.
Wells et al., "Cassette mutagenesis: an efficient method for generation of multiple mutations at defined sites," *Gene*, 1985, 34:315-323.
Winstead et al., "Endoscopic biopsy of human olfactory epithelium as a source of progenitor cells," *Am J Rhinol.*, 2005, 19:83-90.
Woodlee et al., "Enhanced function in the good forelimb of hemi-parkinson rats: compensatory adaptation for contralateral postural instability?" *Exp Neurol.*, 2008, 211:511-517.
Zhang et al., "Adult human olfactory neural progenitors cultured in defined medium," *Exp Neurol.*, 2004, 186:112-123.
Zhang et al., "Induction of neuronal differentiation of adult human olfactory neuroepithelial-derived progenitors," *Brain Res.*, 2006, 1073-1074:109-119.
Zhou et al., "Synthesis of functional mRNA in mammalian cells by bacteriophage T3 RNA polymerase," *Mol Cell Biol.*, 1990, 10:4529-4539.
Zoller & Smith, "Oligonucleotide-directed mutagenesis: A simple method using two oligonucleotide primers and a single-stranded DNA template," *Meth Enzymol.*, 1987, 154:329-350.
Baharlu, Simin, Authorized Officer, International Bureau of WIPO, International Preliminary Report on Patentability, International application No. PCT/US2009/062962, issued May 3, 2011, 12 pages.
Young, Lee W. Authorized Officer, International Bureau of WIPO, International Search Report and Written Opinion, International application No. PCT/US2009/062962, issued Apr. 13, 2010, 14 pages.
"Scientific misconduct and its cover-up—The story of the rotten apple", Oct. 11, 2006, http://misconductinscience.blogspot.com.
"Scientific misconduct and its cover-up; How I became a whistleblower (part 2)", Feb. 28, 2008, http://srivlin.wordpress.com.
Sosnowski J, "Mitotically active adult olfactory neurons in vitro established from the in situ ZnSO4 trauma-induced regenerating olfactory epithelium", Ph.D. Dissertation, University of Louisville, 1995.
Sosnowski et al., 1995, "Chemical traumatization of adult mouse olfactory epithelium in situ stimulates growth and differentiation of olfactory neurons in vitro", Brain Res., 702:37-48.
S. Rivlin, 2004, "Scientific misconduct and its cover-up: diary of a whistleblower", BrownWalker Press, Boca Raton, FL.
"U of L to investigate plagiarism charges", Lexington Herald-Leader on Apr. 7, 1998.
"Briefs from Barbourville, Frankfort, Louisville, Russelville", Lexington Herald-Leader on Sep. 17, 1998.
"U of L prof: colleagues stole from student's paper", Cincinnati-Kentucky Post on Apr. 7, 1998.
"Plagiarism", Cincinnati-Kentucky Post on Sep. 18, 1998.
Harkema et al., 2006, "The nose revisited: a brief review of the comparative structure, function, and toxicologic pathology of the nasal epithelium", Toxicol. Pathol., 34:252-69.

\* cited by examiner

A

B

OLFACTORY EPITHELIAL-DERIVED STEM CELLS AND METHODS OF USE THEREFOR

CROSS-REFERENCE TO RELATED APPLICATIONS

This application is a National Stage application under 35 U.S.C. 371 and claims benefit under 35 U.S.C. 119(a) of International Application No. PCT/US2009/062962, having an International Filing Date of Nov. 2, 2009, which is based on and claims priority to U.S. Provisional Application Ser. No. 61/197,896, filed Oct. 31, 2008, and U.S. Provisional Application Ser. No. 61/278,840, filed Oct. 13, 2009, the disclosure of each of which is incorporated herein by reference in its entirety.

TECHNICAL FIELD

The presently disclosed subject matter relates, in general, to olfactory epithelial-derived stem cells. More particularly, the presently disclosed subject matter relates to olfactory epithelial-derived stem cells and methods for employing the same to ameliorate nervous system damage in a subject in need thereof.

BACKGROUND

Neurological disorders, which include those that arise spontaneously (e.g., Parkinson's disease (PD) and Alzheimer's disease) and those that result from acute injury to neural tissue, generally result in significant reductions in quality of life for those who develop the disorders. Unfortunately, treatments for such disorders are generally of limited efficacy because of the inability to prevent or even reverse the progressive nature of the disorder and/or the inability to provide an individual having such a disorder with any form of repair of the damage done to the nervous tissue.

Parkinson's disease (PD) remains one of the leading causes of chronic neurological disability, which affects more than 1,500,000 Americans. The incidence rises with age, being approximately 1:1000 overall, but affecting 2% of the population over the age of 65. About 60,000 new cases are reported each year, and in recent years the annual number of deaths from PD has increased steadily (Stahel, 2006). Internationally, the incidence rate for PD approximates 17 per 100,000 per year, although this is probably an underestimate. Parkinson's disease (PD) is characterized by the extensive loss of dopaminergic (DA) neurons in the substantia nigra (SN) in the midbrain (Hornykiewicz, 1973b). Currently the principle treatment for PD is oral L-3,4-dihydroxyphenylalanine (L-dopa), which is the precursor of dopamine that can pass the blood-brain barrier (Hornykiewicz, 1973a).

L-dopa largely provides symptomatic relief, but with time becomes less effective for two reasons. First, during the progression of the disease the neurons become less sensitive to the drug. Second, L-dopa does not delay or diminish degeneration of the DA neurons (Lang & Lozano, 1998). Thus, there continues to be an ongoing need for identifying new strategies for inhibiting or even reversing the progression of PD and other neurological disorders.

Recent research has attempted to identify and isolate cell populations that can be used to replace lost or degenerating dopaminergic neurons (Marshall et al., 2006; Anderson & Caldwell, 2007). An underlying principle of cell replacement therapy is that restoration of function lost as a result of damage or disease in the CNS might be accomplished by the replacement of dead or dying cells with healthy ones. Recent studies further suggest that the engraftment of stem cells or progenitors can up regulate or enhance existing endogenous progenitor populations and possibly rescue damaged cells (Redmond et al., 2007). Other investigators have employed neural cell transplants obtained from the fetal ventral mesencephalic (VM) dopaminergic neurons (Lindvall et al., 1988; Madrazo et al., 1988; Lindvall et al., 1992; Freeman et al., 1995; Borlongan, 2000). However, these transplants frequently lead to troublesome dyskinesia (Freed et al., 2001; Olanow et al., 2003). Even when excellent dopaminergic reinnervation was obtained, which produced positive clinical improvements in the absence of dyskinesia, the amount of tissue required for each PD patient necessitated a minimum of 4-5 fetal brains (Mendez et al., 2005). This requirement increased the possibility of viral or bacteria infection that significantly limited the utility of this approach. In addition, the number of surviving neurons was highly limited as most engrafted cells died (Borlongan, 2000). The limited supply of fetal VM cells coupled with their poor graft survival severely limits the therapeutic utility of this approach for the treatment of PD. Therefore, the identification and isolation of alternate expandable sources of dopaminergic neurons have become a major research focus (Daadi, 2002; Doss et al., 2004; Lindvall et al., 2004) and continues to be an ongoing need.

Thus, there continues to be a need for new approaches to generate populations of transplantable cells suitable for a variety of applications, including but not limited to treating injury and/or disease of neurological tissues.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

The presently disclosed subject matter provides recombinant dopaminergic neurons or recombinant progenitors thereof. In some embodiments, the recombinant dopaminergic neurons or recombinant progenitors thereof comprise one or more transgenes encoding a nurr-1 polypeptide, a pitx3 polypeptide, an lmx1a polypeptide, a biologically active fragment thereof, a biologically active derivative thereof, and/or any combination thereof. In some embodiments, a single transgene encodes two or more of a nurr-1 polypeptide, a pitx3 polypeptide, an lmx1a polypeptide, a biologically active fragment thereof, a biologically active derivative thereof, and/or any combination thereof. In some embodiments, the single transgene encodes a nurr-1 polypeptide and a pitx3 polypeptide. In some embodiments, the recombinant progenitor thereof comprises a recombinant olfactory epithelial-derived stem cell comprising the one or more transgenes, or a differentiated derivative thereof.

The presently disclosed subject matter also provides methods for producing a recombinant dopaminergic neuron or recombinant progenitor thereof. In some embodiments, the methods comprise (a) providing an olfactory epithelial-derived stem cell, optionally a plurality of olfactory epithelial-derived stem cells, further optionally wherein the plurality of olfactory epithelial-derived stem cells are in the form of one or more neurospheres; and (b) introducing into the olfactory epithelial-derived stem cell one or more transgenes encoding a nurr-1 polypeptide, a pitx3 polypeptide, an Imx1a polypeptide, a biologically active fragment thereof, a biologically active derivative thereof, and/or any combination thereof, whereby a recombinant dopaminergic neuron or recombinant progenitor thereof is produced. In some embodiments, the methods comprise collecting the olfactory epithelial-derived stem cell from a cadaver. In some embodiments, the method comprises collecting the olfactory epithelial-derived stem cell from a living donor. In some embodiments, the living donor is a subject having a neurological disorder. In some embodiments, the neurological disorder is Parkinson's disease. In some embodiments, the olfactory epithelial-derived stem cell is a human olfactory epithelial-derived stem cell (optionally, and adult human olfactory epithelial-derived stem cell) and at least one of the nurr-1 polypeptide, the pitx3 polypeptide, the Imx1a polypeptide, the biologically active fragment thereof, the biologically active derivative thereof, and/or the combination thereof are derived from a species other than human. In some embodiments, the pitx3 polypeptide or the biologically active fragment or derivative thereof is a rat pitx polypeptide or a biologically active fragment or derivative thereof. In some embodiments, the Imx1a polypeptide or the biologically active fragment or derivative thereof is a mouse Imx1a polypeptide or a biologically active fragment or derivative thereof. In some embodiments, the nurr-1 polypeptide or the biologically active fragment or derivative thereof is a mouse nurr-1 polypeptide or a biologically active fragment or derivative thereof. In some embodiments, the methods further comprise culturing the olfactory epithelial-derived stem cell before, during, and/or after the introducing step in medium comprising a Sonic hedgehog (Shh) polypeptide, a biologically active fragment thereof, a derivative thereof, retinoic acid (RA) or a biologically active derivative thereof, forskolin (FN) or a biologically active derivative thereof, or any combination thereof, under conditions sufficient to induce neuronal differentiation in the olfactory epithelial-derived stem cell.

The presently disclosed subject matter also provides methods for producing lineage primed cells. In some embodiments, the methods comprise culturing an olfactory epithelial-derived stem cell in medium comprising of a Sonic hedgehog (Shh) polypeptide, a biologically active fragment thereof, a derivative thereof, retinoic acid (RA) or a biologically active derivative thereof, forskolin (FN) or a biologically active derivative thereof, or any combination thereof, under conditions sufficient to induce neuronal differentiation in the olfactory epithelial-derived stem cell, whereby a lineage primed cell comprising a dopaminergic neuron or progenitor thereof is produced. In some embodiments, the methods further comprise expressing in the recombinant olfactory epithelial-derived stem cell one or more transgenes encoding a nurr-1 polypeptide, a pitx3 polypeptide, an Imx1a polypeptide, a biologically active fragment thereof, a biologically active derivative thereof, and/or any combination thereof. In some embodiments, the one or more of the nurr-1 polypeptide, the pitx3 polypeptide, the Imx1a polypeptide, the biologically active fragment thereof, the biologically active derivative thereof, and/or the combination thereof encoded by the one or more transgenes comprises a mouse ortholog, a rat ortholog, and/or a human ortholog, a biologically active fragment thereof, a biologically active derivative thereof, or any combination thereof.

The presently disclosed subject matter also provides methods for ameliorating at least one symptom associated with a neurological disorder in a subject. In some embodiments, the methods comprise providing a dopaminergic neuron expressing one or more of a nurr-1 polypeptide, a pitx3 polypeptide, an Imx1a polypeptide, a biologically active fragment or derivative thereof or a progenitor thereof; and transplanting the recombinant dopaminergic neuron or the progenitor thereof into the subject, optionally into the substantia nigra of the subject. In some embodiments, the dopaminergic neuron is a recombinant dopaminergic neuron that comprises a transgene that (a) encodes one or more of a nurr-1 polypeptide, a pitx3 polypeptide, an Imx1a polypeptide, a biologically active fragment thereof, and a biologically active derivative thereof; and/or (b) comprises a promoter that is transcriptionally active in the dopaminergic neuron or a progenitor thereof that is operably-linked to a coding sequence encoding the nurr-1 polypeptide, the pitx3 polypeptide, the Imx1a polypeptide, or the biologically active fragment or derivative thereof. In some embodiments, the progenitor is non-recombinant. In some embodiments, the progenitor is a recombinant progenitor comprising one or more transgenes encoding a nurr-1 polypeptide, a pitx3 polypeptide, an Imx1a polypeptide, a biologically active fragment thereof, a biologically active derivative thereof, and/or any combination thereof. In some embodiments, the neurological disorder is Parkinson's disease. In some embodiments, a single transgene encodes two or more polypeptides selected from the group consisting of a nurr-1 polypeptide, a pitx3 polypeptide, an Imx1a polypeptide, a biologically active fragment thereof, a biologically active derivative thereof, and/or any combination thereof. In some embodiments, the single transgene encodes nurr-1 and pitx3 polypeptides. In some embodiments, the transplanted recombinant dopaminergic neuron or recombinant progenitor thereof induces growth and/or regeneration of one or more endogenous neurons in the subject.

The presently disclosed subject matter also provides methods for transplantation. In some embodiments, the methods comprise transplanting into a subject a dopaminergic lineage primed olfactory epithelial-derived stem cell or a progenitor thereof, wherein the dopaminergic lineage primed olfactory epithelial-derived stem cell expresses one or more transgenes that (a) encode one or more of a nurr-1 polypeptide, a pitx3 polypeptide, an Imx1a polypeptide, a biologically active fragment thereof, and a biologically active derivative thereof; and/or (b) comprise a promoter that is transcriptionally active in the dopaminergic neuron or a progenitor thereof that is operably-linked to a coding sequence encoding the nurr-1 polypeptide, the pitx3 polypeptide, the Imx1a polypeptide, or the biologically active fragment or derivative thereof, and further wherein the lineage priming has an efficiency of at least 1%, 5, or 10%. In some embodiments, the lineage priming comprises (a) providing an olfactory epithelial-derived stem cell, optionally a plurality of olfactory epithelial-derived stem cells, further optionally in the form of one or more neurospheres; and (b) introducing into the olfactory epithelial-derived stem cell one or more transgenes encoding a polypeptide selected from the group consisting of a nurr-1 polypeptide, a pitx3 polypeptide, an Imx1a polypeptide, a biologically active fragment thereof, a biologically active derivative thereof, and/or any combination thereof. In some embodiments, the plurality of olfactory epithelial-derived stem cells is isolated from a cadaver, a living donor, or a combination thereof. In some embodiments, the living donor is the subject. In some embodiments, the conditions sufficient to induce neuronal differentiation comprise culturing the olfactory epithelial-derived stem cell in a culture medium comprising about 1 µM retinoic acid, about 5 µM forskolin, and about 15 nM Sonic hedgehog for at least about 3, 4, 5, 6, or 7 days. In some embodiments, the culturing step produces a dopaminergic neuron or a recombinant progenitor thereof that expresses an endogenous tyrosine hydroxylase (TH) gene product, produces dopamine, secretes dopamine, or combinations thereof. In some embodiments, the methods further comprise culturing the olfactory epithelial-derived stem cell before, during, and/or after the introducing step in medium comprising of a Sonic hedgehog (Shh) polypeptide, a biologically active fragment thereof, a derivative thereof, retinoic acid (RA) or a biologically active derivative thereof, forskolin (FN) or a biologically active derivative thereof, or any combination thereof, under conditions sufficient to induce neuronal differentiation in the olfactory epithelial-derived stem cell. In some embodiments, the subject has a neurological disorder. In some embodiments, the neurological disorder is Parkinson's disease.

The presently disclosed subject matter also provides methods for inducing growth and/or regeneration of a neuron in a subject. In some embodiments, the methods comprise transplanting a plurality of olfactory epithelial-derived stem cells into the subject at a location and in a number sufficient to induce growth and/or regeneration of a neuron in the subject. In some embodiments, the transplanting is into a central nervous system site in the subject. In some embodiments, the central nervous system site is the substantia nigra. In some embodiments, the central nervous system site is the midbrain of the subject. In some embodiments, the subject has a neurological disorder associated with loss of dopaminergic neurons, optionally wherein the neurological disorder is Parkinson's disease. In some embodiments, the methods further comprise differentiating the olfactory epithelial-derived stem cell in vitro by expressing in the olfactory epithelial-derived stem cell one or more transgenes encoding a polypeptide selected from the group consisting of a nurr-1 polypeptide, a pitx3 polypeptide, an Imx1a polypeptide, a biologically active fragment thereof, a biologically active derivative thereof, and/or any combination thereof. In some embodiments, at least one of the nurr-1 polypeptide, the pitx3 polypeptide, and the Imx1a polypeptide is a human ortholog thereof. In some embodiments, the transplanting provides to the neuron an effective amount of a neurotrophic factor sufficient to provide/cause the neuron to grow and/or regenerate and/or survive. In some embodiments, the neurotrophic factor includes a brain-derived neurotrophic factor (BDNF).

The presently disclosed subject matter also provides methods for delivering a cytokine or a growth factor to the central nervous system of a subject. In some embodiments, the methods comprise transplanting into the subject an olfactory epithelial-derived stem cell or a differentiated derivative thereof that expresses the cytokine or the growth factor, wherein the transplanting is into a central nervous system site in the subject. In some embodiments, the cytokine or the growth factor is selected from the group consisting of brain-derived neurotrophic factor (BDNF), nerve growth factor (NGF), neurotropin 3 (NT3), neurotropin 4/5 (NT4/5), and vascular endothelial growth factor (VEGF). In some embodiments, the delivering results in restoration of a functional deficit in the subject. In some embodiments, the functional deficit results from a neurological injury in the subject. In some embodiments, the differentiated derivative thereof comprises a recombinant dopaminergic neuron or recombinant progenitor thereof comprising one or more transgenes encoding a nurr-1 polypeptide, a pitx3 polypeptide, an Imx1a polypeptide, a biologically active fragment thereof, a biologically active derivative thereof, and/or any combination thereof. In some embodiments, at least one of the nurr-1 polypeptide, the pitx3 polypeptide, and the Imx1a polypeptide is a human ortholog thereof.

The presently disclosed subject matter also provides methods for providing a dopaminergic neuron function to a subject in need thereof. In some embodiments, the methods comprise introducing a plurality of olfactory epithelial-derived stem cells and/or in vitro differentiated derivatives thereof into the midbrain of the subject in a number and under conditions sufficient to allow at least one of the plurality of olfactory epithelial-derived stem cells to differentiate into a functional dopaminergic neuron, thereby providing a dopaminergic neuron function to a subject. In some embodiments, the in vitro differentiated derivatives are differentiated by expressing in at least one olfactory epithelial-derived stem cell one or more transgenes encoding a polypeptide selected from the group consisting of a nurr-1 polypeptide, a pitx3 polypeptide, an Imx1a polypeptide, a biologically active fragment thereof, a biologically active derivative thereof, and/or any combination thereof. In some embodiments, the in vitro differentiated derivatives are differentiated by exposing at least one olfactory epithelial-derived stem cell to a neurotrophic factor that induces differentiation of the olfactory epithelial-derived stem cell to a dopaminergic neuron and/or that primes the olfactory epithelial-derived stem cell to differentiate into a dopaminergic neuron. In some embodiments, the olfactory epithelial-derived stem cells and/or in vitro differentiated derivatives thereof terminally differentiates into a functional dopaminergic neuron in the subject. In some embodiments, the introducing induces an endogenous cell in the subject to differentiate into a functional dopaminergic neuron. In some embodiments, the introducing induces repair of a non-functional or suboptimally functional endogenous dopaminergic neuron or a precursor thereof in the subject. In some embodiments, the introducing rescues a dopaminergic neuron and/or a precursor thereof from inactivation and/or death that it would have undergone in the absence of the introduced plurality of olfactory epithelial-derived stem cells and/or in vitro differentiated derivatives thereof. In some embodiments, in vitro differentiated derivatives are differentiated by growing at least one olfactory epithelial-derived stem cell on a substrate under conditions sufficient to induce differentiation of the olfactory epithelial-derived stem cell to a dopaminergic neuron and/or that primes the olfactory epithelial-derived stem cell to differentiate into a dopaminergic neuron.

The presently disclosed subject matter also provides cell cultures comprising a recombinant olfactory epithelial-derived stem cell and/or a differentiated derivative thereof. In some embodiments, the recombinant olfactory epithelial-derived stem cell and/or the differentiated derivative thereof comprises one or more transgenes encoding a nurr-1 polypeptide, a pitx3 polypeptide, an Imx1a polypeptide, a biologically active fragment thereof, a biologically active derivative thereof, and/or any combination thereof. In some embodiments, the culture comprises a culture medium comprising a Sonic hedgehog (Shh) polypeptide, a biologically active fragment thereof, a derivative thereof, retinoic acid (RA) or a biologically active derivative thereof, forskolin (FN) or a biologically active derivative thereof, or any combination thereof. In some embodiments, the culture medium comprises about 1 µM retinoic acid, about 5 µM forskolin, and about 15 nM Sonic hedgehog.

It is an object of the presently disclosed subject matter to provide a population of transplantable cells suitable for a variety of applications, including but not limited to treating injury to and/or disease of neurological tissues.

An object of the presently disclosed subject matter having been stated hereinabove, and which is achieved in whole or in part by the presently disclosed subject matter, other objects

BRIEF DESCRIPTION OF THE DRAWINGS

As seen in FIGS. 1A-1H, essentially all NSFCs transfected with pIRES-pitx3-nurr1, pLNCX2-pitx3 and pLNCX2-nurr1 expressed TH after 4 months selection with G418 (see FIGS. 1C, 1D, 1F, and 1G), but NSFCs transfected with pLNCX2-Imx1a or the control vectors (pIRES or pLNCX2) were TH-negative (see FIGS. 1B, 1E, and 1H). All cells were stained with 4',6-diamidino-2-phenylindole dihydrochloride (DAPI) to show nuclei.

FIG. 1A is a negative control for the secondary antibody employed in FIGS. 1B-1H. The signal seen is from DAPI. FIG. 1B is a negative control for the primary antibodies that bind to tyrosine hydroxylase (TH) or to pitx3. The cells stained in FIG. 1B were transfected with an empty pIRES expression vector, and the signal seen is from DAPI. The cells stained in FIGS. 1C, 1D, 1F, and 1G were transfected with expression plasmids pIRES-pitx3-nurr1 (FIGS. 1C and 1D), pLNCX2-pitx3 (FIG. 1F), or pLNCX2-nurr1 (FIG. 1G), and after 4 months selection with G418 were stained with antibodies that bound to TH and also with antibodies that bound to pitx3 or nurr1 as indicated. In each of these cases, the cells were TH-positive. FIGS. 1E and 1H show the results of NSFCs transfected with the control vector pLNCX2 or pLNCX2-Imx1a, respectively. In these cases, the cells were TH-negative.

FIG. 2A depicts Western blot analysis with an antibody that binds to TH (58 kilodaltons (kDa)) of lysates from cells transfected with, from left to right, pLNCX2, pLNCX2-pitx3, pLNCX2-nurr1, pLNCX2-Imx1a, pIRES, or pIRES-pitx3-nurr1. The Western blots were also probed with an antibody that binds to actin (43 kDa) as a loading control, in which the consistent intensities of the actin signals demonstrated that the amount of protein loaded in each lane was very similar.

FIGS. 2B-2G are curves showing actin expression as per the density of the actin signal in FIG. 2A for pLNCX2, pLNCX2-pitx3, pLNCX2-nurr1, pLNCX2-Imx1a, pIRES, and pIRES-pitx3-nurr1, respectively. FIGS. 2H-2M are curves showing TH-expression as per the density of the actin signal in FIG. 2A for pLNCX2, pLNCX2-pitx3, pLNCX2-nurr1, pLNCX2-Imx1a, pIRES, and pIRES-pitx3-nurr1, respectively. FIG. 2N is a bar graph showing the differences of each transfected NSFC line in the ratio of TH to actin expression (e.g., FIG. 2H versus FIG. 2B, FIG. 2I versus FIG. 2C, etc.).

In FIGS. 3A-3H, all cells were also stained with DAPI to show nuclei.

FIG. 3A depicts immunocytochemistry of a negative control to test the secondary antibody used in the immunocytochemistry and Western blot analyses depicted in FIGS. 3B-3I. FIG. 3B depicts the results of immunocytochemistry of another negative control showing that non-transfected NSFCs are TH−. FIG. 3C depicts the results of immunocytochemistry of another negative control showing that NSFCs transfected with an empty vector (pIRES) are TH−. FIG. 3D depicts the results of immunocytochemistry of NSFCs transfected with pIRES-pitx3-nurr1 showing that these cells are TH+. FIG. 3E depicts the results of immunocytochemistry of another negative control showing that NSFCs transfected with an empty vector (pLNCX2) are TH−. FIGS. 3F-3H depict the results of immunocytochemistry of showing that NSFCs transfected with pLNCX2-pitx3 or pLNCX2-nurr1 are TH+, but that cells transfected with pLNCX2-Imx1a are TH−. FIG. 3I shows the results of Western blot analysis that confirms that NSFCs transfected with pLNCX2-pitx3, pLNCX2-nurr1, or pIRES-pitx3-nurr1 are TH+, but cells transfected with pLNCX2-Imx1a are TH−. An antibody that binds to actin was used as a loading control in each lane.

FIG. 4A is a bar graph depicting the results of assaying intracellular dopamine levels per total protein of NSFCs transfected with various expression constructs, and FIG. 4B is a bar graph depicting the results of assaying extracellular dopamine levels per total protein of NSFCs transfected with various expression constructs. As shown in these Figures, NSFCs transfected with expression plasmid pIRES-pitx3-nurr1 were the most efficient dopamine producing cells with respect to both intracellular and extracellular dopamine levels. Intracellular and extracellular dopamine levels increased with treatment of cells with RA1FN5Shh in each specific line.

FIG. 5A depicts the results of culturing the cells in the absence of Shh. FIG. 2B depicts the results of culturing the cells in the presence of 0.25 mg/ml forskolin from Sigma-Aldrich Chemical Company (St. Louis, Mo., United States of America). FIG. 2C depicts the results of culturing the cells in the presence of 0.25 mg/ml of a highly purified forskolin preparation. Comparison of FIGS. 5B and 5C shows that cells treated with highly purified Shh expressed TH to a higher level than cells treated with the commercially available product.

FIG. 6A shows a comparison of TH-staining of cells at 18 hours, 4 days, and 7 days in DFBNM supplemented with 0.025 mg/ml of highly purified Shh alone (top three panels), in the presence of 0.025 mg/ml of highly purified Shh and 1 µM RA (middle three panels), or in the presence of 0.025 mg/ml of highly purified Shh and both 1 μM RA and 5 μM FN (bottom three panels). FIG. 6B depicts immunocytochemistry of NSFCs showing positive TH-staining after 7 days treatment with 0.025 mg/ml of highly purified Shh, 1 μM RA, and 5 μM FN (RA1FN5Shh).

FIGS. 9A and 9B are graphs showing reduced rotation velocity under the same dosage of amphetamine stimulation in an MFB model (58.2%) and in a striatum model (40.13%) relative to control non-engrafted animals.

FIGS. 9C and 9D are pictures of the rotation model apparatus.

FIGS. 9E and 9F depict immunocytochemical analyses of the brains of transplanted animals, which show that TH-positive cells are found in the brains of these animals 3 months after engraftment. These micrographs demonstrate that the engrafted population remains TH-positive and appears viable even following a three month period of transplantation into the brain, which is indicative of a high probability of their long-term survival.

DETAILED DESCRIPTION

Figure 1:
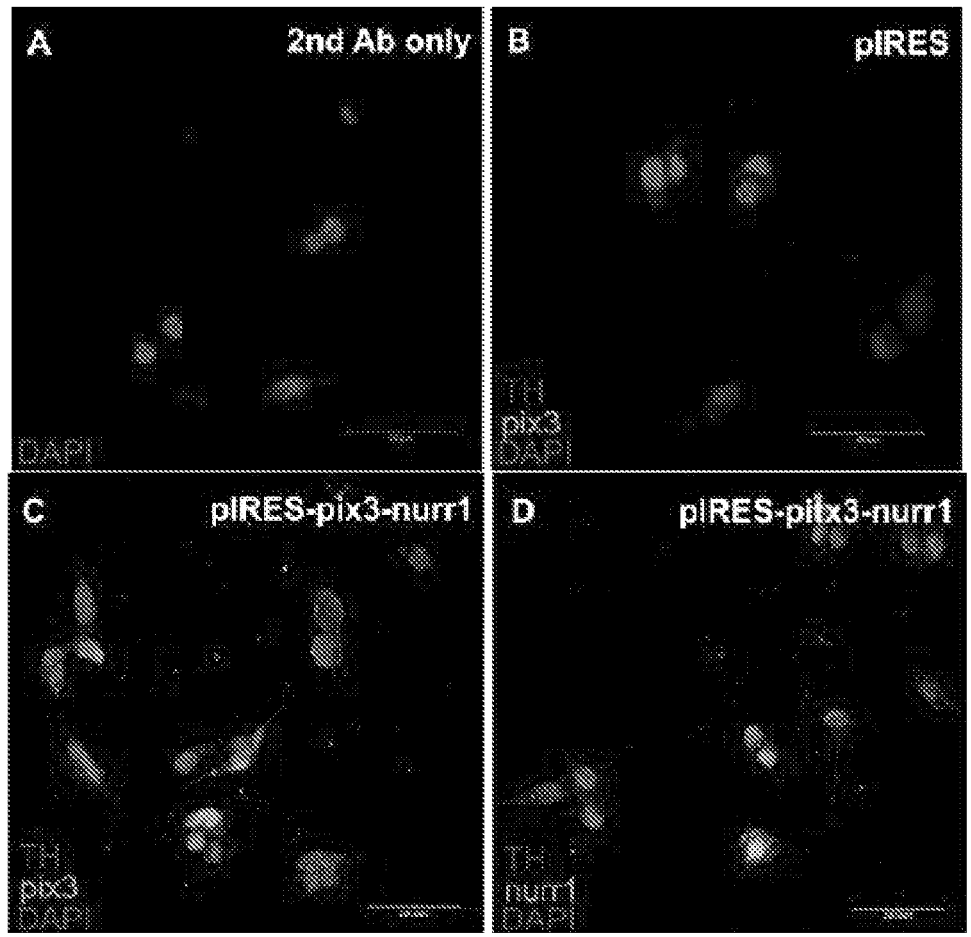
FIGS. 1A-1H are fluorescence micrographs of neurosphere-forming cells (NSFCs) transfected with expression plasmids that encoded and stained with antibodies that bind to tyrosine hydroxylase (TH), pitx3, or nurr1.
Figure 1:
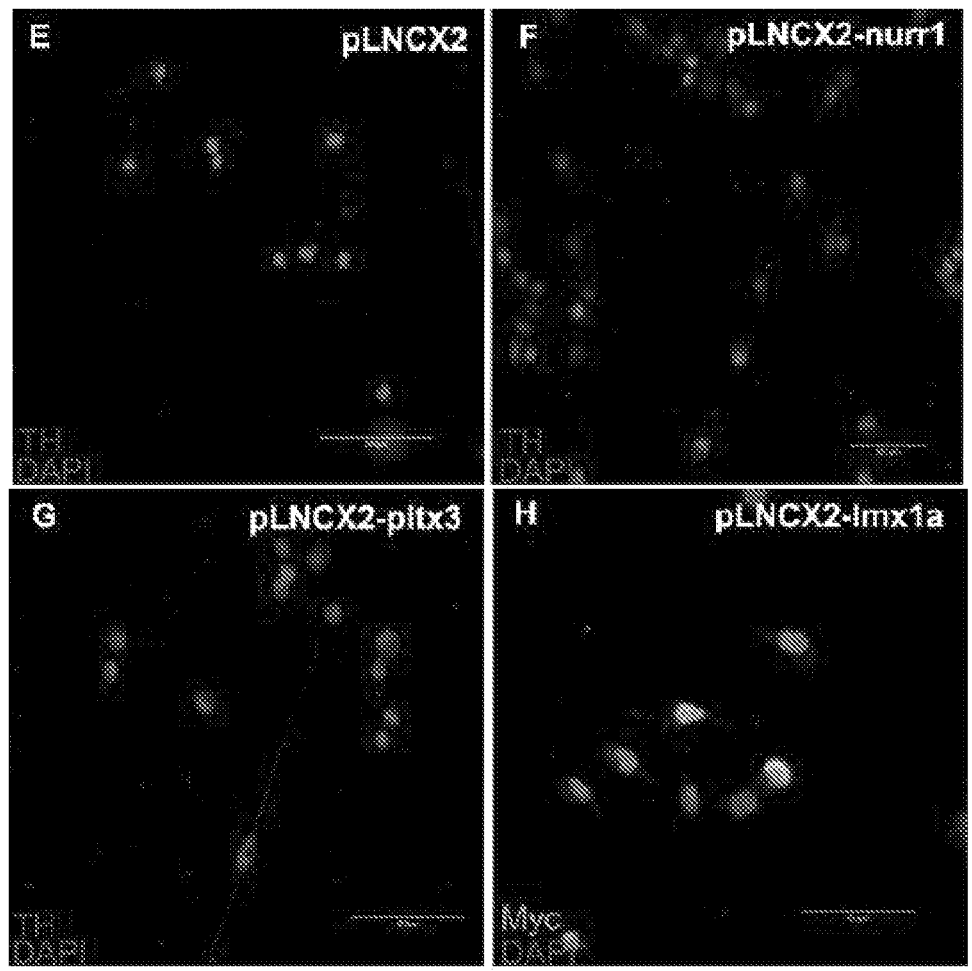

The present subject matter will be now be described more fully hereinafter with reference to the accompanying Examples, in which exemplary embodiments of the presently disclosed subject matter are described. The presently disclosed subject matter can, however, be embodied in different forms and should not be construed as limited to the embodiments set forth herein. Rather, these embodiments are provided so that this disclosure will be thorough and complete, and will fully convey the scope of the presently disclosed subject matter to those skilled in the art.

The use of stem cells and stem cell derivatives has gained increased interest in medical research, particularly in the area of providing reagents for treating tissue damage resulting from, for example, genetic defects, injuries, and/or disease processes. Ideally, cells that are capable of differentiating into the affected cell types could be transplanted into a subject in need thereof, where they would interact with the tissue microenvironment and supply the necessary cell types to repair the injury. Alternatively or in addition, transplanted cells could also influence the tissue microenvironment to provide signals that would repair and/or rescue the affected cell types in the subject and/or induce the subject's own endogenous cells to differentiate into appropriate cell types to thereby ameliorate the damage present in the tissue.

Stem cells are undifferentiated cells with a capacity for self-renewal and the potential for lineage restriction (maturation) into one or more different cell types depending on their origin and the microenvironmental signals that they receive (Lindvall et al., 2004). These characteristics make stem cells an attractive target population for cell replacement therapy (Snyder & Olanow, 2005; Sonntag et al., 2005). Human embryonic stem cells (hESCs), lineage-restricted towards dopaminergic neurons when transplanted into a rodent model of PD, provide a significant relief of symptoms. However, with time, animals engrafted with hESCs developed severe teratomas (Brederlau et al., 2006). The use of partially restricted stem cells could provide cells that are equivalent to progenitors.

The olfactory epithelium (OE) is a unique source for neural progenitors that can be harvested with endoscopic nasal surgery without invasive craniotomy (Winstead et al., 2005). Furthermore, since no demonstrable olfactory deficits result from OE biopsy (Winstead et al., 2005), the tissue can be used to generate cell populations (e.g., autologous or non-autologous progenitors and/or differentiated derivatives thereof) for patients with PD. An autologous cell source provides total histocompatibility and thus eliminates the need for immunosuppressive therapy as well as long waiting lists for available matched tissue. Alternatively or in addition, non-autologous cells can be employed with appropriate immunosuppressive treatments, as necessary.

The instant co-inventors have created methods for the isolation and culture of a neurosphere-forming population from OE (Roisen et al., 2001; Winstead et al., 2005). To date, more than 100 patient-specific cell lines of neurosphere-forming cells (NSFCs) have been established from primary cultures of human adult olfactory epithelium isolated from cadavers (Roisen et al., 2001) and patients undergoing endoscopic sinus surgery (Winstead et al., 2005). The instant co-inventors have also shown that the NSFCs have the potential to differentiate along several different neural lineages following exposure to environmental signals in vitro (Zhang et al., 2006).

The presently disclosed subject matter relates in some embodiments to methods for lineage restricting NSFCs towards dopaminergic neurons. In some embodiments, molecular techniques are applied for the transfection of the nurr1, pitx3, and/or Imx1a transcription factors into NSFCs to promote dopaminergic differentiation. In some embodiments, the NSFCs are exposed to Sonic hedgehog (Shh), an upstream regulatory factor in the formation of dopaminergic neurons, in the presence or absence of retinoic acid (RA) and/or Forskolin (FN). In some embodiments, these approaches are combined in an effort to further obtain increased efficiency and more potent dopaminergic expression.

I. Definitions

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

Following long-standing patent law convention, the terms "a", "an", and "the" mean "one or more" when used in this application, including the claims. Thus, the phrase "a stem cell" refers to one or more stem cells, unless the context clearly indicates otherwise.

The term "about", as used herein when referring to a measurable value such as an amount of weight, time, dose, etc., is meant to encompass variations of in some embodiments ±20%, in some embodiments ±10%, in some embodiments ±5%, in some embodiments ±1%, in some embodiments ±0.1%, and in some embodiments ±0.01% from the specified amount, as such variations are appropriate to perform the disclosed methods.

As used herein, the term "injury" is to be interpreted broadly to include any impact on a cell, tissue, or organ that results in an undesirable consequence to the cell, tissue, or organ. In some embodiments, an injury results from an insult that is observable or otherwise definable, but the ability to identify the source of the injury is not limiting. In some embodiments, an injury results comprises an injury to a cell and/or a tissue of the nervous system including, but not limited to a neuron. Alternatively or in addition, in some embodiments an injury can include injuries subsequent to which a cell, tissue, or organ exhibits an impaired function that is secondary to one or more causes, identifiable or not.

The term "isolated", as used in the context of a cell (including, for example, an olfactory epithelial-derived stem cell), indicates that the cell exists apart from its native environment. An isolated cell can also exist in a purified form or can exist in a non-native environment.

As used herein, the phrase "neurological disorder" refers to any disorder, including psychiatric disorders, affecting a part of the nervous system, such as the nerves, spinal cord, or brain. Neurological disorders include, but are not limited to Parkinson's disease, Alzheimer's disease, multiple sclerosis, amyotrophic lateral sclerosis, spinal cord injury, schizophrenia, autism, and bipolar disorder.

As used herein, the term "neurotransmitter" refers to any chemical or substance capable of inhibiting or exciting a postsynaptic cell. Some examples of neurotransmitters include dopamine, serotonin, and acetylcholine. It is well known that improper levels of neurotransmitters are associated with numerous disorders, including neurological disorders as described above.

As used herein, the term "neuritogenesis" refers to the formation of new processes and extension of existing processes resembling those of neurons.

As used herein, a cell exists in a "purified form" when it has been isolated away from one or more other cells that exist in its native environment, but also when the proportion of that cell in a mixture of cells is greater than would be found in its native environment. Stated another way, in some embodiments a cell is considered to be in "purified form" when the population of cells in question represents an enriched population of the cell of interest, even if other cells and cell types are also present in the enriched population. A cell can be considered in purified form when it comprises in some embodiments at least about 5% of a mixed population of cells, in some embodiments at least about 10% of a mixed population of cells, in some embodiments at least about 20% of a mixed population of cells, in some embodiments at least about 25% of a mixed population of cells, in some embodiments at least about 30% of a mixed population of cells, in some embodiments at least about 40% of a mixed population of cells, in some embodiments at least about 50% of a mixed population of cells, in some embodiments at least about 60% of a mixed population of cells, in some embodiments at least about 70% of a mixed population of cells, in some embodiments at least about 75% of a mixed population of cells, in some embodiments at least about 80% of a mixed population of cells, in some embodiments at least about 90% of a mixed population of cells, in some embodiments at least about 95% of a mixed population of cells, and in some embodiments about 100% of a mixed population of cells, with the proviso that the cell comprises a greater percentage of the total cell population in the "purified" population that it did in the population prior to the purification. In this respect, the terms "purified" and "enriched" can be considered synonymous.

As used herein, the term "pluripotent" refers to a cell that has a developmental path that is at least partially undetermined, and consequently the cell can differentiate into various differentiated cell types including, for example, neurons, oligodendrocytes, astrocytes, ensheathing cells, or glial cells. The term "multipotent" also refers to such a cell. Although pluripotent cells are able to develop into several cell types, various pluripotent cells can be limited in the number of developmental pathways they can travel. A pluripotent cell is thus distinguished from a "totipotent" cell, which itself or a daughter cell thereof can differentiate into any and all cell types in the relevant organism. It should be noted, however, that the terms "totipotent" and "pluripotent" are not intended to be mutually exclusive in the sense that a totipotent cell can also be considered pluripotent, although the reverse is not always true.

A "progenitor cell" describes any precursor cell, capable of self-renewal, whose daughter cells can commit to differentiate into other cell types (non-progenitor cells). In general, a progenitor cell is capable of extensive proliferation, generating more progenitor cells (self-renewal) as well as more lineage-restricted cells. Progenitor cells can divide asymmetrically, with one daughter cell retaining the progenitor cell state and the other being somewhat more lineage-restricted (e.g., expressing some other distinct specific function and/or phenotype). Alternatively, some of the progenitor cells in a population can divide symmetrically into progenitor cells, thus maintaining some progenitor cells in the population as a whole, while other cells in the population give rise only to non-progenitor cells. Examples of progenitor cells include certain cells obtained from olfactory epithelium, bone marrow, fat, and epidermal follicle. Examples of progenitor cells also include any cell derived from a primary cell culture that displays the attributes of progenitor cells. An example of a progenitor cell of this type includes neurosphere forming cells (NSFCs) obtained from culturing olfactory epithelium biopsy tissue (in some embodiments, human olfactory epithelium biopsy tissue, and in some embodiments adult human olfactory epithelium biopsy tissue) as described in PCT International Patent Application Publication No. WO 2003/064601, which is incorporated herein by reference in its entirety.

The phrase "progenitor cell" thus refers to a cell that displays the ability to undergo lineage-restricted specification. As such, in some embodiments a progenitor cell is a cell that is at an intermediate position along a differentiation pathway between a totipotent cell and a cell that is committed to terminal differentiation. In some embodiments, a progenitor cell is regenerative and pluripotent.

As used herein, the phrase "differentiated derivative" refers to a cell that is further along a differentiation pathway than a reference cell, which is typically a pluripotent or totipotent cell. In the context of differentiated derivatives of a progenitor, a differentiated derivative is a cell that is further along a particular differentiation pathway than is the progenitor. In some embodiments, a differentiated derivative of an olfactory epithelial-derived stem cell is a cell that is at least one step further along a given differentiation pathway than is the olfactory epithelial-derived stem cell.

The term "target tissue" as used herein refers to an intended site for accumulation of one or more cells of the presently disclosed subject matter and/or one or more substances produced by the cells of the presently disclosed subject matter (e.g., a neurotrophic factor) following administration of the one or more cells to a subject. For example, in some embodiments the methods of the presently disclosed subject matter involve a target tissue that comprises nervous tissue (e.g., neurons) that has been damaged, for example by genetic defect, injury, and/or a disease process. As such, a "target tissue" can be a location where the cells of the presently disclosed subject matter are implanted and also a location where the cells themselves or a factor (e.g., a polypeptide) is intended to act.

II. Olfactory Epithelial-derived Stem Cells

II.A. Generally

The presently disclosed subject matter relates in some embodiments to olfactory epithelial-derived stem cells, which in some embodiments are adult human olfactory epithelial-derived stem cells, and methods of use therefor. In some embodiments, the isolated olfactory epithelial-derived stem cells are employed per se, and in some embodiments the olfactory epithelial-derived stem cells are modified in vitro before being employed.

Olfactory epithelium provides a source of viable adult olfactory epithelial-derived stem cells that can be employed in, for example, research, treatment, drug development, and transplantation, which avoids the ethical concerns associated with use of embryonic and fetal stem cells. Even further, use of olfactory epithelial-derived stem cells avoids ethical concerns associated with the use of animal models and can even be used where there are no animal models. Olfactory epithelial-derived stem cells have a life long regenerative capacity; olfactory epithelial-derived stem cells located within the olfactory epithelium can replace aging and/or damaged neurons and their sustentacular cells as well as provide factors that induce the repair and/or regeneration of various types of neural cells.

The accessibility of olfactory epithelium and proliferative capacity make it a unique source for progenitor cells. Further, the ability to obtain olfactory epithelial-derived stem cells including, but not limited to human olfactory epithelial-derived stem cells and/or adult human olfactory epithelial-derived stem cells, from the nasal cavity eliminates the need to use highly invasive and damaging procedures that are currently available to obtain post-embryonic stem cells. In addition, since one of the greatest problems encountered in transplantations is tissue rejection, providing the presently disclosed subject matter cells for autologous transplantation eliminates the need to identify a histocompatible donor and thereby eliminates rejection. It is noted, however, that non-autologous cells can also be employed if desired, and if necessary appropriate immunosuppressive treatments can be used to reduce rejection.

As used herein, the phrase "olfactory epithelial-derived stem cell" refers to a cell that in some embodiments has at least two of the following characteristics, in some embodiments has at least three of the following characteristics, in some embodiments has least four of the following characteristics, in some embodiments at least five of the following characteristics, and in some embodiments all of the following characteristics:

i) divides every 18-24 hours for over 200 passages when cultured in standard tissue culture medium supplemented with up to 10% heat inactivated fetal calf serum;
ii) immunoreactivity for the marker β-tubulin isotype III is significantly elevated when the cell is grown on various substratum, such as a matrix coated with a mixture of enctanin, laminin, and collagen IV (ECL-matrix), or alternatively a matrix coated with laminin or fibronectin;
iii) immunoreactivity for β-tubulin isotype III is pronounced and generally demonstrates a well-developed microtubule network;
iv) addition of dibutyryl cAMP to a culture growing on ECL-matrix results in the cells forming processes;
v) immunopositive for nestin;
vi) expresses and is immunopositive for peripherin;
vii) does not require a feeder layer for growth and proliferation;
viii) does not require exogenous EGF or FGF for its survival or differentiation in culture; and
ix) immunopositive for one or more Trk receptors.

In some embodiments, the olfactory epithelial-derived stem cell is a mammalian olfactory epithelial-derived stem cell. In some embodiments, the olfactory epithelial-derived stem cell is a human olfactory epithelial-derived stem cell, which optionally can be an adult human olfactory epithelial-derived stem cell.

That human olfactory epithelial-derived stem cells can be manipulated in vitro to form neurospheres from donors as old as 95 years of age demonstrates a remarkable degree of neuroplasticity in these cells. Furthermore, the direct, minimally invasive surgical accessibility of human olfactory epithelial-derived stem cells, coupled with their pluripotency, makes olfactory epithelial-derived stem cells a good autologous source of progenitor cells. These cells can be removed, expanded, and optionally manipulated ex vivo prior to return, via transplantation to the donor, for regeneration and/or repair of damaged neural tissue. These pluripotent stem cells can also be used to generate patient-specific cell populations for genetic or diagnostic evaluation and treatment.

As such, the phrases "olfactory epithelial-derived stem cells" and "neurosphere forming cell" (NSFC) are used interchangeably to refer to regenerative, pluripotent progenitor cells from the olfactory epithelium (including, but not limited to the olfactory epithelium of a human, optionally an adult human) that display the ability to form a cluster of about 20 to 80 or more mitotically active neural (e.g., neuronal and glial) precursors that in some embodiments are positive for the neural stem cell marker protein nestin. Morphologically, NSFCs represent a population of neural cells in different stages of maturation formed by a single, clonally expanding progenitor that forms spherical, tightly packed cellular structures. In some embodiments, human NSFCs react with antibodies specific for human polypeptides and have at least two, three, four, five, or more of the characteristics listed hereinabove for olfactory epithelial-derived stem cells.

II.B. Isolation and Culture of Human Olfactory Epithelial-derived Stem Cells

Exemplary methods for isolating human olfactory epithelial-derived stem cells have been described, and similar methods can be employed to isolate and culture olfactory epithelial-derived stem cells from other animals (e.g., other mammals). See PCT International Patent Application Publication No. WO 2003/064601. As set forth therein, human olfactory epithelial tissue is first removed from the nasal cavity. The skilled artisan will appreciate that the olfactory epithelial tissue can be removed using a variety of methods. An exemplary method for removing the olfactory epithelial tissue involves the use of an endoscope having a fiber optic cable with a "pincher" at one end, to take a biopsy. An advantage of this exemplary method is that it permits obtaining tissue samples from live donor individuals with minimal invasiveness and discomfort. A further advantage of removing olfactory epithelial tissues using an endoscope is the ability to freeze or culture the olfactory epithelium stem cells obtained in an initial collection and the ability to take multiple collections when needed for in vitro culture viability or to reach a desired level of stem cell quantity.

A lateral rhinotomy is another exemplary method for removing olfactory epithelium tissues. A lateral rhinotomy is an operative procedure in which the nose is incised along one side so that it can be turned away to provide full access to the nasal cavity and olfactory epithelium tissue. However, this procedure is highly invasive. In some embodiments, the lateral rhinotomy procedure is utilized to remove olfactory epithelium tissues from a cadaver. In this method, the cadaver is in some embodiments no more than eighteen hours postmortem, in some embodiments is no more than six hours postmortem, and in some embodiments, the cadaver is immediately postmortem.

Once removed, the human olfactory epithelium can be cultured. For example, olfactory epithelium can be cultured in medium containing Dulbeccos's Modified Eagle Medium (DMEM) and F12 (1:1) with 10% heat-inactivated fetal bovine serum (FBS; all media components are available from GIBCO, Grand Island, N.Y.). Other media can be employed, as recognized by the skilled artisan, as well as different animal sources of sera or the use of serum-free media. Furthermore, some cultures can employ additional supplements, including but not limited to amino acids (such as glutamine), growth factors, etc.

A variety of substrata can be used to culture the cells, for example, plastic or glass, coated or uncoated substrata can be used. For example, a substratum can be a laminin-fibronectin coated plastic plate. Alternatively the substratum can be coated with extracellular matrix molecules (for example, to encourage adhesion or to control cellular differentiation), collagen, or poly-L-lysine (for example, to encourage adhesion free of biological effects). The cell culture substratum can also be treated to be charged.

In the case where substratum adhesion is undesired, spinner cultures can be used, wherein cells are kept in suspension. Further, in some embodiments the composition of the substratum can play a role in differentiation of olfactory epithelium stem cells.

The removed olfactory epithelium not only contains pluripotent olfactory epithelial-derived stem cells/NSFCs, but it can also contain olfactory receptor neurons (ORNs), olfactory ensheathment cells (OECs, also referred to as sustentacular cells), epithelial supporting cells, fibroblasts, and/or endothelial cells and/or leukocytes that can be isolated along with the olfactory epithelial-derived stem cells from the underlying connective tissue. After culturing for several weeks, a population of mitotically active cells emerges, while the ORNs and OECs typically become vacuolated, retract their processes, and die after approximately three to eight weeks in vitro. The mitotically active cells typically can double every day in culture.

After an additional few days of undisturbed proliferation, neurospheres begin to form. This generally occurs in 5-60% or more of the cultures, so multiple cultures can be produced to ensure a collection of cells. The neurospheres can be collected from the culture by a variety of methods. In some embodiments, the neurospheres begin to float and can be removed with simple aspiration. After harvest, neurospheres (and the cells that make up the neurospheres) can be washed and separated from unwanted debris by centrifugation with or without a gradient (continuous or step, such as with polyethylene glycol or sucrose), or sorted, if desired, by FACS or other binding-based techniques such as but not limited to the use of antibodies to a specific cell marker coated on beads (in some embodiments magnetic beads).

In some embodiments, all collection methods are performed aseptically. One of skill in the art will know how to properly determine useful parameters, such as incubation times with cell removal agents (chemical or enzymatic), temperatures, centrifugal force, and number and type of washes. After collection, the neurospheres can be mechanically dispersed into individual cells, repeatedly washed with an osmotically-appropriate (buffered or unbuffered) solution, usually provided by salt solutions, such as saline or Ringer's solution, centrifuged to remove cell debris, and then replated at in some embodiments $10^3$ cells per $mm^2$. In some embodiments, the cells are replated in individual wells of a tissue culture dish and grown clonally.

The cells can be further isolated from these replated cells and characterized by probing the cells with lineage-specific antibodies, or examining them for other useful markers. Initially, determining whether neurons are present in the isolated cell cultures might be desirable. In addition to simple microscopic inspection, neurons can be more sensitively detected by the presence of one or more of the following exemplary markers: nestin, neurofilament proteins, peripherin, Microtubule Associated Protein 2ab (MAP2ab), β-tubulin isotype III, A2B5 (see Dubois et al., 1990; Roisen et al., 2001; available from INVITROGEN™ Corp., Carlsbad, Calif., United States of America), and NGF receptor. See also Table 1 of PCT International Patent Application Publication No. WO 2003/064601.

Glial cells can be detected in some embodiments by the presence of a glial membrane enriched ganglioside with a monoclonal antibody, such as A2B5 (see Dubois et al., 1990; Roisen et al., 2001; available from INVITROGEN™ Corp., Carlsbad, Calif., United States of America).

Astrocytes can be detected in some embodiments by the presence of glial fibrillary acid protein (GFAP) using standard techniques known to one of ordinary skill in the art after review of the instant disclosure.

The presently disclosed subject matter thus also provides cell cultures comprising an olfactory epithelial-derived stem cell (in some embodiments, a human olfactory epithelial-derived stem cell and in some embodiments an adult human olfactory epithelial-derived stem cell) and/or a differentiated derivative thereof. In some embodiments, the epithelial-derived stem cell and/or a differentiated derivative thereof is a recombinant epithelial-derived stem cell and/or a differentiated derivative thereof, wherein the recombinant olfactory epithelial-derived stem cell and/or the differentiated derivative thereof comprises one or more transgenes encoding a nurr-1 polypeptide, a pitx3 polypeptide, a lmx1a polypeptide, a biologically active fragment thereof, a biologically active derivative thereof, or any combination thereof. In some embodiments, the cell culture comprises a culture medium comprising a Sonic hedgehog (Shh) polypeptide (including, but not limited to a human Shh polypeptide) and/or a biologically active fragment or derivative thereof; retinoic acid (RA) and/or a biologically active derivative thereof, forskolin (FN) and/or a biologically active derivative thereof, or any combination thereof. In some embodiments, the culture medium comprises about 1 μM retinoic acid, about 5 μM forskolin, and about 15 nM Sonic hedgehog (Shh). In some embodiments, the Shh comprises a human Shh polypeptide.

II.C. Manipulation of Olfactory Epithelial-derived Stem Cells

The term "vector" refers to any nucleic acid that is capable of delivering a nucleotide sequence to a cell, and/or expressing an exogenous nucleotide sequence, and/or recombining with an endogenous sequence following introduction into a cell.

A "marker" can be used to determine the differentiated state of a cell. Markers are characteristic, whether morphological or biochemical (enzymatic), particular to a cell type, or molecules expressed by the cell type. In some embodiments, such markers are proteins, and in some embodiments possess an epitope for antibodies or other binding molecules available. However, a marker can comprise any molecule found in a cell, including but not limited to, proteins (peptides and polypeptides), lipids, polysaccharides, gangliosides, nucleic acids, steroids, and derivatives thereof. Markers can be detected by any method available to one of skill in the art.

In addition to antibodies (and all antibody derivatives) that recognize and bind to at least one epitope on a marker molecule, markers can be detected using analytical techniques, such as but not limited to protein dot blots, sodium dodecyl sulfate polyacrylamide gel electrophoresis (SDS-PAGE), and any other gel system that separates proteins, with subsequent visualization of the marker (such as Western blots); gel filtration; affinity column purification; morphologically, such as but not limited to fluorescent-activated cell sorting (FACS), staining with dyes that have a specific reaction with a marker molecule (such as ruthenium red and extracellular matrix molecules), specific morphological characteristics (such as the presence of microvilli in epithelia, or the pseudopodia/filopodia in migrating cells, such as fibroblasts and mesenchyme); and/or biochemically, such as assaying for an enzymatic product or intermediate, or the overall composition of a cell, such as the ratio of protein to lipid, or lipid to sugar, or even the ratio of two specific lipids to each other, or polysaccharides. In the case of nucleic acid markers, any known method can be used. If such a marker is a nucleic acid, PCR, RT-PCR, in situ hybridization, dot-blot hybridization. Northern blots, Southern blots and the like can be used, coupled with suitable detection methods.

A marker or a combination of markers can show specificity to a cell type.

Myofibrils, for example, are characteristic solely of muscle cells; axons are only found in nervous tissue, cadherins are typical of epithelia, $\beta_2$-integrins to white blood cells of the immune system, and a high lipid content characteristic of oligodendrocytes while lipid droplets are unique to adipocytes. A list of markers that can be used in the presently disclosed subject matter is provided in Table 1 of PCT International Patent Application Publication No. WO 2003/064601, incorporated by reference herein in its entirety.

Alternatively if commercial antibodies are not available, one of skill in the art will know how to make antibodies, including, but not limited to polyclonal antibodies, monoclonal antibodies, fragments thereof (such as, but not limited to Fab, Fv, Fab', F(ab')$_2$, and single chain and humanized derivatives thereof). For example, an antibody can be made in the following manner.

Polyclonal antibodies can be raised against a mammalian host by one or more injections of an immunogen and, if desired, an adjuvant. Typically, the immunogen (and adjuvant) is injected in the mammal by a subcutaneous or intraperitoneal injection. The immunogen can include molecules such as polypeptides, whole cells, or fractions of cells, and can be recombinantly produced or non-recombinantly produced. Examples of adjuvants include Freund's complete and monophosphoryl Lipid A synthetic-trehalose dicorynomycolate (MPL-TDM). To improve the immune response, an immunogen can be conjugated to a polypeptide that is immunogenic in the host, such as keyhole limpet hemocyanin (KLH), serum albumin, bovine thyroglobulin, and soybean trypsin inhibitor. Protocols for antibody production are well-known (Harlow & Lane, 1988). Alternatively, pAbs can be made in chickens, producing IgY molecules (Schade & Hlinak, 1996).

A monoclonal antibody (mAb; plural mAbs) can also be made by immunizing a host or lymphocytes from a host, harvesting the mAb-secreting (or potentially secreting) lymphocytes, fusing the harvested lymphocytes to immortalized cells (e.g., myeloma cells), and selecting those cells that secrete the desired mAb. The mAbs can be isolated or purified from the culture medium or ascites fluid by conventional procedures such as protein A-SEPHAROSE®, hydroxylapatite chromatography, gel electrophoresis, dialysis, ammonium sulfate precipitation, or affinity chromatography (see e.g., Harlow & Lane, 1988; Harlow & Lane, 1999; U.S. Pat. Nos. 5,753,230; 5,733,876; 5,762,918; 5,776,427; 5,766,591; and 5,660,827; the entirety of each of which is herein incorporated by reference).

The term "plasticity" refers to the ability of a cell to vary in developmental pattern; i.e., the ability to be molded or altered. In some embodiments, a cell that demonstrates "plasticity" demonstrates the ability to differentiate into various cell types. As such, the term "neuroplasticity" refers to the ability of a cell to differentiate into a cell of the neural lineage.

The term "differentiation" refers to the acquisition or possession of one or more characteristics or functions different from that of the predecessor cell type. A differentiated cell is one that has a different character or function from the surrounding structures or from the precursor of that cell (even the same cell).

Differentiation gives rise from a limited set of cells (for example, in vertebrates, the three germ layers of the embryo: ectoderm, mesoderm and endoderm) to cellular diversity, creating all of the many specialized cell types that comprise an individual.

Differentiation is a developmental process whereby cells assume a specialized phenotype; i.e., acquire one or more characteristic or functions distinct from other cell types. In most uses, the differentiated phenotype refers to a cell phenotype that is at the mature endpoint in some developmental pathway. In many but not all tissues, the process of differentiation is coupled with exit from the cell cycle; in these cases, the cell loses or is greatly restricted in its capacity to proliferate.

A "differentiation factor" is any chemical or thing that will cause differentiation. This includes, for example, substrates and growth factors.

As sued herein, the phrase "growth factor" refers to a substance (e.g., a cytokine) that promotes cell growth and development by directing cell maturation and differentiation. Growth factors can also mediate tissue maintenance and repair. Growth factors are bound by specific receptors and act at very low concentrations. Many growth factors are mediated, at least partially, by second messengers, such as cyclic AMP (cAMP). Members of the neurotrophin family (NGF, BDNF, NT3, and NT4/5) play a key role in neuronal development, differentiation, and survival. Growth factors of the neurotrophin family typically act through tyrosine kinase receptors (Trks).

In some embodiments, an olfactory epithelial-derived stem cell, or a derivative thereof, expresses a growth factor or cytokine of interest. Exemplary growth factors and cytokines expressed by olfactory epithelial-derived stem cells and their derivatives include, but are not limited to NGF, BDNF, NT3, NT4/5, and VEGF.

Suitable medium and conditions for generating primary cultures and maintaining the above neurosphere cultures are well known in the art and can vary depending on the cell types present. For example, skeletal muscle, bone, neurons, skin, liver and embryonic stem cells are all grown in media differing in their specific contents. Furthermore, media for one cell type can differ significantly from lab to lab and institution to institution. To keep cells dividing, serum, such as fetal calf serum, is added to the medium in relatively large quantities, 1-30% by volume, again depending on cell or tissue type. Specific purified growth factors or cocktails of multiple growth factors can also be added or are sometimes substituted for serum. When differentiation is desired and not proliferation, serum with its mitogens is generally limited to about 0-2% by volume. Specific factors or hormones that promote differentiation and/or promote cell cycle arrest can also be used.

Physiologic oxygen and subatmospheric oxygen conditions can be used at any time during the growth and differentiation of cells in culture, as a critical adjunct to selection of specific cell phenotypes, growth and proliferation of specific cell types, or differentiation of specific cell types. In general, physiologic or, low oxygen-level culturing is accompanied by methods that limit acidosis of the cultures, such as addition of strong buffer to medium (such as HEPES), and frequent medium changes and changes in $CO_2$ concentration.

In addition to oxygen, the other gases for culture typically are about 5% carbon dioxide and the remainder is nitrogen, but optionally can contain varying amounts of nitric oxide (starting as low as 3 ppm), carbon monoxide, and other gases, both inert and biologically active. Carbon dioxide concentrations typically range around 5%, but can vary between 2-10%. Both nitric oxide and carbon monoxide, when necessary, are typically administered in very small amounts (i.e., in the ppm range), determined empirically or from the literature.

The medium can be supplemented with a variety of growth factors, cytokines, serum, etc. Examples of suitable growth factors are neuronal growth factor (NGF), NT3, NT4/5, brain-derived neuronal factor (BDNF) and colony stimulating factor (CSF). Examples of hormone medium additives are estrogen, progesterone, testosterone, or glucocorticoids such as dexamethasone. Examples of cytokine medium additives are interferons, interleukins, or tumor necrosis factor-$\alpha$ (TNF-$\alpha$). One skilled in the art will understand how to test additives and culture components in different culture conditions, as these can alter cell response, active lifetime of additives, or other features affecting their bioactivity. In addition, the surface on which the cells are grown can be plated with a variety of substrates that contribute to survival, growth, and/or differentiation of the cells. These substrates include but are not limited to laminin, ECL-matrix, collagen, poly-L-lysine, poly-D-lysine, polyornithine, and fibronectin. In some instances, when 3-dimensional cultures are desired, extracellular matrix gels can be used, such as collagen, ECL-matrix, or gelatin. Cells can be grown on top of such matrices, or can be cast within the gels themselves. For example, the use of an ECL-matrix promoted the lineage restriction of the olfactory epithelium derived cells toward maturing neurons as indicated by the level of neuritogenesis.

To manipulate DNA in vitro so that the cells of the presently disclosed subject matter are engineered with exogenous nucleic acid sequences, many techniques are available to those skilled in the art (see e.g., Sambrook & Russell, 2001; Ausubel et al., 2002; Ausubel et al., 2003).

Vectors are tools used to shuttle DNA between host cells or as a strategy to express a nucleotide sequence. Some vectors function only in prokaryotes, while others function in both prokaryotes and eukaryotes, facilitating large-scale DNA preparation from prokaryotes for expression in eukaryotes. Inserting the DNA of interest is accomplished by ligation techniques and/or mating protocols well known to the skilled artisan. The DNA is inserted such that its integration does not disrupt any necessary components of the vector. In the case of vectors that are used to express the inserted encoded polypeptide, the introduced DNA can be operably-linked to vector elements that govern its transcription and translation.

As used herein, the phrase "operably-linked" refers to a nucleotide sequence of interest that is linked to one or more regulatory sequences such that expression of the nucleotide sequence under the control of the one or more regulatory sequences is achieved.

Vectors can be divided into two general classes: Exemplary cloning vectors include replicating plasmids, cosmids, phage, and bacterial artificial chromosomes (BACs) that comprise regions that are non-essential for propagation in an appropriate host cell and into which foreign DNA can be inserted, resulting in the foreign DNA being replicated and propagated in the host cell. An expression vector (such as a plasmid, yeast, or animal virus genome) can be used to introduce foreign genetic material into a host cell or tissue in order to transcribe and translate the foreign DNA. In expression vectors, the introduced DNA is operably-linked to elements, such as promoters, that signal to the host cell to transcribe the inserted DNA. Exemplary promoters include constitutive promoters, inducible promoters (i.e., that control gene transcription in response to specific factors), and tissue-specific promoters.

Vectors have many manifestations. A "plasmid" is a circular double stranded DNA molecule that can accept additional DNA fragments. Viral vectors can also accept additional DNA segments into the viral genome. Certain vectors are capable of autonomous replication in a host cell (e.g., bacterial vectors having a bacterial origin of replication and episomal mammalian vectors). Other vectors (e.g., non-episomal mammalian vectors) integrate into the genome of a host cell and replicate as part of the host genome. In general, useful expression vectors are plasmids and viral vectors (e.g., replication defective retroviruses, adenoviruses, and adeno-associated viruses); other expression vectors can also be used.

Alternatively, the vectors can be transcribed and translated in vitro, for example using T7 promoter regulatory sequences and T7 RNA polymerase.

III. Recombinant Dopaminergic Neurons and Recombinant Progenitors Thereof, Including Methods for Producing the Same The presently disclosed subject matter makes use of the discovery of methods for manipulating progenitor cells, such as neurosphere-forming cells (NSFCs), to produce lineage primed cells suitable for use in cell replacement strategies and/or for delivering neurotrophic factors to target tissues. Lineage priming of NSFCs results in cell-restricted lineage pathways leading in some embodiments to dopaminergic lineage primed cells. These lineage primed cells can be transplanted into subjects with central nervous system trauma and/or neurodegenerative diseases, and are particularly useful for autologous transplantation.

The progenitor cells that can be isolated from olfactory epithelium (in some embodiments, human olfactory epithelium and in some embodiments adult human olfactory epithelium) remain relatively undifferentiated when maintained in a minimal medium, such as but not limited to MEM10, or when exposed to a variety of defined media and trophic factors. These NSFC cultures appear to have an immature neuronal default in which more than 97% of the cells express both β tubulin III and peripherin and typically more than one-half of the population of the cells express nestin. This suggests that the NSFC cultures obtained from adult human olfactory epithelium might be different from embryonic and/or other types of neural stem cells.

However, in some embodiments the human NSFC cultures disclosed herein have characteristics of neural progenitor cells. For example, the cells typically do not appear to express the astrocytic marker glial fibrillary acidic protein (GFAP), the microglial marker OX42, the oligodendrocyte markers galactocerebroside (GalC) or myelin basic protein (MBP), or the mature neuronal markers Neuronal Nuclei (NeuN), HB9, Isl 1/2, vesicular acetylcholine transporter (VAChT), choline acetyltransferase (ChAT), and tyrosine hydroxylase (TH), each of which is indicative of a central nervous system cell type that has undergone lineage-restricted specification beyond the progenitor stage. It is noted, however, that a small fraction of the cells might express one or more of these markers, and this fact does not exclude this fraction of cells from being encompassed by the term "NSFC".

To determine whether NSFCs can undergo lineage priming along cell-restricted lineage pathways using lineage priming agents, NSFC cultures were treated simultaneously with different concentrations and combinations of RA, FN, and Shh in vitro. Depending upon the treatment regimen, the NSFC cultures can in some embodiments undergo lineage priming to produce neurites having characteristics of motoneuronal lineage primed cells and dopaminergic lineage primed cells. In some embodiments, NSFCs do not form these lineage primed cell types upon treatment with RA, FN, or Shh alone.

In some embodiments, lineage priming can be affected by treating NSFC cultures for seven days with RA in the presence of FN, Shh, or a combination of FN and Shh. In some embodiments, at least 1 µM RA in combination with FN at a concentration of 1 µM to 10 µM, including but not limited to 1 µM, 2 µM, 3 µM, 4 µM, 5 µM, 6 µM, 7 µM, 8 µM, 9 µM, and 10 µM, can result in motoneuronal and dopaminergic lineage primed cells. Alternatively, at least 1 µM RA in combination with Shh at a concentration of 5 nM to 20 nM, including but not limited to 5 nM, 6 nM, 7 nM, 8 nM, 9 nM, 10 nM, 11 nM, 12 nM, 13 nM, 14 nM, 15 nM, 16 nM, 17 nM, 18 nM, 19 nM, and 20 nM, can result in motoneuronal and dopaminergic lineage primed cells. In some embodiments, at least 1 µM RA in combination with FN at a concentration of 1 µM to 10 µM (including, but not limited to 2 µM, 3 µM, 4 µM, 5 µM, 6 µM, 7 µM, 8 µM, and 9 µM) and Shh at a concentration of 5 nM to 20 nM (including, but not limited to 5 nM, 6 nM, 7 nM, 8 nM, 9 nM, 10 nM, 11 nM, 12 nM, 13 nM, 14 nM, 15 nM, 16 nM, 17 nM, 18 nM, 19 nM, and 20 nM) results in motoneuronal and dopaminergic lineage primed cells. And in some embodiments, at least 1 µM RA in combination with 5 µM FN and 15 nM Shh results in motoneuronal and dopaminergic lineage primed cells. In some embodiments, none of these treatments affects cell viability.

Following treatment of NSFC cultures with, for example, 1 µM RA in combination with 5 µM FN and 15 nM Shh for seven days, the resultant motoneuronal and dopaminergic lineage primed cells express mature neuronal antigens. Approximately 97% of the NSFCs were β-tubulin III-positive and peripherin-positive, about 82% were Tau-positive, and about 86% were α-internexin-positive. Furthermore about 31% of the treated NSFCs expressed NF68 localized in the cell soma while about 27% of the cells expressed NF160 and 24% of the cells expressed NF200 in the soma and neuritic processes. By contrast, nestin expression decreased in the treated cells to about 17% and no GFAP, OX42, GalQ, or MBP was detected. Moreover, labeling experiments confirmed that NSFCs treated with 1 µM RA in combination with 5 µM FN and/or 15 nM Shh did not incorporate significant amounts of BrdU, but did induce expression of NeuN. Thus, the NSFCs undergo lineage-restricted specification along a neuronal pathway that includes motoneuronal and dopaminergic lineage primed cells.

Furthermore, about 12% of the treated NSFCs form dopaminergic lineage primed cells, as evidenced by the expression of the dopaminergic neuronal specific antigen, tyrosine hydroxylase. The TH-positive cells failed to express ChAT or VAChT, thereby delineating these cells as dopaminergic lineage primed cells rather than motoneuronal lineage primed cells.

Thus, in some embodiments the presently disclosed subject matter provides recombinant dopaminergic neurons and/or recombinant progenitors thereof, as well as methods of producing recombinant dopaminergic neurons and/or recombinant progenitors thereof.

In some embodiments, recombinant dopaminergic neurons and/or recombinant progenitors thereof are produced by transforming a cell capable of differentiating into a dopaminergic neuron with a nucleic acid (e.g., a transgene, optionally present in an expression cassette, further optionally present in an expression vector) that encodes and/or transcriptionally activates one or more polypeptides that are capable of inducing differentiation of a progenitor cell into a dopaminergic neuron (e.g., a "lineage priming agent" as defined herein). As used herein, the phrase "a nucleic acid that transcriptionally activates" refers to nucleic acid sequence that when inserted into a cell causes transcription of a gene of interest (in some embodiments, an endogenous gene of interest) in the cell to be transcribed at a higher level than would have occurred in the absence of the nucleic acid sequence. For example, a promoter that is transcriptionally active in a cell can be introduced into the cell under conditions sufficient to homologously integrate the promoter into a position on a chromosome that operably links a coding sequence of interest to the promoter, thereby causing the coding sequence of interest to be expressed in the cell. In some embodiments, a cell capable of differentiating into a dopaminergic neuron comprises an olfactory epithelial-derived stem cell/NSFC, which can optionally be a human olfactory epithelial-derived stem cell/NSFC or an adult human olfactory epithelial-derived stem cell/NSFC).

The terms "transformation" and grammatical variants thereof refer to any alteration in gene expression resulting in a phenotypic change to a cell. Examples of transformation include increasing or decreasing the expression of an endogenous gene by incorporation of lineage priming agents inside cells (e.g., by providing to the cells transgenes that encode the lineage priming agents) or by contacting cells with lineage priming agents.

The term "exogenous" refers to anything that is exposed to a cell or introduced into a cell that originates from outside the cell. An example of an exogenous nucleic acid sequence is a transgene. It is noted that a nucleic acid can be considered "exogenous" if it is being supplied to a cell in recombinant form, even though the cell itself might have an endogenous copy of that nucleic acid. For example, human cells (e.g., human NSFCs) comprise endogenous human nurr-1 sequences and can produce a human nurr-1 polypeptide endogenously. However, a human nurr-1 transgene that is transfected into a human NSFC would be considered an exogenous nucleic acid since it is supplied to the NSFC exogenously in recombinant form. Similarly, daughter cells of a transfected NSFC that carry a nurr-1 transgene (i.e., an exogenous nurr-1 nucleic acid) would also be considered to comprise exogenous nurr-1 sequences despite the fact that the daughter cell itself was not transfected with an exogenous nucleic acid.

In contrast, the term "endogenous" refers to a molecule (e.g., a polypeptide, small molecule, etc.) that exists naturally in a cell or is produced naturally within a cell other than by transcription and/or translation of an exogenous nucleic acid. As such, in some embodiments the terms "endogenous" and "exogenous" are antonyms.

The phrase "lineage priming agent" refers to any composition that is capable of lineage priming. For example, a lineage priming protein is a protein that alone or with other agents is capable of lineage priming. Other examples of lineage priming agents include exogenous gene sequences, including coding sequences, such as open reading frames that encode a protein, and non-coding sequences, such as promoter and enhancer transcriptional elements that can enhance expression of endogenous genes following recombination of such sequences into cells; nucleic acids; and small molecules, such as organic molecules having a mass less than 1,000 daltons, and mixtures thereof.

In some embodiments, a lineage priming agent comprises a coding sequence of a gene that when expressed in a progenitor cell alone or in combination with other lineage priming agents induces differentiation of the progenitor cell into a dopaminergic neuron. The following genes and the products encoded by them, including DNA, RNA, and protein, are dopaminergic lineage priming agents, and can come from any vertebrate organism, including human, monkey, mouse, dog, chicken, frog, bovine, horse, sheep, and pig: Sonic hedgehog (Shh), nurr-1, pitx3, and lmx1a. The phrase "lineage priming agent" includes each of these genes, variants thereof, and mixtures thereof. Representative biosequences of homologs and orthologs corresponding to these gene products are presented in Table 1.

TABLE 1

GENBANK ® Accession Nos. of
Exemplary Lineage Priming Agents

| Gene | Species | Nucleic Acid | Amino Acid |
|---|---|---|---|
| nurr-1 | H. sapiens | NM_006186 | NP_006177 |
| | M. musculus | NM_013613 | NP_038641 |
| | R. norvegicus | NM_019328 | NP_062201 |
| | B. taurus | NM_001076208 | NP_001069676 |
| | C. familiaris | XM_535920 | XP_535920 |
| | E. caballus | XM_001490494 | XP_001490544 |
| pitx3 | H. sapiens | NM_005029 | NP_005020 |
| | M. musculus | NM_008852 | NP_032878 |
| | R. norvegicus | NM_019247 | NP_062120 |
| | B. taurus | XM_589431 | XP_589431 |
| | C. familiaris | XM_543986 | XP_543986 |
| | E. caballus | XM_001499135 | XP_001499185 |
| lmx1a | H. sapiens | NM_177398.2; | NP_796372; |
| | | NM_177399.2; | NP_796373; |
| | | NM_001033507 | NP_001028679 |
| | M. musculus | NM_033652 | NP_387501 |
| | R. norvegicus | NM_001105967 | NP_001099437 |
| | B. taurus | XM_001789182 | XP_001789234 |
| | C. familiaris | XM_846259 | XP_851352 |
| | E. caballus | XM_001493329 | XP_001493379 |
| Shh | H. sapiens | NM_000193 | NP_000184 |
| | M. musculus | NM_009170 | NP_033196 |
| | R. norvegicus | NM_017221 | NP_058917 |
| | C. familiaris | XM_856335 | XP_861428 |
| | E. caballus | XM_001914885 | XP_001914920 |

The term "retinoic acid" refers to retinoic acid itself and any derivative thereof that can act as a lineage priming agent. Exemplary retinoic acid derivatives include, but are not limited to vitamin A, all-trans retinoic acid, and ester and ether derivatives thereof.

The term "forskolin" refers to the compound forskolin (IUPAC name (3R, 4aR,5S,6S,6aS,10S,10aR,10bS)-6,10, 10b-trihydroxy-3,4-a,7,7,10a-pentamethyl-1-oxo-3-vinyl-dodecahydro-1H-benzo[f]chromen-5-yl acetate) such as that obtained from Coleus forskohlii, and any derivative thereof that can act as a lineage priming agent. Other phosphodiesterase inhibitors besides forskolin can also be employed as lineage priming agents, including but not limited to papaverine, vinpocetine, sodium nitroprusside, milrinone, rolipram, zaprinast, and dipyridamole. Other agents that increase intracellular cAMP levels can also be employed.

As such, in some embodiments a recombinant dopaminergic neuron and/or a recombinant progenitor thereof comprises one or more transgenes encoding a nurr-1 polypeptide, a pitx3 polypeptide, a lmx1a polypeptide, a biologically active fragment thereof, a biologically active derivative thereof, and/or any combination thereof. In some embodiments, a recombinant dopaminergic neuron and/or a recombinant progenitor thereof comprises a single transgene that encodes two or more of a nurr-1 polypeptide, a pitx3 polypeptide, a lmx1a polypeptide, a biologically active fragment thereof, a biologically active derivative thereof, and/or any combination thereof. In some embodiments, a recombinant dopaminergic neuron or a recombinant progenitor thereof comprises a single transgene that encodes a nurr-1 polypeptide and a pitx3 polypeptide.

In some embodiments, a single transgene that encodes multiple polypeptides does so by encoding fusion proteins and/or by encoding the polypeptides on a complex transcription unit that is differentially translated to produce distinct polypeptides. In some embodiments, multiple polypeptides are encoded by a single transgene by employing one or more copies of a nucleotide sequence known as an "internal ribosome entry sites" (IRES). The use of IRES sequences to encode more than one distinct polypeptide on a single transcription unit is described in Zhou et al., 1990 and U.S. Pat. No. 5,648,235.

In some embodiments, a recombinant progenitor that can differentiate into a recombinant dopaminergic neuron comprises a dopaminergic lineage primed cell. The phrase "dopaminergic lineage primed cell" refers to a cell that in some embodiments has at least four of the following characteristics including characteristic (i); in some embodiments has at least five of the following characteristics including characteristic (i); in some embodiments has at least six of the following characteristics including characteristic (i); in some embodiments has at least seven of the following characteristics including characteristic (i); and in some embodiments has all of the following characteristics:

(i) expresses TH;
(ii) express dopamine;
(iii) expresses neurofilament 68 (NF68);
(iv) expresses neurofilament 160 (NF160);
(v) expresses neurofilament 200 (NF200);
(vi) expresses NeuN;
(vii) expresses Isl 1 and/or Isl 2 (Isl 1/2);
(viii) does not express VAChT or expresses VAChT in an amount of that is either undetectable or below that expressed in TH-negative neuronal cells;
(ix) does not express ChAT or expresses ChAT in an amount of that is either undetectable or below that expressed in TH-negative neuronal cells;
(x) does not express GFAP or expresses an amount of GFAP that is either undetectable or below that expressed in astrocytes;
(Xi) does not express GalC or expresses an amount of GalC that is either undetectable or below that expressed in oligodendrocyte cells;
(xii) does not express MBP or expresses an amount of MBP that is either undetectable or below that expressed in oligodendrocyte cells; and
(xiii) does not express OX42 or expresses an amount of OX42 that is either undetectable or below that expressed in microglial cells.

Dopaminergic lineage primed cells need not have all of the aforementioned characteristics, but will have at least four of these characteristics simultaneously, including in some embodiments characteristic (i).

Thus, in some embodiments a method for producing a recombinant dopaminergic neuron or recombinant progenitor thereof comprises (a) providing a human olfactory epithelial-derived stem cell (in some embodiments, a human olfactory epithelial-derived stem cell, and in some embodiments an adult human olfactory epithelial-derived stem cell), optionally a plurality of olfactory epithelial-derived stem cells, further optionally wherein the plurality of olfactory epithelial-derived stem cells are in the form of one or more neurospheres; (b) introducing into the olfactory epithelial-derived stem cell one or more transgenes encoding a nurr-1 polypeptide, a pitx3 polypeptide, a Imx1a polypeptide, a biologically active fragment thereof, a biologically active derivative thereof, and/or any combination thereof; and (c) culturing the olfactory epithelial-derived stem cell before, during, and/or after the introducing step in medium comprising a Sonic hedgehog (Shh) polypeptide, a biologically active fragment thereof, a derivative thereof, retinoic acid (RA) or a biologically active derivative thereof, forskolin (FN) or a biologically active derivative thereof, or any combination thereof, under conditions sufficient to induce neuronal differentiation in the olfactory epithelial-derived stem cell, whereby a recombinant dopaminergic neuron or recombinant progenitor thereof is produced. In some embodiments, the olfactory epithelial-derived stem cell is a human olfactory epithelial-derived stem cell and at least one of the nurr-1 polypeptide, the pitx3 polypeptide, the Imx1a polypeptide, the biologically active fragment thereof, the biologically active derivative thereof, and/or the combination thereof are derived from a species other than human. In some embodiments, the pitx3 polypeptide or the biologically active fragment or derivative thereof is a rat pitx polypeptide or a biologically active fragment or derivative thereof. In some embodiments, the Imx1a polypeptide or the biologically active fragment or derivative thereof is a mouse Imx1a polypeptide or a biologically active fragment or derivative thereof. In some embodiments, the nurr-1 polypeptide or the biologically active fragment or derivative thereof is a mouse nurr-1 polypeptide or a biologically active fragment or derivative thereof.

As such, the presently disclosed subject matter also provides methods for producing lineage primed cells. The phrase "lineage-restricted specification" refers to the commitment of a progenitor cell to form a non-progenitor cell type.

Lineage priming of NSFCs with conventional culture media conditions, such as 10% fetal bovine serum, occurs with an efficiency of less than 1%. By contrast, the efficiency of lineage priming of NSFCs with the lineage priming agents described in the presently disclosed subject matter is at least 1%. In some embodiments, the efficiency of lineage priming of NSFCs is at least 5%. In some embodiments, the efficiency of lineage priming is at least 10%. In some embodiments, the efficiency of lineage priming falls within the range from 5% to 95%, including 10%, 20%, 30%, 40%, 50%, 60%, 75%, and 90%. The efficiency of lineage priming can be determined in a number of ways, including using immunocytochemical analysis to determine the proportion of lineage primed cells of a particular type formed in an NSFC population treated with a lineage priming agent.

Lineage priming of NSFCs can result in mixed cell populations containing both NSFCs and one or more different types of lineage primed cells. For example, NSFCs, motoneuronal lineage primed cells, and dopaminergic lineage primed cells are present following treatment of NSFC cultures with 1 µM RA in combination with 5 µM FN and 15 nM Shh for seven days. Each of these cell populations display specific markers on the cell surfaces that distinguish lineage primed cell types from one another and from NSFCs, and this characteristic can be used in a method to select homogeneous cell populations of a particular type. One such method is the use of an antibody that recognizes as an antigen a specific lineage primed cell marker that is not expressed on other lineage primed cells of a different type or on NSFCs. The antibody can be immobilized onto a solid matrix, such as a resin or bead (e.g., a magnetic bead), and used to bind antigen-containing cells of a particular type (for example, NSFCs or specific lineage primed cell populations). Lineage primed cells that lack the antigen are separated from the antigen-containing lineage primed cells by recovering the solid matrix containing the antibody-bound cells and washing away the unbound cells. Dopaminergic linear primed cells, for example, can be selected from a mixed population containing NSFCs as well as motoneuronal and dopaminergic lineage primed cells using an antibody specific for an antigen expressed specifically by dopaminergic lineage primed cells (for example, TH). These techniques can be adapted to select NSFCs from the original cultures containing olfactory epithelium and to recover NSFCs following a lineage priming treatment. Examples of such selection techniques are described by Othman et al. 2005(a) and Othman et al. 2005(b).

The phrase "lineage priming" refers to any action that induces a progenitor cell to undergo lineage-restricted specification.

The phrase "lineage primed cells" refers to cells that originate from a progenitor cell as a result of lineage priming.

The term "efficiency" refers to the proportion of non-progenitor cells formed from progenitor cells as a result of lineage priming. An example of one method for determining the efficiency of lineage priming is to use immunohistochemistry to visualize a marker associated with only a non-progenitor cell and to count the number of cells having that marker and the number of total cells in the representative population. The efficiency, expressed as a percentage, would be the ratio of cells having the marker to the total cell population, multiplied by one hundred.

A "cell-restricted lineage pathway" refers to cell states of non-progenitor cells that belong to a common pathway of specification that can lead to a terminally differentiated cell.

In some embodiments, the methods for producing lineage primed cells thus comprise (a) culturing the olfactory epithelial-derived stem cell (in some embodiments, a human olfactory epithelial-derived stem cell and in some embodiments an adult human olfactory epithelial-derived stem cell) in medium comprising of a Sonic hedgehog (Shh) polypeptide, a biologically active fragment thereof, a derivative thereof, retinoic acid (RA) or a biologically active derivative thereof, forskolin (FN) or a biologically active derivative thereof, or any combination thereof, under conditions sufficient to induce neuronal differentiation in the olfactory epithelial-derived stem cell; and (b) expressing in the recombinant olfactory epithelial-derived stem cell one or more transgenes encoding a nurr-1 polypeptide, a pitx3 polypeptide, a Imx1a polypeptide, a biologically active fragment thereof, a biologically active derivative thereof, and/or any combination thereof, whereby a lineage primed cell comprising a recombinant dopaminergic neuron or recombinant progenitor thereof is produced. In some embodiments, the one or more of the nurr-1 polypeptide, the pitx3 polypeptide, the Imx1a polypeptide, the biologically active fragment thereof, the biologically active derivative thereof, and/or the combination thereof encoded by the one or more transgenes comprises a mouse ortholog, a rat ortholog, and/or a human ortholog, a biologically active fragment thereof, a biologically active derivative thereof, or any combination thereof.

As such, lineage priming of NSFCs along neuronal cell-restricted lineage pathways can be employed to produce several non-progenitor CNS cell types, including dopaminergic lineage primed cells or motoneuronal lineage primed cells. Combinations of lineage priming agents can be used for lineage priming of the NSFC cultures and include the following robust regimens: (1) incubation of NSFCs in medium containing RA combined with FN and/or Shh; and (2) directed expression of a nurr-1 gene product, a pitx3 gene product, and/or a lmx1a gene product, in NSFC transfectants. These regimens have utility in establishing CNS cell types having a morphologic and lineage-restricted phenotype. Such cellular materials are useful for replacement cellular therapy strategies for patients suffering from degenerative CNS diseases.

The cells of the presently disclosed subject matter can be used to manufacture pharmaceutically useful compounds, such as dopamine or other neurotransmitters produced by healthy neurons. In some embodiments, a NSFC per se produces one or more pharmaceutically useful compounds such as, but not limited to NGF, BDNF, NT3, NT4/5, and/or VEGF. Alternatively or in addition, by directing a cell of the presently disclosed subject matter down a differentiation pathway leading to neuron formation, a unique cell culture comprised of differentiated neurons derived from the stem cell of the presently disclosed subject matter can provide large cell populations capable of producing large amounts of pharmaceutically useful compounds, such as dopamine. Further, many growth factors, including at least NGF, BDNF, NT3, and NT4/5 can be used to induce the presently disclosed cells to undergo additional differentiation.

Second messengers, such as cAMP, can be used to mediate the interaction between the growth factor receptors of the differentiating stem cell and the growth factors themselves. For example, exposure of neurosphere subcultures to media containing 2.5 mM dibutyryl cAMP drastically decreases mitotic activity and increases in the levels of α-internexin, a neuronal (intermediate filament) marker that appears prior to neurofilament formation in developing neurons.

Additionally, the cells of the presently disclosed subject matter can be manipulated to express transgenes that encode useful products. An advantage of engineering the cells of the presently disclosed subject matter, whether differentiated or not, is the possibility of producing polypeptides, such as neuronal polypeptides or stem-cell specific polypeptides that are processed in a manner that they would be in their native context and can thus be cultured in large quantities. Another advantage includes the engineering of such cells prior to transplantation to a subject such that a therapeutically useful molecule is expressed. For example, a patient suffering from Parkinson's disease can have olfactory epithelium cells harvested to isolate the stem cells of the presently disclosed subject matter, but they might not express sufficient dopamine to treat Parkinson's disease. Thus, such cells can be engineered with a wild-type dopamine gene (either operably-linked to the endogenous dopamine promoters or to an exogenous promoter, depending on the regulation and quantity of secretion that is desired) before implantation. In some embodiments, the olfactory epithelial-derived stem cells are autologous, meaning that they were harvested from the patient him- or herself and/or from another autologous source.

IV. Methods and Compositions for Treatment Using Olfactory Epithelial-derived Stem Cell Subpopulations The cells of the presently disclosed subject matter can further be used to form, reform, and/or rescue damaged or malfunctioning CNS structures, such as axons and/or to encourage regrowth of existing axons. For example, the cells can be differentiated, and the resulting ensheathing cells selected and transplanted to repair neurological damage.

The differentiation of stem cells can be directed to result in a particular type of daughter cell arising from the parent stem cell. For example when the stem cell of the present invention is exposed to dibutyryl cAMP for 24 hours, it differentiates into a progenitor containing a neurofilament precursor.

Furthermore, in culture, at least a portion of the cells spontaneously differentiate and can be selected. Freezing can be used to store the differentiated cells until enough are collected for an effective transplantation. Therefore, by inducing the stem cell of the presently disclosed subject matter to form a desired cell type, and injecting this differentiated cell into the site of injury, CNS structures can be treated.

IV.A. Transplantation

Thus, the presently disclosed subject matter also provides methods for transplantation comprising transplanting into a subject a dopaminergic lineage primed olfactory epithelial-derived stem cell (in some embodiments, a human olfactory epithelial-derived stem cell, and in some embodiments an adult human olfactory epithelial-derived stem cell) or a progenitor thereof, wherein the dopaminergic lineage primed olfactory epithelial-derived stem cell expresses one or more transgenes that (a) encode one or more of a nurr-1 polypeptide, a pitx3 polypeptide, an lmx1a polypeptide, a biologically active fragment thereof, and a biologically active derivative thereof; and/or (b) comprise a promoter that is transcriptionally active in the dopaminergic neuron or a progenitor thereof that is operably-linked to a coding sequence encoding the nurr-1 polypeptide, the pitx3 polypeptide, the lmx1a polypeptide, or the biologically active fragment or derivative thereof, and further wherein the lineage priming has an efficiency of at least 1%. In some embodiments, the lineage priming has an efficiency of at least 5%, 10%, 15%, 20%, or more. In some embodiments, the lineage priming comprises (a) providing an olfactory epithelial-derived stem cell (in some embodiments, a human olfactory epithelial-derived stem cell, and in some embodiments an adult human olfactory epithelial-derived stem cell), optionally a plurality of olfactory epithelial-derived stem cells, further optionally in the form of one or more neurospheres; (b) introducing into the olfactory epithelial-derived stem cell one or more transgenes encoding a polypeptide selected from the group consisting of a nurr-1 polypeptide, a pitx3 polypeptide, a lmx1a polypeptide, a biologically active fragment thereof, a biologically active derivative thereof, and/or any combination thereof; and (c) culturing the olfactory epithelial-derived stem cell before, during, and/or after the introducing step in medium comprising of a Sonic hedgehog (Shh) polypeptide, a biologically active fragment thereof, a derivative thereof, retinoic acid (RA) or a biologically active derivative thereof, forskolin (FN) or a biologically active derivative thereof, or any combination thereof, under conditions sufficient to induce neuronal differentiation in the olfactory epithelial-derived stem cell. In some embodiments, the conditions sufficient to induce neuronal differentiation comprise culturing the olfactory epithelial-derived stem cell in a culture medium comprising about 1 μM retinoic acid, about 5 μM forskolin, and about 15 nM Sonic hedgehog for at least about 3, 4, 5, 6, or 7 days. In some embodiments, the culturing step produces a dopaminergic neuron or a recombinant progenitor thereof that expresses an endogenous tyrosine hydroxylase (TH) gene product, produces dopamine, secretes dopamine, or combinations thereof.

IV.B. Methods for Ameliorating Symptoms Associated with Neurological Disorders

The presently disclosed subject matter also provides methods for ameliorating at least one symptom associated with a neurological disorder in a subject. As used herein, the phrase "symptom associated with a neurological disorder in a subject" refers to any symptom that exists in a subject that has a neurological disorder that results directly or indirectly from abnormal or suboptimal functioning of the nervous system of the subject. In some embodiments, the symptom associated with a neurological disorder in a subject results from damage to one or more cell types of the nervous system of the subject caused by a genetic defect in the subject, an acute injury to the subject, and/or exposure of the subject to one or more environmental insults.

In some embodiments, the methods providing a dopaminergic neuron expressing one or more of a nurr-1 polypeptide, a pitx3 polypeptide, an Imx1a polypeptide, a biologically active fragment or derivative thereof or a progenitor thereof, and transplanting the recombinant dopaminergic neuron or the progenitor thereof into the subject, optionally into the substantia nigra of the subject. In some embodiments, the neurological disorder is Parkinson's disease.

In some embodiments, the transplanted recombinant dopaminergic neuron or progenitor thereof (in some embodiments, a recombinant progenitor thereof) induces growth and/or regeneration of one or more endogenous stem cells and/or neurons in the subject. As used herein, the phrase "growth and/or regeneration of one or more endogenous stems cells and/or neurons in the subject" refers to growth and or regeneration of one of the subject's own stem cells and/or neurons (i.e., a non-recombinant stem cell and/or neuron that is already present in the subject when the recombinant dopaminergic neuron or the recombinant progenitor is transplanted into the subject). While it is not desired to be limited to any particular theory of operation, the recombinant dopaminergic neurons or recombinant progenitors thereof of the presently disclosed subject matter secrete various neurotrophic factors that can aid in the growth, repair, and/or regeneration of a subject's own neurons by acting on those neurons and/or endogenous progenitors thereof.

IV.C. Methods for Inducing Growth and/or Regeneration of Neurons

The presently disclosed subject matter also provides methods for inducing growth and/or regeneration of a neuron in a subject. In some embodiments, the methods comprise transplanting a plurality of olfactory epithelial-derived stem cells and/or differentiated derivatives thereof into the subject at a location and in a number sufficient to induce growth and/or regeneration of a neuron in the subject. The olfactory epithelial-derived stem cells (in some embodiments, human olfactory epithelial-derived stem cells, and in some embodiments adult human olfactory epithelial-derived stem cells) and/or the differentiated derivatives thereof can be transplanted into any target tissue. In some embodiments, the olfactory epithelial-derived stem cells and/or differentiated derivatives thereof are transplanted into a central nervous system site is the subject including, but not limited to the substantia nigra. In some embodiments, the subject has a neurological disorder associated with loss of dopaminergic neurons, optionally wherein the neurological disorder is Parkinson's disease.

The presently disclosed methods can also include a step of differentiating the olfactory epithelial-derived stem cell in vitro prior to transplantation by expressing in the olfactory epithelial-derived stem cell one or more transgenes encoding a lineage priming agent including, but not limited to a polypeptide selected from the group consisting of a nurr-1 polypeptide, a pitx3 polypeptide, a Imx1a polypeptide, a biologically active fragment thereof, a biologically active derivative thereof, and/or any combination thereof. A listing of mammalian orthologs for these lineage priming agents is presented in Table 1. In some embodiments, the nurr-1 polypeptide, the pitx3 polypeptide, and/or the Imx1a polypeptide is a human ortholog thereof. In some embodiments, the transplanting provides to the neuron an effective amount of a neurotrophic factor (e.g., BDNF, NGF, CTNF, NT-3, NT-4, or VEGF) sufficient to provide cause the neuron to grow and/or regenerate.

IV.D. Methods for Delivering Neurotrophic Factors to Subjects

The presently disclosed subject matter also provides methods for delivering a neurotrophic factor to a subject, including but not limited to delivering the neurotrophic factor directly to the central nervous system of the subject and thus avoiding the Blood-Brain Barrier.

By way of example and not limited, the presently disclosed methods can comprise delivering brain-derived neurotrophic factor (BDNF) to the central nervous system of a subject. In some embodiments, the methods comprise transplanting into the subject an olfactory epithelial-derived stem cell or a differentiated derivative thereof, wherein the transplanting is into a central nervous system site in the subject. As disclosed herein, olfactory epithelial-derived stem cells and differentiated derivatives thereof produce and secrete various neurotrophic factors including, but not limited to BDNF.

The provision of such neurotrophic factors can aid in the restoration of a functional deficit in the subject. For example, neurological injuries are known to result in functional deficits, and the presently disclosed subject matter can be employed to improve functional deficits that result from such injuries.

IV.E. Methods for Providing Dopaminergic Neurons to Subjects

The presently disclosed subject matter also provides methods for providing a dopaminergic neuron function to a subject in need thereof. As used herein, the phrase "a dopaminergic neuron function" refers to any function normally provided by dopaminergic neurons in a subject. An exemplary dopaminergic neuron function is the production and delivery of dopamine. In some embodiments, the dopaminergic neuron function is a function normally provided by dopaminergic neurons ins a human subject.

In some embodiments, the methods comprise introducing a plurality of olfactory epithelial-derived stem cells and/or in vitro differentiated derivatives thereof into the midbrain of the subject in a number and under conditions sufficient to allow at least one of the plurality of olfactory epithelial-derived stem cells (in some embodiments, human olfactory epithelial-derived stem cells, and in some embodiments adult human olfactory epithelial-derived stem cells) to differentiate into a functional dopaminergic neuron, thereby providing a dopaminergic neuron function to a subject. Alternatively or in addition, the in vitro differentiated derivatives can be differentiated by expressing in at least one olfactory epithelial-derived stem cell one or more transgenes encoding a polypeptide selected from the group consisting of a nurr-1 polypeptide, a pitx3 polypeptide, an Imx1a polypeptide, a biologically active fragment thereof, a biologically active derivative thereof, and/or any combination thereof, and/or by exposing at least one olfactory epithelial-derived stem cell to a neurotrophic factor that induces differentiation of the olfactory epithelial-derived stem cell to a dopaminergic neuron and/or that primes the olfactory epithelial-derived stem cell to differentiate into a dopaminergic neuron.

In the presently disclosed methods, it is possible for the introduced olfactory epithelial-derived stem cells and/or in vitro differentiated derivatives thereof to themselves differentiate into dopaminergic neurons and/or to induce the subject's own (i.e., the subject's endogenous) cells to differentiate into dopaminergic neurons. As such, in some embodiments the introduced olfactory epithelial-derived stem cells and/or in vitro differentiated derivatives thereof terminally differentiate into one or more functional dopaminergic neurons in the subject. Alternatively or in addition, the introducing can induce one or more endogenous cells in the subject to differentiate into one or more functional dopaminergic neurons, can induce repair of a non-functional or suboptimally functional endogenous dopaminergic neuron or a precursor thereof in the subject, and/or can rescue a dopaminergic neuron and/or a precursor thereof from inactivation and/or death that it would have undergone in the absence of the introduced plurality of olfactory epithelial-derived stem cells and/or in vitro differentiated derivatives thereof.

IV.F. Subjects

In some embodiments, the presently disclosed subject matter is intended to be employed in a subject. The term "subject" as used herein refers to a member of any invertebrate or vertebrate species. Accordingly, the term "subject" is intended to encompass any member of the Kingdom Animalia including, but not limited to the phylum Chordata (i.e., members of Classes Osteichythyes (bony fish), Amphibia (amphibians), Reptilia (reptiles), Ayes (birds), and Mammalia (mammals)), and all Orders and Families encompassed therein. In some embodiments, a subject is a mammal, and in some embodiments a subject is a human.

Similarly, all genes, gene names, and gene products disclosed herein are intended to correspond to homologs and orthologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes disclosed herein, which in some embodiments relate to human nucleic acid and amino acid sequences by GENBANK® Accession No., are intended to encompass homologous and orthologous genes and gene products from other animals including, but not limited to other mammals, fish, amphibians, reptiles, and birds.

The methods of the presently disclosed subject matter are particularly useful for warm-blooded vertebrates. Thus, in some embodiments the presently disclosed subject matter concerns mammals and birds. More particularly contemplated is the isolation, manipulation, and use of olfactory epithelial-derived stem cells from mammals such as humans and other primates, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), rodents (such as mice, rats, and rabbits), marsupials, and horses. Also provided is the use of the disclosed methods and compositions on birds, including those kinds of birds that are endangered, kept in zoos, as well as fowl, and more particularly domesticated fowl, e.g., poultry, such as turkeys, chickens, ducks, geese, guinea fowl, and the like, as they are also of economic importance to humans. Thus, the isolation, manipulation, and use of olfactory epithelial-derived stem cells from livestock, including but not limited to domesticated swine (pigs and hogs), ruminants, horses, poultry, and the like, are also encompassed by the presently disclosed subject matter.

IV.G. Formulations

The compositions of the presently disclosed subject matter comprise in some embodiments a composition that includes a carrier, particularly a pharmaceutically acceptable carrier, such as but not limited to a carrier pharmaceutically acceptable in humans. Any suitable pharmaceutical formulation can be used to prepare the compositions for administration to a subject.

For example, suitable formulations can include aqueous and non-aqueous sterile injection solutions that can contain anti-oxidants, buffers, bacteriostatics, bactericidal antibiotics, and solutes that render the formulation isotonic with the bodily fluids of the intended recipient.

It should be understood that in addition to the ingredients particularly mentioned above the formulations of the presently disclosed subject matter can include other agents conventional in the art with regard to the type of formulation in question. For example, sterile pyrogen-free aqueous and non-aqueous solutions can be used.

The therapeutic regimens and compositions of the presently disclosed subject matter can be used with additional adjuvants or biological response modifiers including, but not limited to, cytokines and other immunomodulating compounds.

IV.H. Administration

The stem cells of the present invention can be transplanted into a patient suffering from a neurological disorder, such as a neurological injury, Alzheimer's disease, Parkinson's disease, amyotrophic lateral sclerosis, or multiple sclerosis, as a method for treating the disorder (e.g., ameliorating at least one symptom associated with the disorder). Methods of transplantation include injection of transformed or cells effective for treating a neurological disorder, via a variety of methods, at the site of injury or a distant site. The cells can be partial or completely differentiated prior to transplantation.

Thus, suitable methods for administration the cells of the presently disclosed subject matter include, but are not limited to delivery directly to the target tissue and delivery to a site that permits neurotrophic factors produced by the cells of the presently disclosed subject matter to reach the target tissue. In some embodiments, the method for administration encompasses features for regionalized delivery or accumulation of the cells at the site in need of treatment. In some embodiments, the cells are delivered directly into the tissue to be treated.

IV.I. Dose

An effective dose of a composition of the presently disclosed subject matter is administered to a subject in need thereof. A "treatment effective amount" or a "therapeutic amount" is an amount of a therapeutic composition sufficient to produce a measurable response (e.g., a biologically or clinically relevant response in a subject being treated). Actual dosage levels of the cells in the compositions of the presently disclosed subject matter can be varied so as to administer an amount of a cell and/or a neurotrophic factor that is effective to achieve the desired biologically or clinically relevant response for a particular subject. The selected dosage level will depend upon the activity of the composition, the route of administration, combination with other drugs or treatments, the severity of the condition being treated, and the condition and prior medical history of the subject being treated. However, it is within the skill of the art to start doses of the cells at levels lower than required to achieve the desired biologically or clinically relevant response and to gradually increase the dosage until the desired response is achieved. The potency of a composition can vary, and therefore a "treatment effective amount" can vary. However, one skilled in the art can readily assess the potency and efficacy of a candidate compound of the presently disclosed subject matter and adjust the therapeutic regimen accordingly.

After review of the disclosure of the presently disclosed subject matter presented herein, one of ordinary skill in the art can tailor the dosages to an individual subject, taking into account the particular formulation, method of administration to be used with the composition, and particular disease treated. Further calculations of dose can consider subject height and weight, severity and stage of symptoms, and the presence of additional deleterious physical conditions. Such adjustments or variations, as well as evaluation of when and how to make such adjustments or variations, are well known to those of ordinary skill in the art of medicine.

V. Nucleic Acids and Polypeptides

An aspect of the presently disclosed subject matter pertains to isolated nucleic acid molecules that encode Sonic hedgehog, nurr-1, pitx3, and/or Imx1a gene products, or biologically-active portions thereof. Also included in the presently disclosed subject matter are nucleic acid fragments sufficient for use as hybridization probes to identify Sonic hedgehog-, nurr-1-, pitx3-, and/or Imx1a-encoding nucleic acids (for example, Sonic hedgehog, nurr-1, pitx3, and Imx1a mRNAs) and fragments for use as polymerase chain reaction (PCR) primers for the amplification and/or mutation of Sonic hedgehog, nurr-1, pitx3, and/or Imx1a molecules. A "nucleic acid molecule" includes DNA molecules (for example, cDNA or genomic DNA), RNA molecules (for example, mRNA), analogs of the DNA or RNA generated using nucleotide analogs, and derivatives, fragments, orthologs and homologs. The nucleic acid molecule can be single-stranded or double-stranded.

V.A. Probes

Probes are nucleic acid sequences of variable length (e.g., at least about 10 nucleotides (nt), at least about 20 nt, at least about 50 nt, at least about 100 nt, or in some embodiments 200 nt or more) depending on the specific intended use. Probes can be used to detect identical, similar, or complementary nucleic acid sequences. Longer length probes can be obtained from a natural or recombinant source, are highly specific, and much slower to hybridize than shorter-length oligomer probes. Probes can be single or double stranded and designed to have specificity in PCR, membrane-based hybridization technologies, or ELISA-like technologies. Probes can be substantially purified oligonucleotides that hybridize under stringent conditions to at least 12, 25, 50, 100, 150, 200, 250, 300, 350 or 400 consecutive sense strand nucleotide sequence of a Sonic hedgehog, nurr-1, pitx3, and/or Imx1a gene product, or an anti-sense strand nucleotide sequence of these sequences; or of a naturally occurring mutant of these sequences.

The full or partial length native sequence for example can be used to identify and isolate similar (homologous and/or orthologous) sequences (Sambrook & Russell, 2001; Ausubel et al., 2002; Ausubel et al., 2003), such as: (1) full length or fragments of a Sonic hedgehog, nurr-1, pitx3, and/or Imx1a cDNA from a cDNA library from any species (for example, human, murine, feline, canine, fish, bird, and frog), (2) from cells or tissues, (3) variants within a species, and (4) homologues and variants from other species. To find related sequences that can encode related genes, the probe can be designed to encode unique sequences or degenerate sequences. Sequences can also be genomic sequences including promoters, enhancer elements, and introns of native sequence for a Sonic hedgehog, nurr-1, pitx3, and/or Imx1a gene products.

For example, a Sonic hedgehog, nurr-1, pitx3, and/or Imx1a coding region in another species can be isolated using such probes. A probe of about 40 bases can be designed and produced based on a nucleotide sequence of a Sonic hedgehog, nurr-1, pitx3, and/or Imx1a gene product. To detect hybridizations, probes can be labeled using, for example, radionuclides such as $^{32}P$ or $^{35}S$, or enzymatic labels such as alkaline phosphatase coupled to the probe via avidin-biotin systems. Labeled probes can be used to detect nucleic acids having a complementary sequence to that of a Sonic hedgehog, nurr-1, pitx3, and/or Imx1a gene sequences in libraries of cDNA, genomic DNA or mRNA of a desired species.

Such probes can be used as a part of a diagnostic test kit for identifying cells or tissues which mis-express a Sonic hedgehog, nurr-1, pitx3, and/or Imx1a gene product, such as by measuring a level of an a Sonic hedgehog, nurr-1, pitx3, and/or Imx1a gene product in a sample of cells from a subject for example, detecting a Sonic hedgehog, nurr-1, pitx3, and/ or Imx1a mRNA levels, or determining whether a genomic a Sonic hedgehog, nurr-1, pitx3, and/or Imx1a gene sequence has been mutated or deleted.

V.B. Isolated Nucleic Acid

An isolated nucleic acid molecule can be separated from other nucleic acid molecules that are present in the natural source of the nucleic acid. In some embodiments, an isolated nucleic acid is free of sequences that naturally flank the nucleic acid (that is, sequences located at the 5'- and 3'-termini of the nucleic acid) in the genomic DNA of the organism from which the nucleic acid is derived. For example, in some embodiments, isolated a Sonic hedgehog, nurr-1, pitx3, and/ or Imx1a gene products can contain less than about 5 kb, 4 kb, 3 kb, 2 kb, 1 kb, 0.5 kb, or 0.1 kb of nucleotide sequences which naturally flank the nucleic acid molecule in genomic DNA of the cell/tissue from which the nucleic acid is derived (for example, brain, heart, liver, spleen, etc.). Moreover, an isolated nucleic acid molecule, such as a cDNA molecule, can be substantially free of other cellular material or culture medium when produced by recombinant techniques, or of chemical precursors or other chemicals when chemically synthesized.

PCR amplification techniques can be used to amplify a Sonic hedgehog, nurr-1, pitx3, and/or Imx1a gene product using cDNA, mRNA or alternatively, genomic DNA, as a template and appropriate oligonucleotide primers. Such nucleic acids can be cloned into an appropriate vector and characterized by DNA sequence analysis. Furthermore, oligonucleotides corresponding to a Sonic hedgehog, nurr-1, pitx3, and/or Imx1a gene product sequences can be prepared by standard synthetic techniques, for example, an automated DNA synthesizer.

V.C. Oligonucleotides

An oligonucleotide comprises a series of linked nucleotide residues, which oligonucleotide has a sufficient number of nucleotide bases to be used in a PCR reaction or other application. A short oligonucleotide sequence can be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid sequence having about 10 nt, 50 nt, or 100 nt in length, in some embodiments about 15 nt to 30 nt in length. In some embodiments of the presently disclosed subject matter, an oligonucleotide comprising a nucleic acid molecule less than 100 nt in length can further comprise at least 6 contiguous nucleotides of a Sonic hedgehog, nurr-1, pitx3, and/or lmx1a gene product, or a complement thereof. Oligonucleotides can be chemically synthesized and can also be used as probes.

V.D. Complementary Nucleic Acid Sequences: Binding

In some embodiments, an isolated nucleic acid molecule for use with the invention comprises a nucleic acid molecule that is a complement of the nucleotide sequence of a Sonic hedgehog, nurr-1, pitx3, and/or lmx1a gene product or a portion of such nucleotide sequence (for example, a fragment that can be used as a probe or primer or a fragment encoding a biologically-active portion of an Olig2, HB9, Ngn2, SoxW, or Nkx2.2). A nucleic acid molecule that is complementary to the nucleotide sequence of a human a Sonic hedgehog, nurr-1, pitx3, and/or lmx1a gene product is one that is sufficiently complementary to the nucleotide sequence that it can hydrogen bond with little or no mismatches to the desired nucleotide sequence, thereby forming a stable duplex.

As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Binding includes ionic, non-ionic, van der Waals, hydrophobic interactions, and the like. A physical interaction can be either direct or indirect. Indirect interactions can be through or due to the effects of another polypeptide or compound. Direct binding refers to interactions that do not take place through, or due to, the effect of another polypeptide or compound, but instead are without other substantial chemical intermediates.

Nucleic acid fragments are at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence. Fragments can be derived from any contiguous portion of a nucleic acid or amino acid sequence of choice.

V.E. Derivatives and Analogs

Derivatives are nucleic acid sequences or amino acid sequences formed from the native compounds either directly or by modification or partial substitution. Analogs are nucleic acid sequences or amino acid sequences that have a structure similar to, but not identical to, the native compound but differ from it in respect to certain components or side chains. Analogs can be synthetic or from a different evolutionary origin and can have a similar or opposite metabolic activity compared to wild type. Homologs are nucleic acid sequences or amino acid sequences of a particular gene that are derived from different species.

Derivatives and analogs can be full length or other than full length, if the derivative or analog contains a modified nucleic acid or amino acid, as described below. Derivatives or analogs of the nucleic acids or proteins of the invention include molecules comprising regions that are substantially homologous to the nucleic acids or proteins of the presently disclosed subject matter, in some embodiments, by at least about 80%, 85%, 90%, 91%, 92%, 93%, 94%, 95%, 96%, 97%, 98%, or 99% identity over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions (Ausubel et al., 2002; Ausubel et al., 2003).

V.F. Homology

A "homologous nucleic acid sequence" or "homologous amino acid sequence", or variations thereof, refer to sequences characterized by homology at the nucleotide level or amino acid level as discussed above. Homologous nucleotide sequences encode those sequences coding for isoforms of a Sonic hedgehog, nurr-1, pitx3, and/or lmx1a gene products. Isoforms can be expressed in different tissues of the same organism as a result of, for example, alternative splicing of RNA. Alternatively, different genes can encode isoforms. Homologous nucleotide sequences include nucleotide sequences encoding for a Sonic hedgehog, nurr-1, pitx3, and/or lmx1a gene product of species other than humans, including vertebrates, and thus can include, for example, frog, mouse, rat, rabbit, dog, cat, cow, horse, fish, bird, and other organisms (also referred to herein as "orthologous" and grammatical variants thereof). Homologous nucleotide sequences also include, but are not limited to, naturally occurring allelic variations and mutations of the nucleotide sequences set forth herein. A homologous nucleotide sequence does not, however, include the exact nucleotide sequence encoding a Sonic hedgehog, nurr-1, pitx3, and/or lmx1a gene product. Homologous nucleic acid sequences include those nucleic acid sequences that encode conservative amino acid substitutions (see below) within a Sonic hedgehog, nurr-1, pitx3, and/or lmx1a gene product, as well as a polypeptide possessing a Sonic hedgehog, nurr-1, pitx3, and/or lmx1a biological activity as a lineage priming agent.

V.G. Open Reading Frames

The open reading frame (ORF) of a Sonic hedgehog, nurr-1, pitx3, and/or lmx1a gene product encodes an a Sonic hedgehog, nurr-1, pitx3, and/or lmx1a gene product. An ORF is a nucleotide sequence that has a start codon (ATG) and terminates with a "stop" codon (TAA, TAG, or TGA). With respect to the presently disclosed subject matter, however, an ORF can be any part of a coding sequence that does or does not comprise a start codon and a stop codon. To achieve a unique sequence, exemplary a Sonic hedgehog, nurr-1, pitx3, and/or lmx1a ORFs encode at least 50 amino acids.

V.H. Polypeptides

V.H.1. Mature

A Sonic hedgehog, nurr-1, pitx3, and/or lmx1a gene product can encode a mature a Sonic hedgehog, nurr-1, pitx3, and/or lmx1a polypeptide. A "mature" form of a polypeptide or protein disclosed herein is the product of a naturally occurring polypeptide or precursor form or proprotein. The naturally occurring polypeptide, precursor, or proprotein includes, for example, the full length gene product, encoded by the corresponding gene. Alternatively, it can be defined as the polypeptide, precursor or proprotein encoded by an open reading frame described herein. The product "mature" form arises, for example, as a result of one or more naturally occurring processing steps as they can take place within the cell, or host cell, in which the gene product arises. Examples of such processing steps leading to a "mature" form of a polypeptide or protein include the cleavage of the N-terminal methionine residue encoded by the initiation codon of an open reading frame, or the proteolytic cleavage of a signal peptide or leader sequence.

Thus, a mature form arising from a precursor polypeptide or protein that has residues 1 to N, where residue 1 is the N-terminal methionine, would have residues 2 through N remaining after removal of the N-terminal methionine. Alternatively, a mature form arising from a precursor polypeptide or protein having residues 1 to N, in which an N-terminal signal sequence from residue 1 to residue M is cleaved, would have the residues from residue M+1 to residue N remaining. Further as used herein, a "mature" form of a polypeptide or protein can arise from post-translational modification other than a proteolytic cleavage event. Such additional processes include, for example, glycosylation, myristoylation or phosphorylation. In general, a mature polypeptide or protein can result from the operation of only one of these processes, or a combination of any of them.

V.H.2. Active

An active Sonic hedgehog, nurr-1, pitx3, and/or Imx1a polypeptide or Sonic hedgehog, nurr-1, pitx3, and/or Imx1a polypeptide fragment retains a biological and/or an immunological activity similar, but not necessarily identical, to a lineage priming activity of a naturally-occurring (wild type) Sonic hedgehog, nurr-1, pitx3, and/or Imx1a polypeptide of the presently disclosed subject matter, including mature forms. A particular biological assay, such as lineage priming, with or without dose dependency, can be used to determine Sonic hedgehog, nurr-1, pitx3, and/or Imx1a activity. A nucleic acid fragment encoding a biologically-active portion of a Sonic hedgehog, nurr-1, pitx3, and/or Imx1a gene product can be prepared by isolating a portion of the corresponding gene encodes a polypeptide having a Sonic hedgehog, nurr-1, pitx3, and/or Imx1a gene product biological activity expressing the encoded portion of the Sonic hedgehog, nurr-1, pitx3, and/or Imx1a gene product (for example, by recombinant expression in vitro) and assessing the lineage priming activity of the encoded portion of the Sonic hedgehog, nurr-1, pitx3, and/or Imx1a gene product. Immunological activity refers to the ability to induce the production of an antibody against an antigenic epitope possessed by a native Sonic hedgehog, nurr-1, pitx3, and/or Imx1a gene product; biological activity refers to a function, either inhibitory or stimulatory, caused by a native Sonic hedgehog, nurr-1, pitx3, and/or Imx1a gene product that excludes immunological activity.

V.I. Nucleic Acid Variants and Hybridization

V.I.1. Variant Polynucleotides, Genes, and Recombinant Genes

The presently disclosed subject matter further encompasses nucleic acid molecules that differ from the nucleotide sequences encoded by the Sonic hedgehog, nurr-1, pitx3, and/or Imx1a gene products disclosed herein due to degeneracy of the genetic code, and thus encode the same Sonic hedgehog, nurr-1, pitx3, and/or Imx1a gene products.

In addition to the endogenous Sonic hedgehog, nurr-1, pitx3, and/or Imx1a sequences, DNA sequence polymorphisms that change the amino acid sequences of the Sonic hedgehog, nurr-1, pitx3, and/or Imx1a gene products can exist within a population. For example, allelic variation among individuals can exhibit genetic polymorphism in a Sonic hedgehog, nurr-1, pitx3, and/or Imx1a gene product. The terms "gene" and "recombinant gene" refer to nucleic acid molecules comprising an open reading frame (ORF) encoding a Sonic hedgehog, nurr-1, pitx3, and/or Imx1a gene product, in some embodiments a vertebrate Sonic hedgehog, nurr-1, pitx3, and/or Imx1a gene product. Such natural allelic variations can typically result in 1-5% variance in a Sonic hedgehog, nurr-1, pitx3, and/or Imx1a gene product. Any and all such nucleotide variations and resulting amino acid polymorphisms in a Sonic hedgehog, nurr-1, pitx3, and/or Imx1a gene product, which are the result of natural allelic variation and that do not alter the functional activity of a Sonic hedgehog, nurr-1, pitx3, and/or Imx1a gene product are within the scope of the invention.

Moreover, Sonic hedgehog, nurr-1, pitx3, and/or Imx1a gene products from other species that have a nucleotide sequence that differs from a sequence as disclosed in Table 1 are contemplated. Nucleic acid molecules corresponding to natural allelic variants and homologues of an Sonic hedgehog, nurr-1, pitx3, and/or Imx1a cDNAs of the presently disclosed subject matter can be isolated based on their homology to a Sonic hedgehog, nurr-1, pitx3, and/or Imx1a gene product using cDNA-derived probes to hybridize to homologous and/or orthologous Sonic hedgehog, nurr-1, pitx3, and/or Imx1a sequences under stringent conditions.

The phrase "Sonic hedgehog, nurr-1, pitx3, and/or Imx1a variant polynucleotide" or "Sonic hedgehog, nurr-1, pitx3, and/or Imx1a variant nucleic acid sequence" refers to nucleic acid molecules that encodes a active Sonic hedgehog, nurr-1, pitx3, and/or Imx1a gene products that (1) have at least about 80% nucleic acid sequence identity with a nucleotide acid sequence encoding a full length native Sonic hedgehog, nurr-1, pitx3, and/or Imx1a gene product; (2) full length native Sonic hedgehog, nurr-1, pitx3, and/or Imx1a gene product lacking the signal peptide; (3) extracellular domains of a Sonic hedgehog, nurr-1, pitx3, and/or Imx1a gene product, with or without the signal peptide; and/or (4) any other fragments of full length Sonic hedgehog, nurr-1, pitx3, and/or Imx1a gene products. Ordinarily, a Sonic hedgehog, nurr-1, pitx3, and/or Imx1a variant polynucleotide comprises in some embodiments at least about 80% nucleic acid sequence identity, in some embodiments at least about 81%, 82%, 83%, 84%, 85%, 86%, 87%, 88%, 89%, 90%, 91%, 92%, 93%, 94%, 95%, 96%, 97%, 98%, nucleic acid sequence identity, and in some embodiments at least about 99% nucleic acid sequence identity with the nucleic acid sequence encoding a full length native Sonic hedgehog, nurr-1, pitx3, and/or Imx1a variant polynucleotide. Such a nucleic acid can encode a full length native Sonic hedgehog, nurr-1, pitx3, and/or Imx1a gene products lacking the signal peptide, an extracellular domain of a Sonic hedgehog, nurr-1, pitx3, and/or Imx1a gene product, with or without the signal sequence, or any other fragment of a full length Sonic hedgehog, nurr-1, pitx3, and/or Imx1a gene product.

In some embodiments, a Sonic hedgehog, nurr-1, pitx3, and/or Imx1a variant polynucleotide is at least about 30 nucleotides in length, often at least about 60, 90, 120, 150, 180, 210, 240, 270, 300, 450, 600 nucleotides in length, more often at least about 900 nucleotides in length, or more.

The phrase "percent (%) nucleic acid sequence identity" with respect to Sonic hedgehog-, nurr-1-, pitx3-, and/or Imx1a gene product-encoding nucleic acid sequences identified herein is defined as the percentage of nucleotides in a candidate sequence that are identical with the nucleotides in the Sonic hedgehog, nurr-1, pitx3, and/or Imx1a sequence of interest after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

When nucleotide sequences are aligned, the percent nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) can be calculated as follows: % nucleic acid sequence identity=(W/Z)×100, where W is the number of nucleotides cored as identical matches by the sequence alignment program's or algorithm's alignment of C and D, and Z is the total number of nucleotides in D.

When the length of nucleic acid sequence C is not equal to the length of nucleic acid sequence D, the % nucleic acid sequence identity of C to D will not equal the % nucleic acid sequence identity of D to C. In some embodiments wherein a reference and test sequence overlaps, percent identity continues over the full length of one of the sequences.

V.I.2. Stringency

Homologs, orthologs (that is, nucleic acids encoding a Sonic hedgehog, nurr-1, pitx3, and/or Imx1a gene product derived from species other than human, for example), or other related sequences (for example, paralogs) can be obtained by low, moderate, or high stringency hybridization with all or a portion of a particular reference sequence serving as a probe in a nucleic acid hybridization reaction using methods well known in the art.

The specificity of single stranded DNA to hybridize complementary fragments is determined by the "stringency" of the reaction conditions. Hybridization stringency increases as the propensity to form DNA duplexes decreases. In nucleic acid hybridization reactions, the stringency can be chosen to either favor specific hybridizations (high stringency), which can be used to identify, for example, full length clones from a library. Less-specific hybridizations (moderate or low stringency) can be used to identify related, but not exact, DNA molecules (homologous, but not identical) or segments.

DNA duplexes are stabilized by: (1) the number of complementary base pairs; (2) the type of base pairs; (3) salt concentration (ionic strength) of the reaction mixture; (4) the temperature of the reaction; and (5) the presence of certain organic solvents such as formamide, which decreases DNA duplex stability. In general, the longer the probe, the higher the temperature required for proper annealing. A common approach is to vary the temperature: higher relative temperatures result in more stringent reaction conditions. The selection of modification of different stringency conditions based on the desired outcome of a hybridization reaction would be understood by one of ordinary skill in the art. See e.g., Tijssen, 1993; Sambrook & Russell, 2001; Ausubel et al. 2002; and Ausubel et al., 2003.

V.I.2(a) High Stringency

The phrases "highly stringent hybridization conditions" and "high stringency" generally refer to conditions under which a probe hybridizes to its target subsequence, typically in a complex mixture of nucleic acid, but to no other sequences. Highly stringent conditions are sequence-dependent and can be different in different circumstances. Longer sequences hybridize specifically at higher temperatures. Generally, highly stringent conditions are selected to be about 5-10° C. lower than the thermal melting point ($T_m$) for the specific sequence at a defined ionic strength pH. Low stringency conditions are generally selected to be about 15-30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions are those in which the salt concentration is in some embodiments less than about 1.0 M sodium ion, in some embodiments about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Highly stringent conditions can also be achieved with the addition of destabilizing agents such as formamide. For selective or specific hybridization, a positive signal is in some embodiments at least two times background, and in some embodiments at least 10 times background hybridization. Exemplary highly stringent conditions comprise: (1) low ionic strength and high temperature washes (for example, 15 mM sodium chloride, 1.5 mM sodium citrate, 0.1% sodium dodecyl sulfate at 50°); (2) a denaturing agent during hybridization (for example, 50% (v/v) formamide, 0.1% bovine serum albumin, 0.1% Ficoll, 0.1% polyvinylpyrrolidone, 50 mM sodium phosphate buffer (pH 6.5; 750 mM sodium chloride, 75 mM sodium citrate at 42°); or (3) 50% formamide. Washes typically also comprise 5×SSC (0.75 M 10 NaCl, 75 mM sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42°, with washes at 42°. in 0.2× SSC (sodium chloride/sodium citrate) and 50% formamide at 55°, followed by a high-stringency wash consisting of 0.1× SSC containing EDTA at 55°. In some embodiments, the conditions are such that sequences at least about 65%, 70%, 75%, 85%, 90%, 95%, 98%, or 99% homologous to each other typically remain hybridized to each other. These conditions are presented as examples and are not meant to be limiting.

V.I.2(b) Moderate Stringency

The phrases "moderately stringent conditions" and "moderate stringency" refer to hybridization conditions and/or washing solutions that are less stringent than highly stringent conditions such that a polynucleotide can hybridize to one or more target sequences that differ in their nucleotide sequences from those to which it would hybridize under highly stringent conditions. A reduction in stringency from "high" to "moderate" can be accomplished by lowering the temperature of and/or increasing the concentration of monovalent cation present in the hybridization and/or wash solutions. An exemplary moderate stringency condition comprises hybridization in 6×SSC, 5×Denhardt's solution, 0.5% SDS, and 100 mg/ml denatured salmon sperm DNA at 55° C., followed by one or more washes in 1×SSC, 0.1% SDS at 37° C. The temperature, ionic strength, etc., can be adjusted to accommodate experimental factors such as probe length. Other moderate stringency conditions are described in Tijssen, 1993; Sambrook & Russell, 2001; Ausubel et al., 2002; and Ausubel et al., 2003.

V.I.2(c) Low Stringency

As used herein, the phrases "low stringent conditions" and "low stringency" refer to hybridization conditions and/or washing solutions that are less stringent than moderately stringent conditions such that a polynucleotide can hybridize to one or more target sequences that differ in their nucleotide sequences to a greater degree from those to which it would hybridize under moderately stringent conditions. A non-limiting example of low stringency hybridization conditions is hybridization in 6×SSC, 50 mM Tris-HCl (pH 7.5), 5 mM EDTA, 0.02% PVP, 0.02% Ficoll, 0.2% BSA, 100 mg/ml denatured salmon sperm DNA, and 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency, such as those for cross-species hybridizations, are described in Tijssen, 1993; Sambrook & Russell, 2001; Ausubel et al., 2002; and Ausubel et al., 2003.

V.J. Polypeptides

In some embodiments, the presently disclosed subject matter pertains to isolated Sonic hedgehog, nurr-1, pitx3, and/or Imx1a polypeptides, and biologically-active portions derivatives, fragments, analogs, homologs, and orthologs thereof. Also provided are polypeptide fragments suitable for use as immunogens to raise anti-Sonic hedgehog, nurr-1, pitx3, and/or Imx1a antibodies. In some embodiments, a native Sonic hedgehog, nurr-1, pitx3, and/or Imx1a polypeptide can be isolated from cells or tissue sources by an appropriate purification scheme using standard protein purification techniques. In some embodiments, Sonic hedgehog, nurr-1, pitx3, and/or Imx1a polypeptides are produced by recombinant DNA techniques. Alternative to recombinant expression, a Sonic hedgehog, nurr-1, pitx3, and/or Imx1a polypeptide can be synthesized chemically using standard peptide synthesis techniques.

A Sonic hedgehog, nurr-1, pitx3, and/or Imx1a polypeptide includes the amino acid sequence of a Sonic hedgehog, nurr-1, pitx3, and/or Imx1a gene product. The presently disclosed subject matter also includes a mutant or variant protein any of whose residues can be changed from the corresponding residues found for each gene, while still encoding a protein that maintains its Sonic hedgehog, nurr-1, pitx3, and/or Imx1a biological activities and physiological functions as a lineage priming agent, or a functional fragment thereof.

In general, a Sonic hedgehog, nurr-1, pitx3, and/or Imx1a variant that preserves a Sonic hedgehog-, nurr-1-, pitx3-, and/or Imx1a-like function as a lineage priming agent and includes any variant in which residues at a particular position in the sequence have been substituted by other amino acids, and further includes the possibility of inserting an additional residue or residues between two residues of the parent protein as well as the possibility of deleting one or more residues from the parent sequence. Any amino acid substitution, insertion, or deletion is encompassed by the invention. In favorable circumstances, the substitution is a conservative substitution as defined above.

In addition to naturally-occurring allelic variants of Sonic hedgehog, nurr-1, pitx3, and/or Imx1a gene products, amino acids changes can be introduced recombinantly into a polypeptide by mutagenesis of the nucleotide sequences that encode the amino acid sequences of the Sonic hedgehog, nurr-1, pitx3, and/or Imx1a gene products. In some embodiments, the amino acid changes are designed to not appreciably alter the biological activities of the mutated Sonic hedgehog, nurr-1, pitx3, and/or Imx1a polypeptides as compared to naturally occurring (e.g., wild type) polypeptides. For example, nucleotide substitutions leading to amino acid substitutions at "non-essential" amino acid residues can be made in the corresponding gene sequences. A "non-essential" amino acid residue is a residue that can be altered from the wild type sequence of the Sonic hedgehog, nurr-1, pitx3, and/or Imx1a gene products without altering their biological activity as a lineage priming agent, whereas an "essential" amino acid residue is required for such biological activity.

For instance, amino acid residues that are conserved among the orthologous Sonic hedgehog, nurr-1, pitx3, and/or Imx1a genes from different species are predicted to be particularly non-amenable to alteration. However, it can be possible to introduce conservative amino acid substitutions at these amino acids. Exemplary conservative substitutions are shown in Table 2 below. Conservative substitutions whereby an amino acid of one class is replaced with another amino acid of the same type fall within the scope of the presently disclosed subject matter so long as the substitution does not undesirably alter the biological activity of the modified polypeptide as a lineage priming agent.

TABLE 2

Conservative Amino acid Substitutions

| Original Residue | Exemplary Substitutions |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| Gly (G) | Pro, Ala |
| His (H) | Asn, Gln, Lys, Arg |
| Ile (I) | Leu, Val, Met, Ala, Phe, Norleucine (Nor) |
| Leu (L) | Nor, Ile, Val, Met, Ala, Ile, Phe |
| Lys (K) | Arg, Gln, Asn |
| Met (M) | Leu, Phe, Ile |
| Phe (F) | Leu, Val, Ile, Ala, Tyr |
| Pro (P) | Ala |
| Ser (S) | Thr |
| Thr (T) | Ser |
| Trp (W) | Phe, Tyr |
| Tyr (Y) | Trp, Phe, Thr, Ser |
| Val (V) | Ile, Leu, Met, Phe, Ala, Leu, Nor |

Non-conservative substitutions that effect (1) the structure of the polypeptide backbone, such as a β-sheet or α-helical conformation; (2) the charge; (3) hydrophobicity or hydrophilicity; or (4) the bulk of the side chain of the target site, can modify a Sonic hedgehog, nurr-1, pitx3, and/or Imx1a polypeptide's function and/or immunological identity. Residues can be divided into groups based on common side-chain properties as denoted in Table 3. In some embodiments, substitutions can entail exchanging a member of one of these classes for another class. Substitutions based on the classes listed in Table 3 can be introduced in some embodiments into conservative substitution sites, and/or in some embodiments into non-conserved sites.

TABLE 3

Amino Acid Classes

| Classes | Exemplary Amino Acids |
|---|---|
| hydrophobic | Nor, Met, Ala, Val, Leu, Ile |
| neutral/hydrophilic | Cys, Ser, Thr |
| acidic | Asp, Glu |
| basic | Asn, Gln, His, Lys, Arg |
| disrupt chain conformation | Gly, Pro |
| aromatic | Trp, Tyr, Phe |

Variant polypeptides comprising one or more substitutions can be produced using methods that are known in the art such as oligonucleotide-mediated (site-directed) mutagenesis, alanine scanning, and PCR mutagenesis. Site-directed mutagenesis (Carter, 1986; Zoller & Smith, 1987), cassette mutagenesis, restriction selection mutagenesis (Wells et al., 1985), or other known techniques can be performed on an isolated nucleic acid sequence to produce, for example, variant Sonic hedgehog, nurr-1, pitx3, and/or Imx1a nucleic acids (see e.g., Sambrook & Russell, 2001; Ausubel et al., 2002; Ausubel et al., 2003).

A variant nucleic acid molecule can comprise a nucleotide sequence that encodes a variant protein, wherein the variant protein comprises an amino acid sequence that is in some embodiments at least about 45%, in some embodiments at least about 50%, in some embodiments at least about 55%, in some embodiments at least about 60%, in some embodiments at least about 65%, in some embodiments at least about 70%, in some embodiments at least about 75%, in some embodiments at least about 80%, in some embodiments at least about 85%, in some embodiments at least about 90%, in some embodiments at least about 95%, in some embodiments at least about 96%, in some embodiments at least about 97%, in some embodiments at least about 98%, and in some embodiments at least about 99% identical to a naturally-occurring Sonic hedgehog, nurr-1, pitx3, and/or Imx1a gene product.

As such, the phrase "Sonic hedgehog, nurr-1, pitx3, and/or Imx1a polypeptide variant" refers to an active Sonic hedgehog, nurr-1, pitx3, and/or Imx1a polypeptide having at least: (1) about 80% amino acid sequence identity with a full length native Sonic hedgehog, nurr-1, pitx3, and/or Imx1a polypeptide sequence; (2) a Sonic hedgehog, nurr-1, pitx3, and/or Imx1a polypeptide sequence lacking the signal peptide; (3) an extracellular domain of a Sonic hedgehog, nurr-1, pitx3, and/or Imx1a polypeptide, with or without the signal peptide; or (4) any other fragment of a full length Sonic hedgehog, nurr-1, pitx3, and/or Imx1a polypeptide sequence. For example, Sonic hedgehog, nurr-1, pitx3, and/or Imx1a polypeptide variants include Sonic hedgehog, nurr-1, pitx3, and/or Imx1a polypeptides wherein one or more amino acid residues are added or deleted at the N- or C-terminus of the full length native amino acid sequence. A Sonic hedgehog, nurr-1, pitx3, and/or Imx1a polypeptide variant can have in some embodiments at least about 80% amino acid sequence identity, in some embodiments at least about 81% amino acid sequence identity, in some embodiments at least about 82%, 83%, 84%, 85%, 86%, 87%, 88%, 89%, 90%, 91%, 92%, 93%, 94%, 95%, 96%, 97%, 98% amino acid sequence identity, and in some embodiments at least about 99% amino acid sequence identity with a full length native sequence Sonic hedgehog, nurr-1, pitx3, and/or Imx1a polypeptide sequence. A Sonic hedgehog, nurr-1, pitx3, and/or Imx1a polypeptide variant can have a sequence lacking the signal peptide, an extracellular domain of a Sonic hedgehog, nurr-1, pitx3, and/or Imx1a polypeptide, with or without the signal peptide, or any other fragment of a full length Sonic hedgehog, nurr-1, pitx3, and/or Imx1a polypeptide sequence. Ordinarily, Sonic hedgehog, nurr-1, pitx3, and/or Imx1a variant polypeptides are at least about 10 amino acids in length, often at least about 20 amino acids in length, more often at least about 30, 40, 50, 60, 70, 80, 90, 100, 150, 200, or 300 amino acids in length, or more.

"Percent amino acid sequence identity" is defined as the percentage of amino acid residues that are identical with amino acid residues in a reference Sonic hedgehog, nurr-1, pitx3, and/or Imx1a polypeptide sequence in a candidate sequence when the two sequences are aligned. To determine percent amino acid identity, sequences are aligned and if necessary, gaps are introduced to achieve the maximum percent sequence identity; conservative substitutions are not considered as part of the sequence identity. Amino acid sequence alignment procedures to determine percent identity are well known to those of skill in the art. Often publicly available computer software such as BLAST, BLAST2, ALIGN2 or Megalign (DNASTAR) software is used to align peptide sequences. Those skilled in the art can determine appropriate parameters for measuring alignment, including any algorithms needed to achieve maximal alignment over the full length of the sequences being compared.

When amino acid sequences are aligned, the percent amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) can be calculated as: % amino acid sequence identity=$(X/Y) \times 100$, where X is the number of amino acid residues scored as identical matches by the sequence alignment program's or algorithm's alignment of A and B, and Y is the total number of amino acid residues in B.

If the length of amino acid sequence A is not equal to the length of amino acid sequence B, the % amino acid sequence identity of A to B will not equal the % amino acid sequence identity of B to A. In some embodiments wherein a reference and test sequence overlaps, percent identity continues over the full length of one of the sequences.

An "isolated" or "purified" polypeptide, protein or biologically active fragment is separated and/or recovered from a component of its natural environment. Contaminant components include materials that would typically interfere with diagnostic or therapeutic uses for the polypeptide, and can include enzymes, hormones, and other proteinaceous or non-proteinaceous materials. In some embodiments, the polypeptide is purified to a sufficient degree to obtain at least 15 residues of N-terminal or internal amino acid sequence. To be substantially isolated, preparations having in some embodiments less than 30%, in some embodiments less than 20%, in some embodiments less than 10%, and in some embodiments less than 5% by dry weight of non-Olig2, HB9, Ngn2, Sox10, or Nkx2.2 contaminating material. An isolated, recombinantly-produced Olig2, HB9, Ngn2, Sox10, or Nkx2.2 or biologically active portion is in some embodiments substantially free of culture medium. That is, culture medium represents in some embodiments less than 20%, in some embodiments less than about 10%, and in some embodiments less than about 5% of the volume of the Olig2, HB9, Ngn2, Sox10, or Nkx2.2 preparation. Examples of contaminants include cell debris, culture media, and substances used and produced during in vitro synthesis of an Olig2, HB9, Ngn2, Sox10, or Nkx2.2.

Biologically active portions of a Sonic hedgehog, nurr-1, pitx3, and/or Imx1a gene product include peptides comprising amino acid sequences sufficiently homologous to or derived from the amino acid sequences of a Sonic hedgehog, nurr-1, pitx3, and/or Imx1a gene product (or a nucleic acid sequence encoding such a portion) that include fewer amino acids than a full length Sonic hedgehog, nurr-1, pitx3, and/or Imx1a gene product, and exhibit at least one activity of a Sonic hedgehog, nurr-1, pitx3, and/or Imx1a gene product, such as its activity as a lineage priming agent. Biologically active portions can comprise a domain or motif with at least one activity of a native Sonic hedgehog, nurr-1, pitx3, and/or Imx1a gene product. A biologically active portion of a Sonic hedgehog, nurr-1, pitx3, and/or Imx1a gene product can be a polypeptide that is, for example, 10, 25, 50, 100, or more amino acid residues in length. Other biologically active portions, in which other regions of the protein are deleted, can be prepared by recombinant techniques and evaluated for one or more of the functional activities of a native Olig2, HB9, Ngn2, Sox10, or Nkx2.2.

The phrase "Sonic hedgehog, nurr-1, pitx3, and/or Imx1a variant" also refers in some embodiments to a biologically active Sonic hedgehog, nurr-1, pitx3, and/or Imx1a gene product having at least: (1) about 80% amino acid sequence identity with a full length native Sonic hedgehog, nurr-1, pitx3, and/or Imx1a sequence; (2) a Sonic hedgehog, nurr-1, pitx3, and/or Imx1a sequence lacking the signal peptide; (3) an extracellular domain of a Sonic hedgehog, nurr-1, pitx3, and/or Imx1a gene product, with or without the signal peptide; or (4) any other fragment of a full length Sonic hedgehog, nurr-1, pitx3, and/or lmx1a sequence. For example, Sonic hedgehog, nurr-1, pitx3, and/or lmx1a variants include a Sonic hedgehog, nurr-1, pitx3, and/or lmx1a wherein one or more amino acid residues are added or deleted at the N- or C-terminus of the full length native amino acid sequence. A Sonic hedgehog, nurr-1, pitx3, and/or lmx1a variant can have a sequence lacking the signal peptide, an extracellular domain of a Sonic hedgehog, nurr-1, pitx3, and/or lmx1a gene product, with or without the signal peptide, or any other fragment of a full length Sonic hedgehog, nurr-1, pitx3, and/or lmx1a sequence. Ordinarily, Sonic hedgehog, nurr-1, pitx3, and/or lmx1a variant polypeptides are at least about 10 amino acids in length, often at least about 20 amino acids in length, and more often at least about 30, 40, 50, 60, 70, 80, 90, 100, 150, 200, or 300 amino acids in length, or more.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently disclosed subject matter.

Materials and Methods Employed in the Examples

Cell culture. The two patient-specific olfactory epithelial-derived progenitor lines used in this study were obtained from adult olfactory epithelium harvested from a 42-year-old female patient and a 20-year-old male via endoscopic biopsy (Roisen et al., 2001; Winstead et al., 2005). The cells were cultured as neurosphere-forming cells (NSFCs) as previously described (Zhang et al., 2004; Winstead et al., 2005). The NSFCs were thawed from frozen stock that was maintained in liquid Nitrogen and cultured in minimal essential medium (MEM) with 10% heat inactivated fetal bovine serum (FBS) (GIBCO, Grand Island, N.Y.) for a week. The NSFCs were adapted to the absence of serum via serial dilution of serum every day for 4 days until the cells were finally cultured in DFBNM (DMEM/F12 supplemented with 1% B27 and 0.5% $N_2$ and 100 µg/ml gentamycin (GIBCO, Grand Island, N.Y.; Zhang et al., 2004). Parallel independent experiments were performed on both patient-specific NSFC lines. Since equivalent results were achieved, data from only one line have been presented.

Construction of expression plasmids. The mouse nurr1 cDNA was cloned into the pLNCX2 expression vector (Clontech) between ClaI. Similarly, the rat pitx3 and mouse lmx1a cDNA were inserted into pLNCX2 vector between ClaI. For the nurr1 and pitx3 co-expression vector, nurr1 cDNA was cloned into pIRES (Clontech) between XbaI and SalI, and pitx3 was inserted between EcoRI. The pLNCX2 and pIRES expression vectors served as controls. All expression vectors were verified by extensive DNA sequencing.

Transfection and selection. All plasmid constructs were introduced into the NSFCs by liposomal transfection. The cells were plated on glass coverslips in six-well plates ($5 \times 10^4$ cells per 35-mm well) in DFBNM without antibiotics 1 day before transfection. NSFCs were transfected with each plasmid (4 µg/well) for 24 hours according to the manufacture's protocol (LIPOFECTAMINE™ 2000, Invitrogen, Carlsbad, Calif., United States of America). One day after transfection, the cells were fed with 10% FBS in MEM and selected with G418 (400 µg/ml; Invitrogen, Carlsbad, Calif., United States of America). The selection pressure was kept for up to 4 months to insure a purified stably transfected cell population. Immunocytochemistry and western blot analysis were applied to detect several dopaminergic neuronal markers. After a 4-month selection, the transfected NSFCs were frozen in liquid nitrogen for additional 4-6 months of storage. After removal from cryostorage and several days' recovery in MEM with 10% FBS at 37° C., the dopaminergic lineage restriction was probed with immunocytochemistry and western blot analysis.

Morphogenic treatment. The NSFCs were treated with Shh, in the presence or absence of RA (1 µM) and/or FN (5 µM; Zhang et al., 2004). Highly purified Shh (kindly provided under a Material Transfer Agreement with Curis and Wyeth, Inc.) was applied to NSFCs and compared to a commercially available control sample obtained from Sigma-Aldrich Chemical Co. (St. Louis, Mo., United States of America) to determine the extent to which purification of Shh can effect the expression of tyrosine hydroxylase (TH). The NSFCs were plated on glass coverslips in six-well plates ($5 \times 10^4$ cells/35-mm well) in DFBNM and treated with medium containing various concentrations and combinations of RA, FN, and Shh for 7 days ($CO_2$ atmosphere at 5% and temperature of 37° C.). Treatment with Shh included several concentrations 0.25 mg/ml ("Shh0.25"), 0.1 mg/ml ("Shh0.1"), 0.05 mg/ml ("Shh0.05"), 0.025 mg/ml ("Shh0.025") in the presence or absence of retinoic acid 1 µM RA ("RA1") and/or forskolin, 5 µM FN ("FN5"). After treatment, TH expression was determined at 1-7 days in vitro (DIV) by immunocytochemical analysis. Once the optimized environment for inducing dopaminergic neurons was determined, the medium containing the optimized combination was applied to stably transfected NSFCs.

Immunocytochemistry. The NSFCs ($5 \times 10^4$ cells/well) were plated on 22-mm round glass coverslips in 35-mm six well plates (Becton, Dickinson and Co., Franklin Lakes, N.J., United States of America) and incubated at 37° C. in 5% $CO_2$/95% air for 24 hours and treated with RA, FN, and Shh or transfected and selected for different periods of time prior to fixation for immunofluorescence. 4,6-diamidino-2-phenylindole dihydrochloride (DAPI; 1:1000, 2 mg/ml, Molecular Probes, Eugene, Oreg., United States of America) was applied in culture for 30 min at 37° C. for vital nuclear staining. The coverslips were rinsed with cytoskeletal buffer (CB) twice and fixed in 3% paraformaldehyde in CB (10 minutes). 0.2% Triton X-100 (10 minutes; Sigma-Aldrich Chemical Co., St. Louis, Mo., United States of America) in TBS was applied and cells were incubated (1 hour) in 3% BSA in TBS. Primary antibodies were applied overnight (4° C.). After 30 minutes' washing (10 minutes each, 3 times) in TBS, the cells were incubated with secondary antibodies: Texas-red conjugated goat anti-rabbit IgG, Texas-red-conjugated goat antimouse IgG, Cy2-conjugated goat anti-mouse IgG and/or Cy2-conjugated goat anti-rabbit IgG (all diluted 1:600; Cy2, Jackson ImmunoResearch Laboratories, Inc., West Grove, Pa., United States of America; Texas Red, Molecular Probes, Eugene, Oreg., United States of America). The coverslips were rinsed in TBS for 30 minutes (10 minutes each, 3 times) and mounted on slides. The slides were examined with the confocal microscopy. All experiments were repeated a minimum of two times to ensure the specificity and reliability of the staining; only one set of data has been presented since similar results were obtained.

Western blot analysis. Western blot analysis was used to further examine and confirm the results obtained with immunofluorescence. Proteins from NSFCs cultured in DFBNM without transfection, NSFCs transfected with control vectors, as well as NSFCs transfected with the vectors plus each combination of transcriptions factors (pLNCX2-pitx3, pLNCX2-nurr1, pLNCX2-lmx1a, pIRES-pitx3-nurr1), selected in all groups were collected in cell lysis buffer (Sigma Aldrich Co., St. Louis, Mo., United States of America). After 15 minutes of incubation on ice, samples were centrifuged for 30 minutes (4° C.) and the protein concentration of each supernatant was determined. The protein samples (20 μg/well) were electrophoresed on 10% SDS-polyacrylamide gels along with standardized-molecular-size marker proteins in an adjacent lane and transferred from gel to nitrocellulose paper. Nonspecific binding was blocked (1 hour) with 5% nonfat dry milk in TBS-Tween (TBST) buffer. Blots were incubated (4° C. overnight) in primary antibodies (anti-TH, MAB; anti-actin, MAB). TBST was used three times for 10 minutes on the blots. Washed blots were incubated (1 hour, room temperature) monoclonal horseradish peroxidase-labeled anti-mouse IgG (1:2,000). ECL Western blotting detection reagents (Amersham Biosciences, a division of GE Healthcare Life Sciences, Piscataway, N.J., United States of America) were used to identify bound antibodies. Densitometry of the protein bands was carried out on a high performance chemiluminescence film (Amersham Biosciences). Data were analyzed using the Image-J software programs supplied by the NIH.

Dopamine assay. Stably transfected NSFCs were plated in flasks (25 cm2, Corning) at 105 per flask before they were adapted to the absence of serum via serial dilution of serum every day for 4 days until the cells were finally cultured in DFBNM, which was collected daily after the serum was totally eliminate from the medium. The DFBNM collected from each restricted NSFC line was then concentrated to 1/50 volume respectively by centrifugal filters (Amicon Ultra-15; Millipore, Billerica, Mass., United States of America). The differentiated NSFCs were then collected and lysed (lysis buffer, Sigma). Dopamine expression was analyzed quantitatively in the concentrated medium as well as in the cell lysates with a dopamine enzyme immunoassay kit (Dopamine EIA, Immuno-Biological Laboratories, Inc., Minneapolis, Minn., United States of America), according to the manufacturer's protocol.

General surgical procedures. Female Sprague Dawley rats (250-300 g each) were employed. Twenty-four hours prior to surgery, animals were weighed and assigned identification numbers. On the day of surgery, the animals were anesthetized using 37.7 mg ketamine and 5 mg xylazine per kilogram, with 0.1 ml/100 g injected i.p. After anesthesia (30 minutes before lesion), 25 mg/kg of desipramine (0.1 ml/100 g of a 25 mg/ml stock) was injected intramuscularly into each mouse to protect noradrenergic neurons from 6-OHDA toxicity. 50 mg/kg of pargyline (0.1 ml/100 g of a 50 mg/ml stock) was also administered intramuscularly to each mouse to inhibit endogenous monoamine oxidase.

Unilateral 6-OHDA lesioning. For each rat, the hair was shaved and the skin prepared with BETADINE® solution at the surgical site. The rat's head was placed in a three point stereotactic holding device (incisor bar set −3.9 mm below the interaural line), the scalp was opened, a small burr hole was drilled into the skull with a dental drill, and the dura were cut.

Two models of 6-ODHA lesioning were employed. The first was a Median Forebrain Bundle (MFB) model. For this model, 4 μl of freshly prepared 6-OHDA (5 mg/mL dissolved in 0.2 mg/ml ascorbic acid in 0.9% saline, kept in the dark until used) was injected into each rat at a position defined as (−4.4 mm anterior, +1.2 mm lateral, 7.8 mm ventral to bregma).

The second model was a striatum model. 2 μl of freshly prepared 6-OHDA at 3.0 mg/ml were injected at each of 3 points defined as (+0.4 mm, +3.0 mm, 5.0 mm; −0.4 mm, +4.2 mm, 5.0 mm; and −1.3 mm, +4.5 mm, 5.0 mm) using a G#31 needle at a rate of 1 μl/min. The needle was left in place for four minutes to prevent backflow and then slowly removed. The burr hole was filled with a piece of gel foam and the scalp was closed.

In the absence of transplantation, administration of amphetamine to lesioned rats resulted in unilaterally lesioned animals rotating toward the lesioned side.

The general antibiotic penicillin (100,000 units/kg) was administered intramuscularly to each animal. Each animal also received a post-operative analgesic (Buprenorphine, 0.02 mg/kg, intramuscularly). 5-10 mL of 0.9% saline (SC) was also administered to counteract any fluid/blood loss.

Cell transplantation surgery. Each rat was placed under anesthesia as described above, placed in the stereotactic holder, its scalp re-opened, a new burr hole drilled, and 10,000-50,000 NSFCs in 5 μl were administered into the striatum at 2 points (+0.5 mm, +2.5 mm, 4.5/5.5 mm) with a Hamilton Syringe fitted with a G#31 syringe needle. Again, the needled was left in place for four minutes and then removed. The scalp was closed. Each surgical procedure lasted no longer than 60 minutes. The stereotaxic coordinates were from Paxinos & Watson, 1998. The general care of post-operation was same as above, and all rats received Cyclosporin (10 mg/kg, i.m.) every other day for immuno-suppression for at least 16 weeks.

Example 1

Transfection of Olfactory Epithelial-Derived Progenitors (NSFCs) to Achieve Dopaminergic Lineage Restriction Human NSFCs were obtained from previously frozen stocks with low passage number (3-5) and maintained in MEM10 medium during their recovery period. These mitotically active cells divided every 18-20 hours, which typically required passage three times per week. The heterogeneous nature of the NSFC population prior to transfection was determined by immunocytochemistry. No reactivity was observed for pitx3, nurr1. lmx1a or the dopamine precursor, TH, with pre-transfected NSFCs. Low passages (Passage 4-8) of NSFCs from 2 different patient-specific cell lines were employed in parallel transfection experiments. To examine the phenotypic expression of NSFCs after transfection and selection, representative cultures as well as their respective pre-transfection controls were evaluated. Non-transfected NSFCs or those transfected with LIPOFECTAMINE™ alone died within 1 week after selection with 400 μg/ml G418 (GIBCO, Grand Island, N.Y.). In contrast, 30% of the transfected cells (both with the concerned genes and the control vectors) survived under the selection pressure. Transfection with control vectors, single genes, or pitx3-nurr1 combined resulted in no morphologic changes compared to the typical pretreated NSFCs. However, the transfected NSFCs divided more slowly, with a new doubling time of three to four days, which required a feeding schedule of only twice a week and necessitated passage every 9-10 days. Immunofluorescent analysis of the transfected populations demonstrated that NSFCs were stably transfected and TH expressed.

Human olfactory epithelial derived NSFCs were transfected by pIRES-pitx3-nurr1 to restrict them towards DA neurons. The vector alone was employed as a control. To obtain a purified population of restricted cells the transfected population was maintained in G418 (GIBCO, 400 μg/ml) for selection. Although only several weeks of selection produced relatively pure populations, an interval of four months was employed to insure stability and purity. NSFCs remained TH-positive after transfection of pIRESpitx3-Nur1, whereas the transfection of control vectors exhibited no phenotypic changes, demonstrating that NSFCs can be restricted towards dopaminergic neurons (see FIG. 1).

NSFCs were transfected with pLNCX2-nurr1, pLNCX2-pitx3, pLNCX2-lmx1a or the vector alone as a control. The transfected cells were exposed to G418 for selection for periods up to 4 months. NSFCs were TH-positive after transfection of pLNCX2-nurr1 and pLNCX2-pitx3, whereas the transfection of control vectors resulted in no phenotypic changes. Therefore pLNCX2-nurr1 or pLNCX2-pitx3 can be employed to lineage restrict the NSFCs towards dopaminergic neurons. In contrast, the NSFCs transfected with pLNCX2-lmx1a remained unreactive for TH, although positive of myc, which demonstrated the successful incorporation of the plasmid (see FIG. 1).

Figure 2:
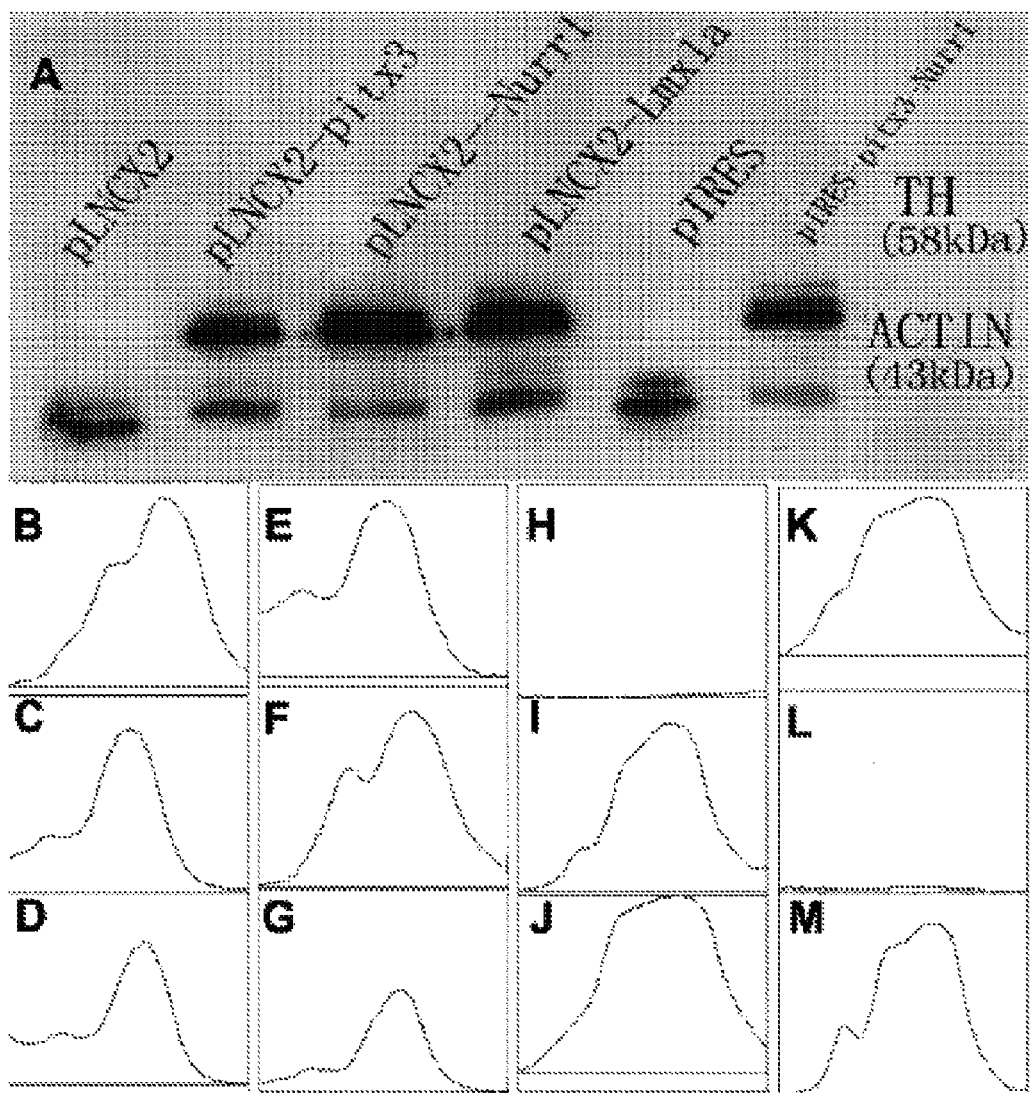
Figure 2:
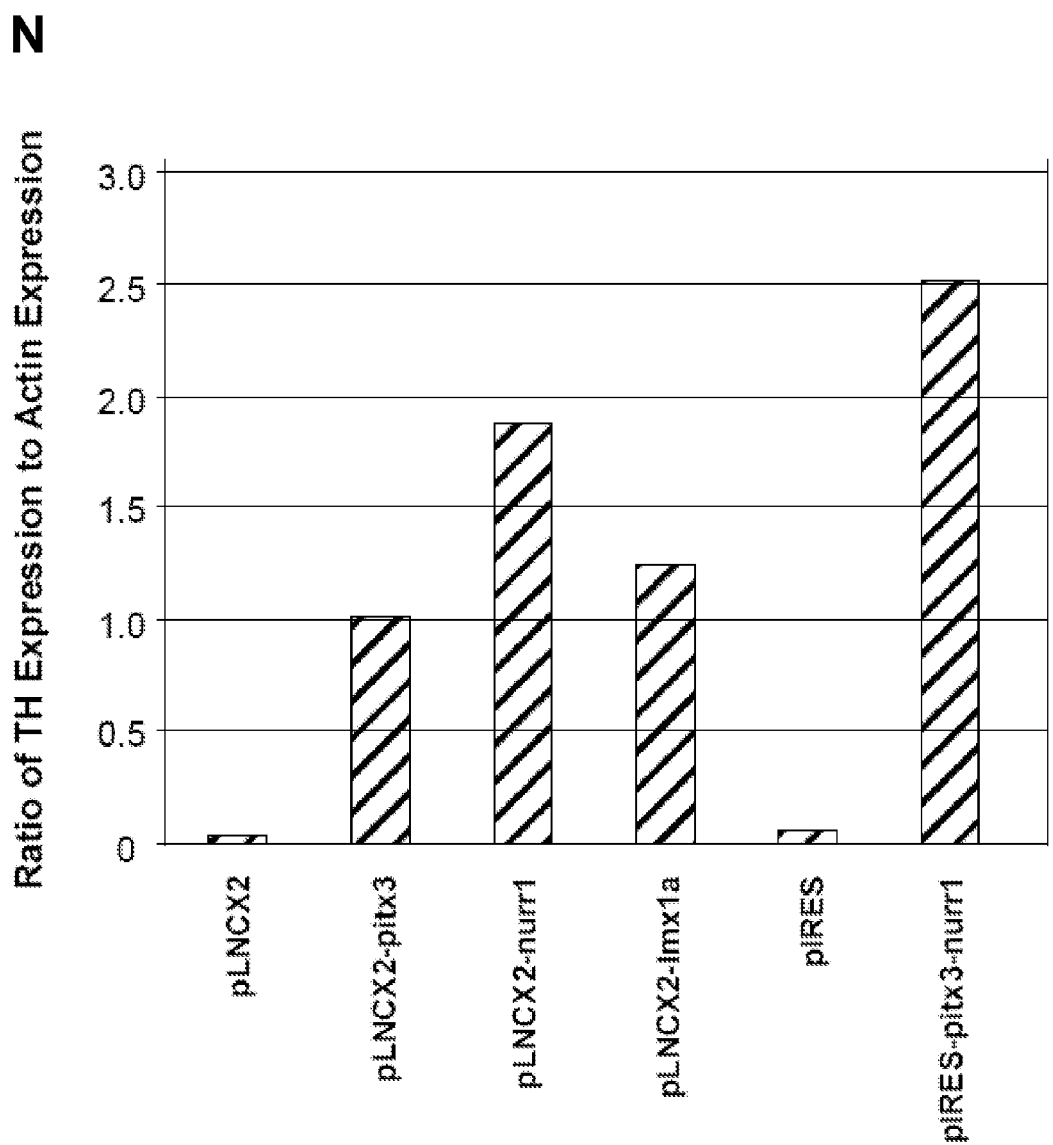

Western blot analysis was employed to confirm quantitatively the immunocytochemical studies of the transfected NSFC populations. The following transfected lines were analyzed for TH expression: NSFCs transfected with pIRES-pitx3-nurr1, pLNCX2-nurr1, pLNCX2-pitx3, or pLNCX2-lmx1a were analyzed for TH expression, and it was determined that all were TH-positive. This indicated that these cells had the potential to produce dopamine. In contrast, the NSFC populations transfected with the control vectors (pIRES and pLNCX2) did not exhibit TH expression. Beta-actin, a protein that is widely expressed in all mammalian and avian cells was used as a reference protein for the comparison of TH expression by the various lines (Tian et al., 1999). Image-J was applied for the data analysis. Each curve in FIGS. 2B to 2M exhibits the density of bands shown on the western gel (see FIG. 2A). The area under each curve was measured. The frequency distribution histogram in FIG. 2N presents the ratio of TH to ACTIN expression in each cell line. NSFCs transfected with pIRES-pitx3-nurr1 exhibited the highest ratio for TH to ACTIN expression, while the cells transfected with the control vector (pLNCX2 or pIRES) had the least TH staining (see FIGS. 2B-2N). These results demonstrated that individual transcription factors had unique capabilities for promoting the dopaminergic restriction of NSFCs.

Example 2

Figure 3:
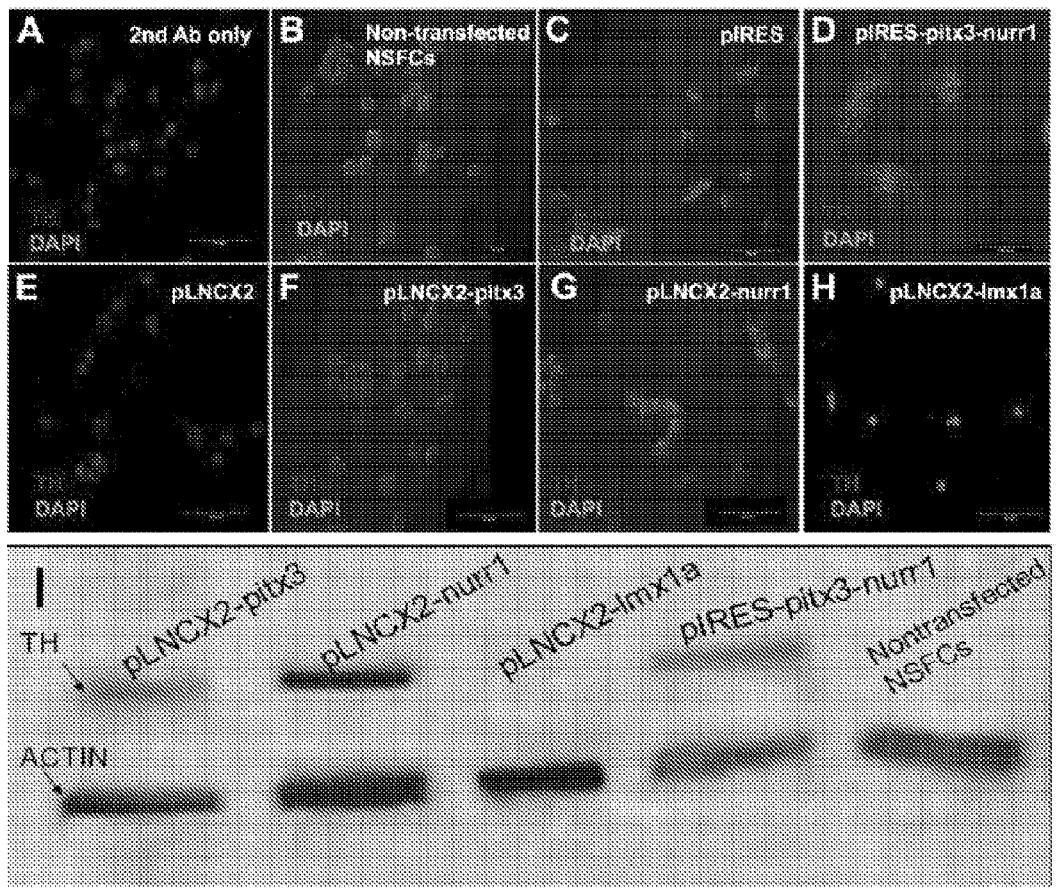
FIGS. 3A-3I are the results of immunocytochemistry and Western blot analyses of cells or lysates assayed with antibodies that bind to TH, pitx3, or nurr1, demonstrating that NSFCs transfected with pLNCX2-pitx3, pLNCX2-nurr1 and pIRES-pitx3-nurr1 remain healthy and TH-positive (FIGS. 3D, 3F, 3G, and 3I), while an NSFC line transfected with pLNCX2-Imx1a lost TH expression following removal from cryostorage and under selection pressure (FIGS. 3H and 3I).

Transfected NSFCs Remain Restricted to Dopaminergic Lineage after Removal from Cryostorage After a 4 month selection, the dopaminergic lineage restricted cells were frozen in liquid nitrogen for additional 4-6 months. After removal from cryostorage and several days' recovery in MEM10 at 37° C., almost all the NSFC populations survived under the selection pressure of 400 µg/ml G418, demonstrating that these cells were stably transfected and retained their potential for long term storage and clinical application. Immunocytochemistry and western blot analysis were applied to these previously stored populations to examine their TH expression. The NSFCs transfected with pLNCX2-pitx3, pLNCX2-nurr1, and pIRES-pitx3-nurr1 remained healthy and TH-positive under the pressure of selection, while the pLNCX2-lmx1a transfected line did not (see FIG. 3).

Example 3

Lineage Restricted NSFCs Produced and Released Dopamine

Figure 4A:
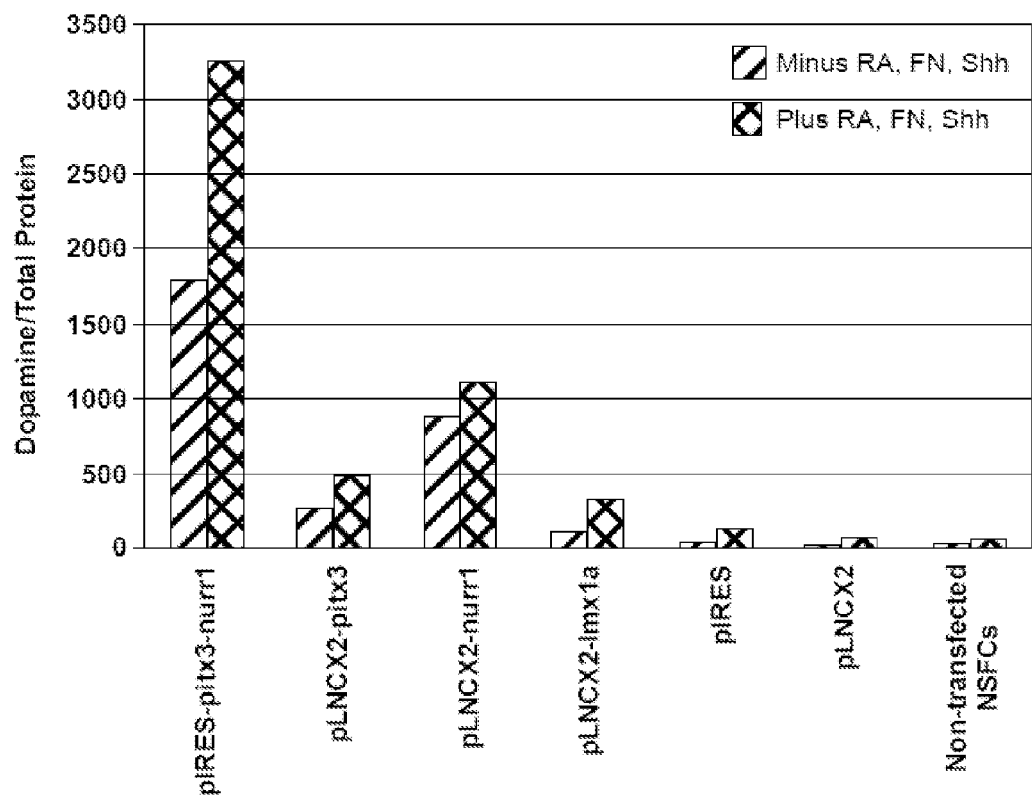
FIGS. 4A and 4B are bar graphs depicting the results of assaying dopamine levels per total protein (expressed as pg/µl/mg protein) of NSFCs transfected with various expression constructs. Singly hatched boxes correspond to cells grown in the absence of retinoic acid (RA), forskolin (FN), and Sonic hedgehog (Shh), while doubly hatched boxes correspond to cells grown in the presence of RA, FN, and Shh (RA1FN5Shh, which is 1 µM RA, about 5 µM FN, and about 0.025 µg/ml Shh). As shown in these Figures, NSFCs transfected with pIRES-pitx3-nurr1 were the most efficient dopamine-producing lines both intracellularly and intercellularly. Dopamine levels in NSFCs and in the spent medium were raised.
Figure 4B:
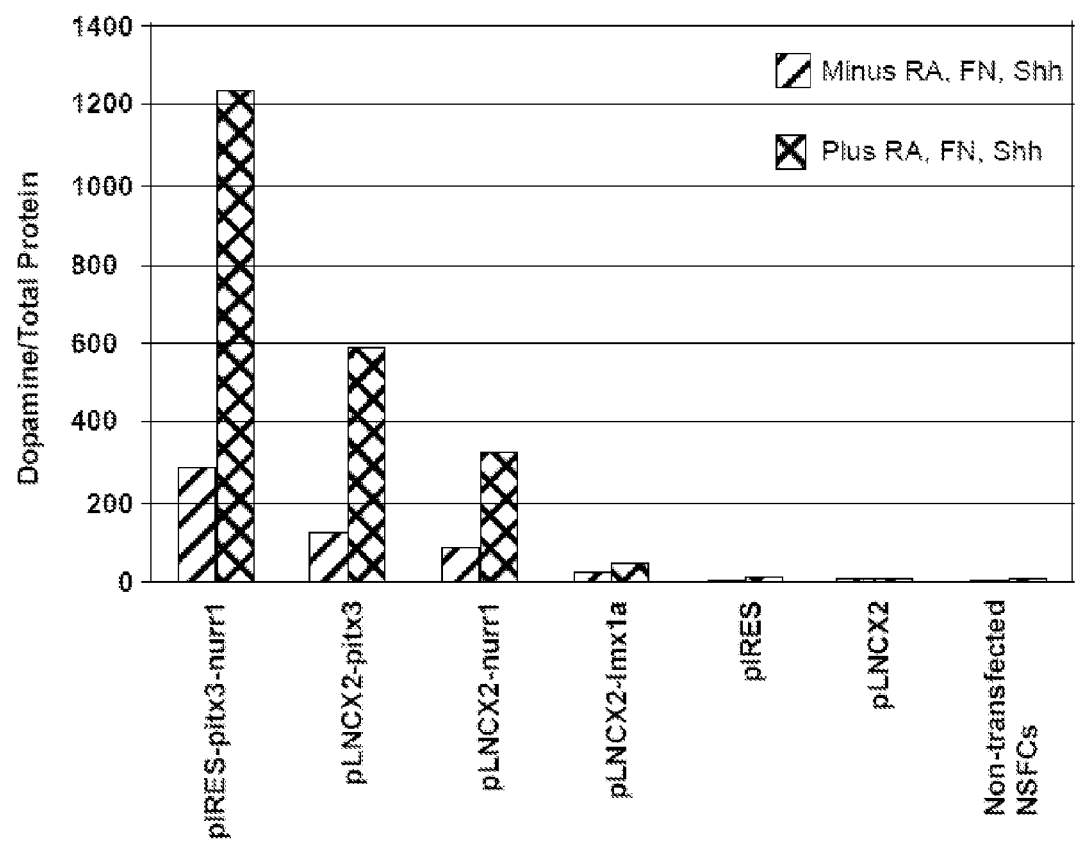

After removal from the cryostorage, dopamine production was detected in the NSFC lines which were stably transfected with concerned genes, while the cells transfected with control vectors and the non-transfected NSFCs did not produce dopamine. The dopamine level of each sample was then divided by the concentration of protein in each specific NSFC line to calculate the efficiency of dopamine production. Among all the 4 transfected lines, NSFCs transfected with pIRES-pitx3-nurr1 exhibited the most efficient dopamine formation (see FIG. 4A). The spent medium was collected 4 days after culturing the lineage restricted NSFCs. This medium was then concentrated to 1/50 volume respectively, and dopamine E.I.A. was applied to detect the dopamine release (extracellular levels). Data were calculated in the same manner as the intracellular dopamine analysis. Lower levels of dopamine were detected in the concentrated media compared to the corresponding analysis of the cell lysis. The highest level of dopamine release was detected from pIRES-pitx3-nurr1 transfected NSFCs compared to the other restricted cell lines (see FIG. 4B).

Example 4

Figure 5:
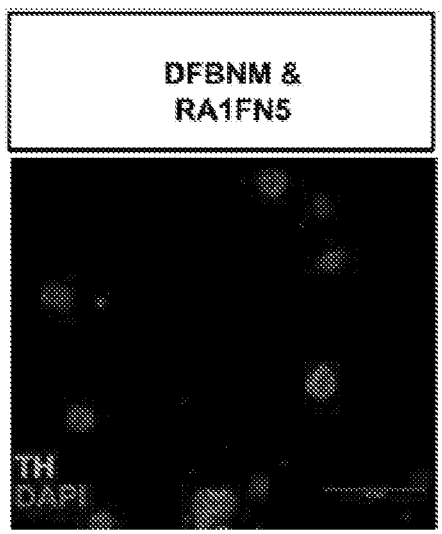
FIGS. 5A-5C depict immunocytochemistry of NSFCs treated in DMEM/F12 supplemented with 1% B27 and 0.5% $N_2$ and 100 µg/ml gentamycin (DFBNM) supplemented with 1 µM retinoic acid and 5 µM forskolin (RA1FN5) with different sources of Shh for 3 days. All cells were also stained with DAPI to show nuclei.
Figure 5:
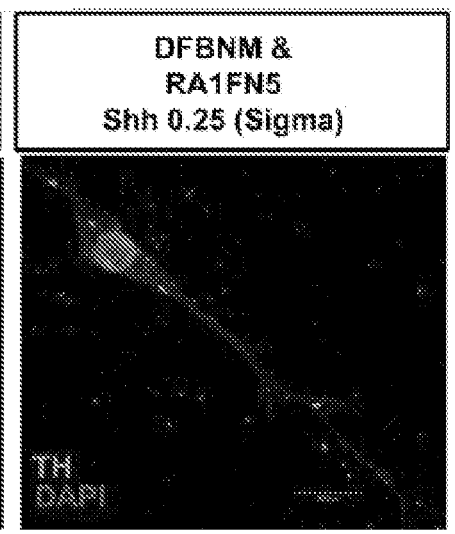
Figure 5:
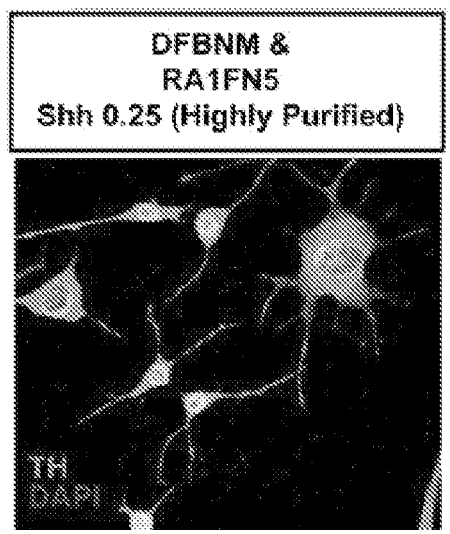

The Effect of Morphogens on Tyrosine Hydroxylase Expression and Dopamine Formation and Release NSFCs were cultured in DFBNM along with RA (1 µM), FN (5 µM), and one of two different sources (purities) of Shh for 1-7 days. TH expression was greater in the cells that were treated with highly purified Shh than the commercial product obtained from SIGMA when both were applied for same period of time. Both treatments resulted in greater expression than in those cultured solely in DFBNM. These studies suggest that Shh increases the expression of TH and that the purity (quantity) of Shh is an important determinant of TH expression (see FIG. 5).

Figure 6:
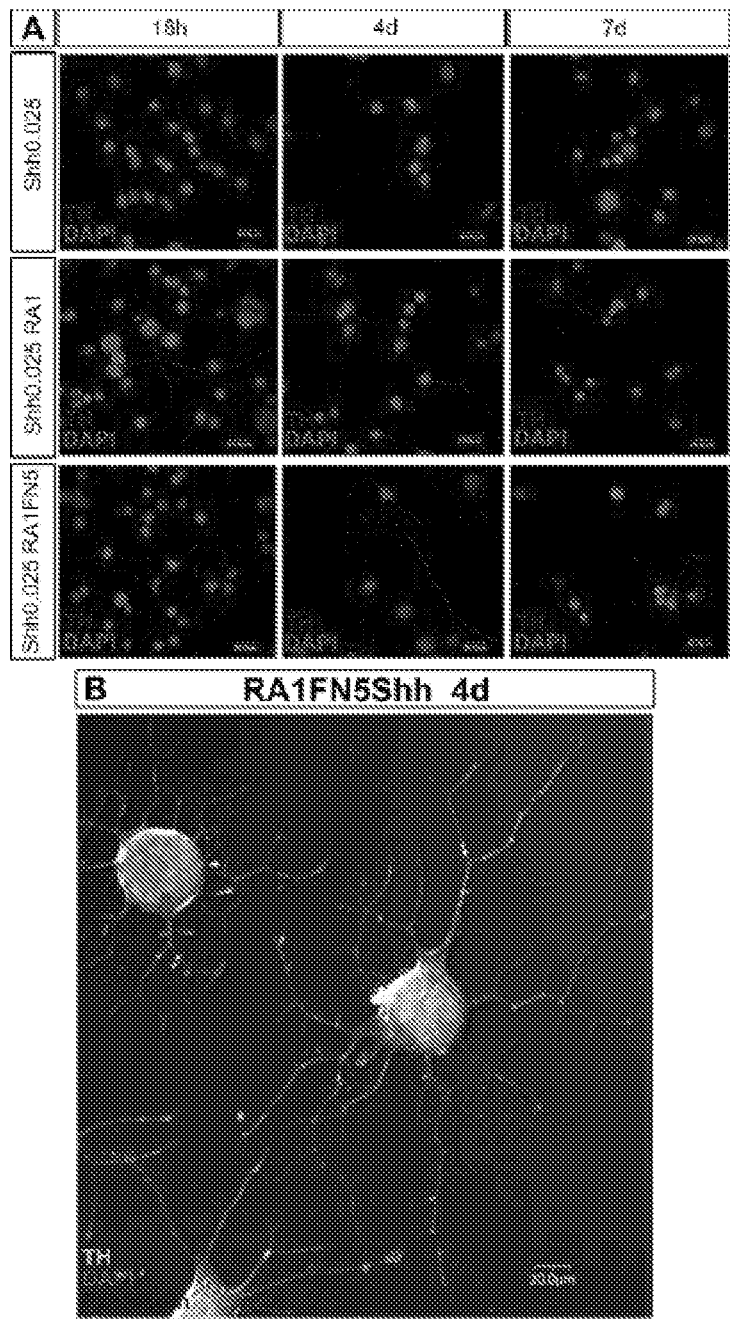
FIGS. 6A and 6B depict the results of immunocytochemistry of NSFCs cultured in DFBNM supplemented with 0.025 mg/ml of Shh (highly purified), in the presence or absence of RA (1 µM) and FN (5 µm) for the number of days indicated. All cells were also stained with DAPI to show nuclei.
Figure 7:
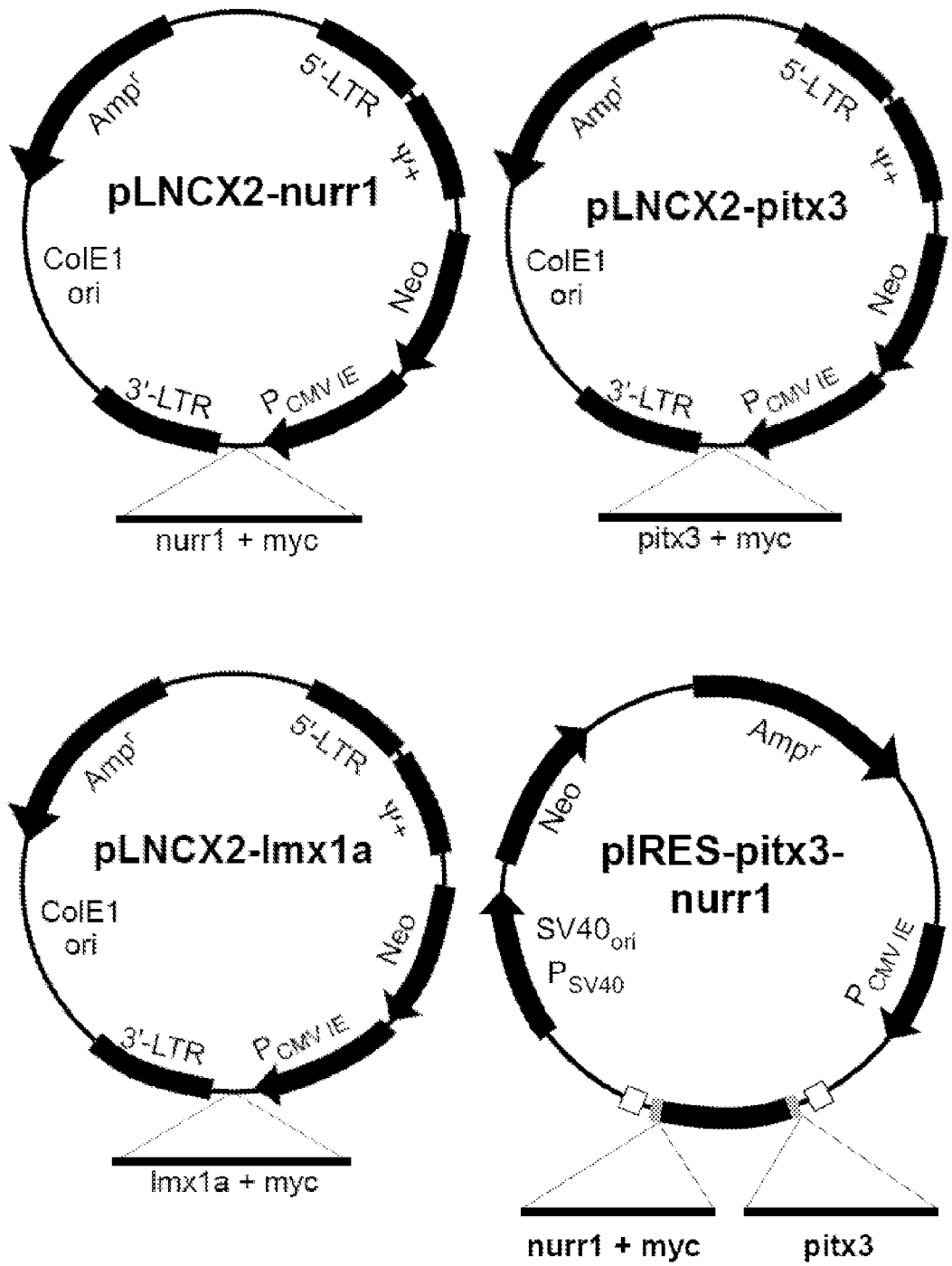
FIG. 7 depicts the structures of expression plasmids pLNCX2-nurr1, pLNCX2-pitx3, pLNCX2-Imx1a, and pIRES-pitx3-nurr1.

NSFCs treated with RA1FN5 and highly purified Shh expressed seemingly intense TH reactivity (see FIG. 5C compared to control in FIG. 5A or Sigma Shh in FIG. 5B). Therefore, the concentration of Shh was reduced to determine the lowest concentration of Shh that could drive the NSFCs towards dopaminergic neurons. In contrast to the response when a high level of Shh was applied, the reduction of the Shh to 0.025 mg/ml applied with RA (1 µM) & FN (5 µM) did not produce an immediate response. The NSFCs became TH-positive only after 18 hours of treatment with highly purified Shh; however, they were healthy and maintained TH expression for longer periods. The application of RA and FN promoted an even greater expression of TH (see FIG. 6A). Therefore, the optimal condition for lineage restricting the NSFCs to dopaminergic neurons was determined to be DFBNM supplemented with RA1FN5Shh0.025 (see FIG. 6B).

Stably transfected NSFCs were treated with a cocktail of RA1/FN5/Shh0.025 to determine if combination of genetic modification and morphogenic treatment would increase intracellular and intercellular dopamine levels. Spent medium was collected 4 days after morphogenic treatment and concentrated to a 1/50 volume. The treated lineage restricted NSFCs were also collected. Dopamine E.I.A. was applied to both cell lysis sample and concentrated medium. Dopamine formation efficiency was calculated as previously described. NSFCs transfected with pIRES-pitx3-nurr1 were the most efficient population with respect to dopamine formation and release after morphogenic treatment (see FIG. 4). Compared to intracellular and intercellular dopamine levels in the lineage restricted NSFCs in the absence of morphogens, dopaminergic expression was greatly enhanced in the stably transfected NSFCs in the presence of the combination of Shh, RA, and FN (see FIG. 4). These studies suggest that morphogenic treatment plays an important role in dopamine formation and release in the lineage restricted NSFCs.

Example 5

Behavioral Studies in Rats After 6-OHDA Lesioning with and without Transplantation of NSFCs 6-hydroxydopamine (6-OHDA) is a neurotoxin that has been used to develop certain in vivo animal models of Parkinson's disease (see e.g., Deumens et al., 2002; Iancu et al., 2005; Metz et al., 2005). Generally, 6-OHDA is introduced into one or more regions of the brains of rats, and after sufficient time has passed for the toxin to damage neurons in the vicinity of the administration site, one or more behavioral tests are conducted to determine what effect, if any, the drug had on the animals. In those instances where some form of therapy has been included to counteract the effects of the toxin, comparisons to animals that did not receive the therapy can be made to assess the efficacy of the therapy.

To that end, a series of behavioral tests were designed in order to assess the ability of transplanted NSFCs to mitigate damage produced in rat brain by 6-OHDA lesions.

In the first series of behavioral tests, a drug-induced rotation test was performed. Rats were lesioned with 6-OHDA as described above, and three weeks after the toxin was administered, animals were tested by amphetamine-induced rotational behavior analysis (Anderson & Caldwell, 2007). Rats were injected with an amphetamine (3.0 mg/ml; Catalogue No. A5880, Sigma-Aldrich Chemical Co., St. Louis, Mo., United States of America), dose at 3.0 mg/kg (0.1 ml/100 g rat; i.p.). The number of turns were counted for 90 minutes (separately record every 15 minutes) after 15 minutes drug injection. The results are summarized in Table 4.

For the engrafted animals, 25,000 cells isolated, grown, and transfected with pIRES-pitx3-nurr1 as described herein were injected into the desired site per animal. The cells were isolated from a female donor (age 41). Cells were frozen in liquid nitrogen for at least three months after transfection. Cells were thawed and taken through several passages to ensure that no DMSO protectant was present before being taken for engraftment. Cells were also initially passaged in 10% serum and than taken through serial reduction to reduce the serum to less than 0.5% before engraftment.

Figure 9:
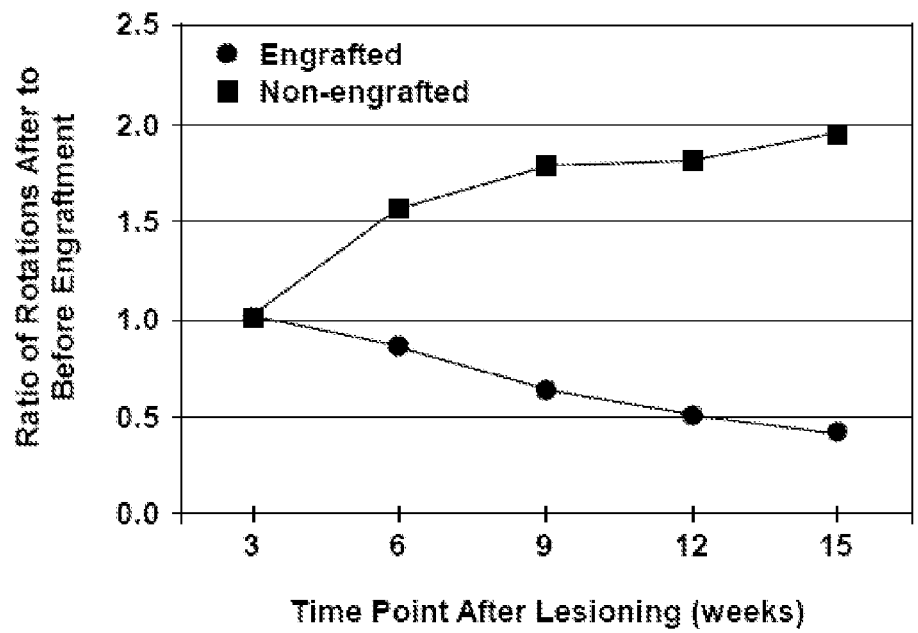
FIGS. 9A-9F summarize the results of engraftment experiments in which cells transfected with pIRES-pitx3-nurr1 were engrafted into a 6-ODHA-induced PD rat models.
Figure 9:
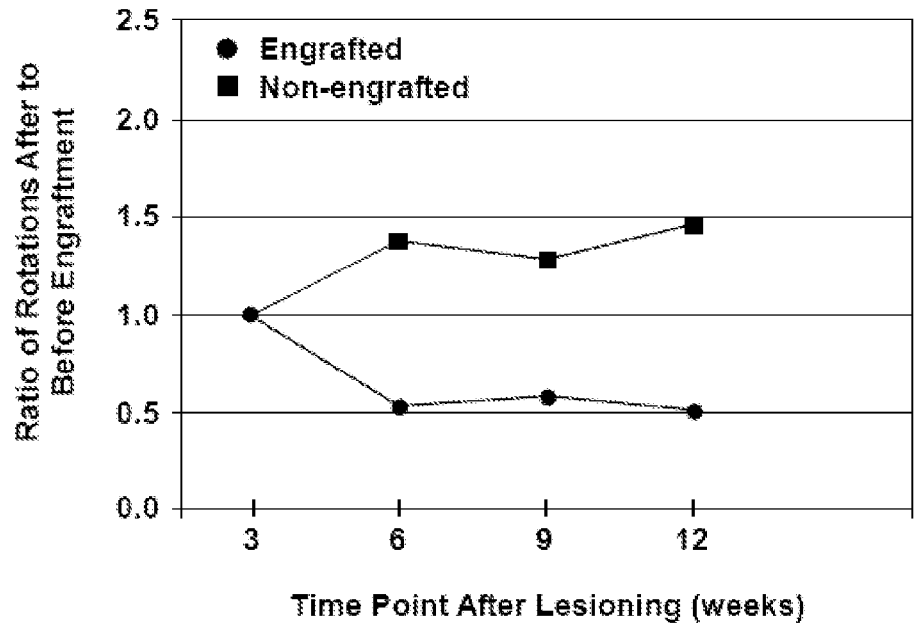
Figure 9:
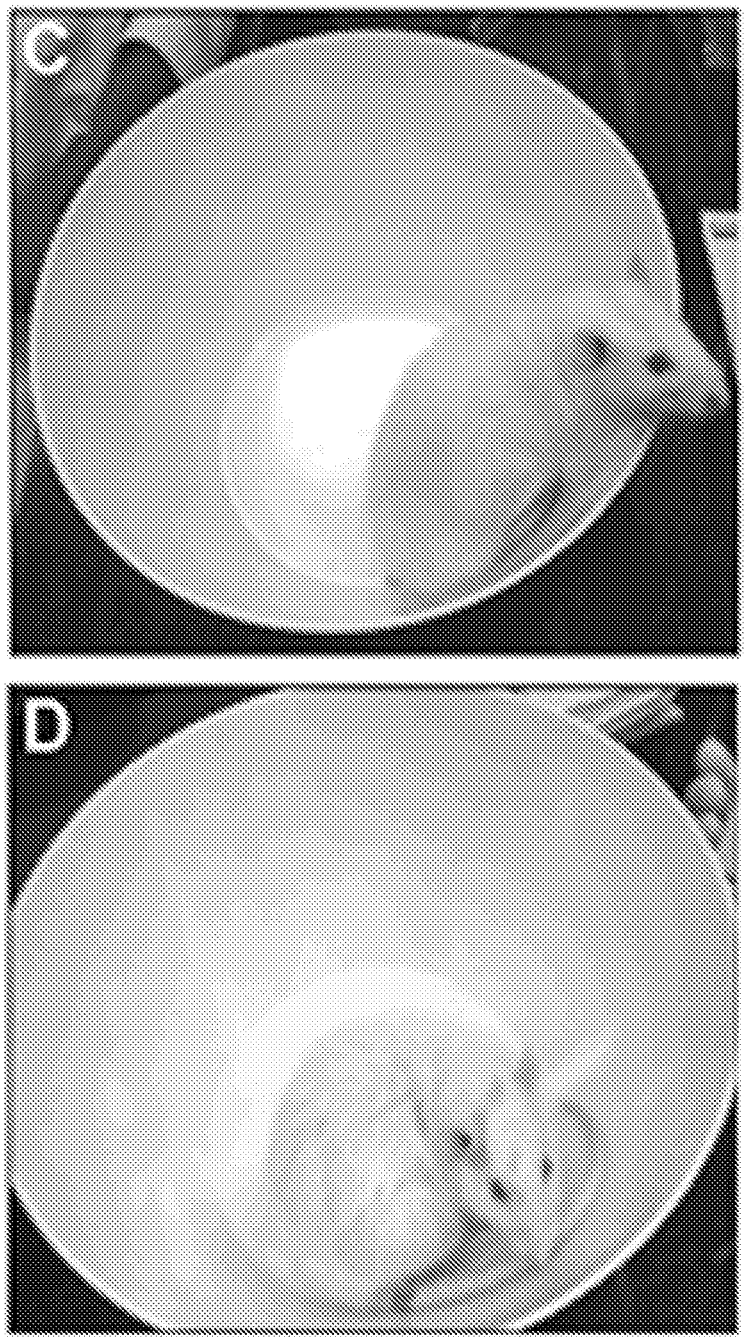
Figure 9:
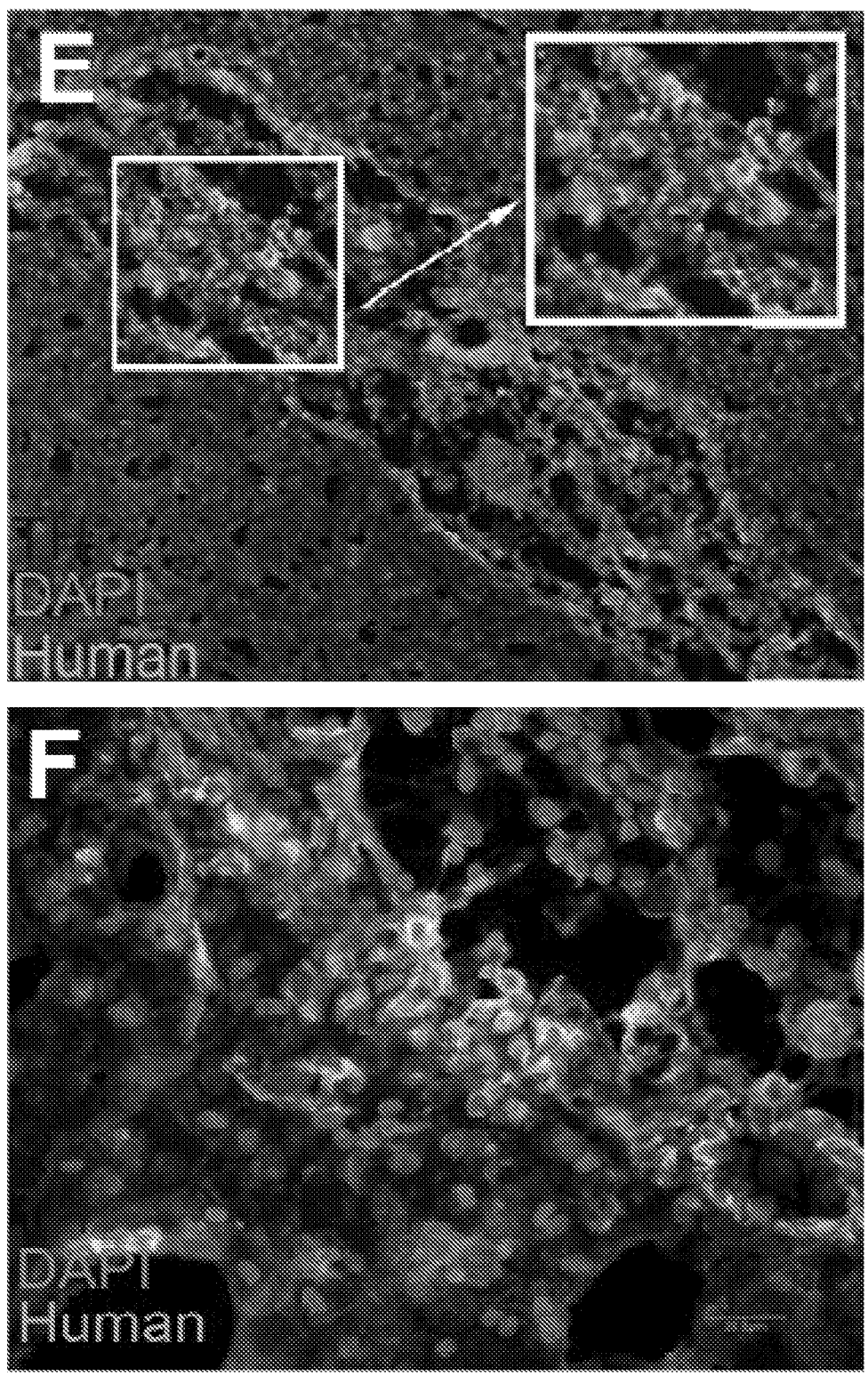

Six weeks after engraftment and nine weeks after lesioning, over 30% of the animals engrafted in either the Median Forebrain Bundle (MFB) or the striatum exhibited improved behavioral recovery in a rotation test compared to motor deficits observed in medium only treated controls. The engrafted population remained intact and TH-positive for a minimum of three months in vivo. The results are depicted in FIG. 9.

TABLE 4

Drug-induced Rotations of 6-OHDA Lesioned Rats

| | | | Time After Injection of Cells | | |
| --- | --- | --- | --- | --- | --- |
| Model | Group | 0 Weeks (Baseline) | 3 Weeks | 6 Weeks | 10 Weeks |
| MFB | Control (n = 8) | 843 ± 350 | 1099 ± 203 | 1217 ± 371 | 1300 ± 230 |
| | Cells (n = 13) | 906 ± 374 | 1053 ± 434 | 1079 ± 467 | 1068 ± 386 |
| | Non-Improved (n = 9) | 896 ± 410 | 1195 ± 386 | 1305 ± 329 | 1140 ± 340 |
| | Improved (n = 4; 30.8%) | 926 ± 332 | 736 ± 403 | 572 ± 298 | 655 ± 78 |
| Striatum | Control (n = 7) | 881 ± 454 | 1259 ± 376 | 1308 ± 388 | 1238 ± 334 |
| | Cells (n = 13) | 938 ± 398 | 1122 ± 284 | 1157 ± 453 | 1120 ± 487 |
| | Non-Improved (n = 9) | 989 ± 383 | 1207 ± 267 | 1305 ± 351 | 1385 ± 313 |
| | Improved (n = 4; 30.8%) | 821 ± 464 | 932 ± 250 | 723 ± 361 | 530 ± 119 |

6-OHDA lesioned rats are also tested in additional behavioral tests. One such test is a Corners Test (Miljan et al., 2009), in which rats are placed in a right-angle corner of a caging box with the forelimbs raised off the floor of the box. The direction that the rat turns to get out of the corner is recorded, and the test is repeated eight times for each rat. Normal rats (i.e., no lesion and no cell transplantation) show no significant preference between left and right turns.

A third behavioral test employed is a Limb-use Asymmetry (Cylinder) test. In this test, rats are placed in a clear glass cylinder (e.g., a 30 cm tall by 22 cm diameter cylinder). The number of wall contacts made by the forelimbs are recorded (left, right or both) for 5 minutes or for 5 times rear. Normal rats symmetrically use left and right forelimbs.

A fourth test is a sideway adjusting steps test (Olsson et al., 1995). Rats are held by the experimenter with one hand fixing the hind limbs and the other hand fixing one forelimb. The unfixed paw touches the slightly rough table surface and is moved slowly sideways (0.9 m for 5 seconds). The number of adjusting steps in the forehand direction is counted in both forelimbs. The test is repeated twice.

6-OHDA lesioned rats that receive transplanted NSFCs perform better in one or more of these tests then 6-OHDA lesioned rats that do not receive transplanted NSFCs.

Example 6

Expression of Neurotrophins in Transfected NSFCs

Figure 8:
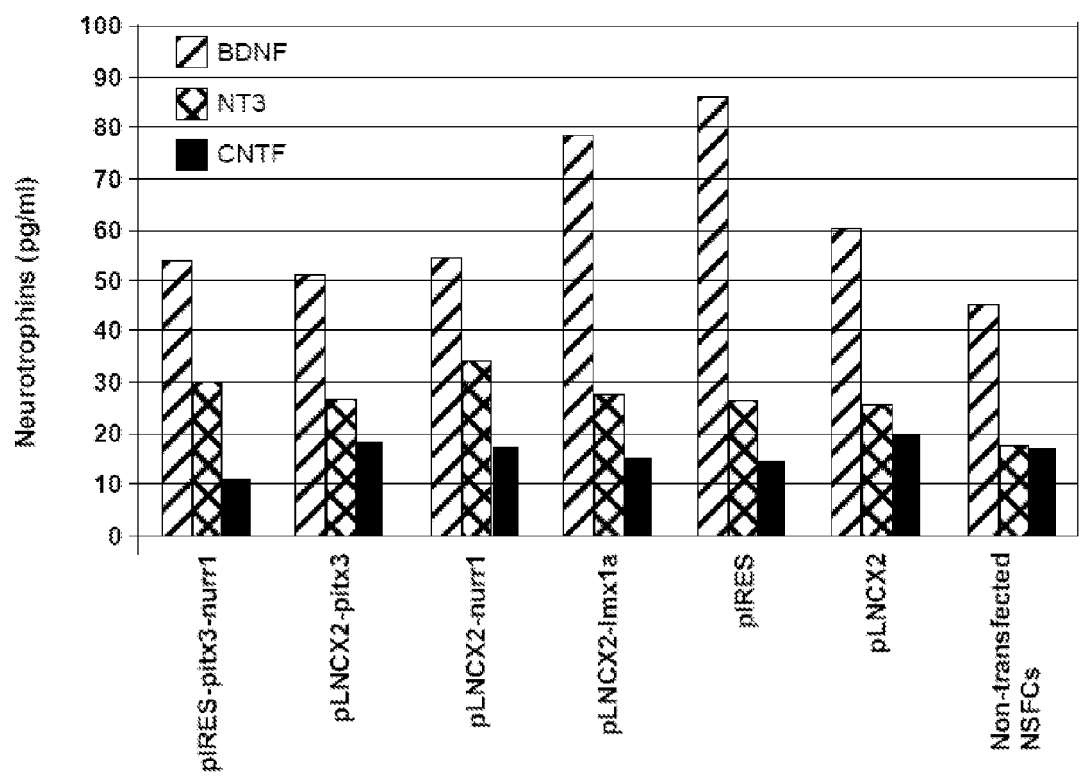
FIG. 8 is a bar graph showing neurotrophin levels in NSFCs (pg/ml) that had been transfected with various expression plasmids as compared to control and non-transfected NSFCs.

Expression of the neurotrophins BDNF, NT3, and CNTF were detected in non-transfected NSFCs. The transfected lines described hereinabove were examined to determine if lineage restriction to DA neurons alters the synthesis of these neurotrophins. As shown in FIG. 8, no significant differences in intracellular neurotrophin levels were observed between transfected and non-transfected NSFCs, indicating that transfection did not alter neurotrophin synthesis.

Discussion of the Examples

Adult human olfactory epithelium contains a population of progenitors which replace damaged or lost olfactory components throughout life, and it is highly likely that other animals (e.g., mammals) have a similar cell population. Methods to isolate and expand these epithelial-derived progenitors have been developed. When cultured in vitro, these progenitors produce neurosphere-forming cells (NSFCs) that have the potential to differentiate along several neural lineages in response to morphogenic signals.

Disclosed herein are studies aimed to optimize conditions for differentiation of these cells into dopaminergic neurons and to determine if these restricted cells can be used for cell therapy in an in vivo model of neurological disease (e.g., Parkinson's disease). The NSFCs were cultured in defined medium and treated with Sonic hedgehog (Shh), an upstream regulatory factor for dopaminergic neuron formation, in the presence or absence of agents known to act or suspected of acting as growth promoters during CNS neurogenesis: retinoic acid (RA) and/or forskolin (FN). Transcription factors, nurr1, pitx3, and lmx1a, which promote dopaminergic neuronal development in embryonic mice and/or chicken, were employed to modulate the NSFC lineage restriction.

Four expression vectors, pIRES-pitx3-nurr1, pLNCX2-pitx3, pLNCX2-nurr1 and pLNCX2-lmx1a were transfected into the NSFCs. G418 was applied to select stably transfected populations. Expression of the transcription factors and of the dopamine precursor tyrosine hydroxylase (TH) was detected in the transfected cell lines even after a 4 month selection period. The dopamine enzyme immunoassay (EIA) was utilized to detect dopamine production by each of the lines. These results suggest that transfected olfactory epithelial-derived progenitors can be restricted towards a dopaminergic lineage. The effects of genetic modification combined with exposure to Shh, RA and FN lead to further enhanced stable long term dopaminergic expression. Under these conditions, dopamine was detected intracellularly as well as in the concentrated spent medium following culture with the specific cell lines, indicating that the progenitors produced and released dopamine.

Parkinson's disease (PD), which is characterized by an extensive loss of dopaminergic (DA) neurons in a region of the midbrain called the substantia nigra (SN), remains one of the leading causes of chronic neurological disabilities. Recent efforts to treat PD have begun to consider cell replacement therapy. Initially, neural transplantation of fetal ventral mesencephalic (VM) dopaminergic neurons was employed, producing a positive outcome that was accompanied with dyskinesia in some patients. The search for a more ideal source of dopaminergic neurons is ongoing.

Stem cells with their unlimited capacity for self-renewal and ability to mature into a variety of cell types offer potential for cell replacement therapy. The olfactory epithelium is a source of neural progenitors that can be harvested endoscopically from a PD patient without damaging invasive surgery, and can therefore be used to provide autologous progenitors for transplantation. An autologous source provides total histocompatibility and avoids the need for immunosuppression.

Thus, the use of olfactory epithelial-derived progenitors including, but not limited to human and/or adult human olfactory epithelial-derived progenitors as a possible cell therapy for PD has several unique advantages: these cells can be harvested without highly invasive surgery, they provide an autologous population which would not require immunosuppressive agents; they eliminate the search and time required to find available histocompatible tissue, and they avoid the ethical concerns associated with human embryonic tissues. The results disclosed herein indicated that the expression of specific genes and morphogenic treatment can significantly enhance the lineage restriction of human adult olfactory-derived progenitors toward dopaminergic neurons.

Also disclosed herein is the discovery that overexpression of pitx3 or nurr1 promoted the expression of DA neuron maker TH in vitro. NSFC lines that were stably transfected with pitx3 or nurr1 remained healthy and TH-positive following 6 months cryostorage in liquid Nitrogen.

Furthermore, the direct detection of dopamine production was also evaluated. Lysates of pitx3- or nurr1-transfected NSFCs were dopaminergic as determined by dopamine EIA analysis. While it is not desired to be bound by any particular theory of operation, these results indicated that the transcription factors, pitx3 and nurr1 can participate in dopamine production in adult human olfactory epithelial-derived progenitors, potentially by collaborating to induce a higher efficiency of dopamine production in midbrain DA neuron maturation.

The studies disclosed herein demonstrated that the simultaneous transfection of pitx3 and nurr1 into the NSFCs produced higher levels of TH expression and dopamine production than transfection of either of these genes alone. The effect of transfection on the level of the precursor (TH) and final intracellular and extracellular levels of dopamine was evaluated to confirm and compare the efficiency of the different transfected NSFC lines.

As disclosed herein, pitx3 and nurr1 cooperatively induced the maturation of DA neurons. This demonstrated the feasibility of genetic modification of adult human olfactory epithelial-derived progenitors to promote the generation of DA neurons and supported the notion that co-expression of pitx3 and nurr1 can enhance the lineage restriction of human progenitors toward dopaminergic neurons, which can thereafter be employed in cell-replacement paradigms for the treatment of PD, among other applications.

Treatment with morphogens enhances intracellular and extracellular dopamine levels. As disclosed herein, a combination of highly purified Shh, RA, and FN was applied to the lineage restricted NSFCs. The intracellular level of dopamine was significantly increased by this treatment. Furthermore, following a 4 day treatment of RA1FN5Shh, the dopamine levels in the spent conditioned medium was significantly enhanced, indicating that the morphogens promoted the release of dopamine, which is of interest for transplantation studies with lineage restricted NSFCs into a PD model. Among all 4 lineage restricted NSFC lines, those cells transfected with pIRES-pitx3-nurr1 produced and released the highest levels of dopamine in the presence of Shh, RA and FN. This result is consistent with the analysis of the lineage restricted cells in the absence of treatment with the morphogens.

These data further support the conclusion that NSFCs transfected with pIRES-pitx3-nurr1 are the most efficient line in dopamine production studies to date, and therefore are likely candidates for engraftment into an animal model of PD. Local distribution of the morphogens Shh, RA, and FN in situ should influence the engrafted NSFCs and can support their differentiation, survival and dopamine production following transplantation. The higher level of dopamine release following Shh, RA, and FN treatment suggests a role in cell therapy for PD in that it demonstrates the potential ability of NSFCs to respond to site directed factors. The results of the present studies utilizing transfection and morphogens thus support the potential of neural progenitors as a cell therapy in the treatment of PD, among other disorders.

Improvement in a Parkinson's Animal Model. As disclosed herein, animals engrafted with NSFCs transfected with pIRES-pitx3-nurr1 showed improvement in a 6-OHDA/amphetamine-induced rotational behavior model, which has been employed as an animal model of PD. Engraftment of transfected NSFCs resulted in more than 30% of the animals engrafted in either the Median Forebrain Bundle (MFB) or in the striatum showing improvement in this PD model, supporting engraftment of NSFCs into PD subjects to ameliorate their symptoms.

Long term survival of engrafted NSFCs. Animals engrafted with NSFCs were also examined for long term survival of the engrafted NSFCs. As disclosed herein, engrafted NSFCs remained intact and TH-positive for a minimum of three months in vivo. This indicates that engrafted NSFCs can survive long term post engraftment, which could be beneficial in treating subjects with neurological disorders as long term NSFC engraftment would reduce or eliminate the need to perform multiple engraftments.

Provided herein are NSFC lines that can have therapeutic utility in strategies for the treatment of patients with neurological disorders including, but not limited to PD. The in vivo viability and stability are of interest, especially considering the likelihood that with time the engrafted population can die and require replacement. Therefore, as disclosed herein, experiments were undertaken to determine the stability and viability of frozen stocks of transfected cells. NSFCs survived under the pressure of selection after removal from cryostorage and retained their ability to express TH, as well as produce and release dopamine, which highlights the unique potential of these progenitors to serve as an autologous cell source for cell-based strategies for the long term treatment of Parkinson's disease and other neurological disorders.

REFERENCES

The references listed below as well as all references cited in the specification, including patents, patent applications, journal articles, and all database entries (e.g., GENBANK® Accession Nos., including any annotations presented in the GENBANK® database that are associated with the disclosed sequences), are incorporated herein by reference to the extent that they supplement, explain, provide a background for, or teach methodology, techniques, and/or compositions employed herein.

Anderson & Caldwell (2007) Neurobiol Dis 27:133-140.
Ausubel et al. (2002) *Short Protocols in Molecular Biology*, Fifth ed. Wiley, New York, N.Y., United States of America.
Ausubel et al. (2003) *Current Protocols in Molecular Biology*, John Wylie & Sons, Inc., New York, N.Y., United States of America.
Borlongan (2000) 9:2319-2330.
Brederlau et al. (2006) *Stem Cells* 24:1433-1440.
Carter (1986) *Biochem J* 237:1-7.
Daadi (2002) *Methods Mol Biol* 198:265-271.
Deumens et al. (2002) *Exp Neurol* 175:303-317.
Doss et al. (2004) *J Cell Mol Med* 8:465-473.
Dubois et al. (1990) *J Biol Chem* 265:2797-2803.
Freed et al. (2001) *N Engl J Med* 344:710-719.
Freeman et al. (1995) *Ann Neurol* 38:379-388.
Harlow & Lane (1988) *Antibodies: A Laboratory Manual*, Cold Spring Harbor Laboratory, Cold Spring Harbor, N.Y.
Harlow & Lane (1999) *Using Antibodies: A Laboratory Manual*, Cold Spring Harbor Laboratory, Cold Spring Harbor, N.Y.
Hornykiewicz (1973a) *Br Med Bull* 29:172-178.
Hornykiewicz (1973b) *Fed Proc* 32:183-190.
Iancu et al. (2005) *Behav Brain Res* 162:1-10.
Lang & Lozano (1998) *N Engl J Med* 339:1044-1053.
Li et al. (1997) *Science* 277:2000-2002.
Lindvall et al. (1988) *Lancet* 2:1483-1484.
Lindvall et al. (1992) *Ann Neurol* 31:155-165.
Lindvall et al. (2004) *Nat Med* 10 Suppl:S42-50.
Madrazo et al. (1988) *N Engl J Med* 318:51.
Marshall et al. (2006) *Histol Histopathol* 21:633-643.
Mendez et al. (2005) *Brain* 128:1498-1510.
Metz et al. (2005) *Eur J Neurol* 22:735-744.
Miljan et al. (2009) *Stem Cells Devel* 18: 307-320.
Olanow et al. (2003) *Ann Neurol* 54:403-414.
Olsson et al. (1995) *J Neurosci* 15:3863-3875.
Othman et al. (2005a) *Biotech Histochem* 80:177-188.
Othman et al. (2005b) *Biotech Histochem* 80:189-200.
Paxinos & Watson (1998) *The Rat Brain (Fourth Edition)*, Academic Press, New York, N.Y., United States of America.
PCT International Patent Application Publication Nos. WO 2003/064601; WO 2008/027848.
Redmond et al. (2007) *Proc Natl Acad Sci USA* 104:12175-12180.
Roisen et al. (2001) *Brain Res* 890:11-22.
Sambrook & Russell (2001) *Molecular Cloning: A Laboratory Manual*, 3rd edition, Cold Spring Harbor Laboratory Press, Cold Spring Harbor, N.Y.
Schade & Hlinak (1996) *ALTEX* 13:5-9.
Snyder & Olanow (2005) *Curr Opin Neurol* 18:376-385.
Sonntag et al. (2005) *Brain Res Mol Brain Res* 134:34-51.
Stahel (2006) *Newron Pharmaceut Ann Rep* 2006.
Tian et al. (1999) *J Mol Cell Cardiol* 31:751-760.
Tijssen (ed.) (1993) *Laboratory Techniques in Biochemistry and Molecular Biology: Hybridization With Nucleic Acid Probes, Part I Theory and Nucleic Acid Preparation*, Elsevier Press, New York, N.Y., United States of America.
U.S. Pat. Nos. 5,648,235; 5,660,827; 5,733,876; 5,753,230; 5,762,918; 5,766,591; 5,776,427.
Wells et al. (1985) *Gene* 34:315-23.
Winstead et al. (2005) *Am J Rhinol* 19:83-90.
Woodlee et al., (2008) *Exp Neurol* 211:511-517.
Zhang et al. (2004) *Exp Neurol* 186:112-123.
Zhang et al. (2006) *Brain Res* 1073-1074:109-119.
Zhou et al. (1990) *Mol Cell Biol* 10:4529-4539.
Zoller & Smith (1987) *Meth Enzymol* 154:329-50.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method for producing a recombinant dopaminergic neuron, the method comprising:
   (a) providing adult human olfactory epithelial-derived stem cells;
   (b) introducing, into the adult human olfactory epithelial-derived stem cells, one or more transgenes encoding a nurr-1 polypeptide, a pitx3 polypeptide and a Imx1a polypeptide, to produce transgenic adult human olfactory epithelial-derived stem cells; and
   (c) culturing the transgenic adult human olfactory epithelial-derived stem cells to produce recombinant dopaminergic neurons, wherein the recombinant dopaminergic neurons produce increased levels of intracellular dopamine relative to the levels of intracellular dopamine produced by adult human olfactory epithelial-derived stem cells expressing the nurr-1 polypeptide, the pitx3 polypeptide or the Imx1a polypeptide.

2. The method of claim 1, wherein the adult human olfactory epithelial-derived stem cells are from a cadaver.

3. The method of claim 1, wherein the adult human olfactory epithelial-derived stem cells are from a living donor.

4. The method of claim 3, wherein the living donor is a subject having a neurological disorder.

5. The method of claim 4, wherein the neurological disorder is Parkinson's disease.

6. The method of claim 1, wherein at least one of the nurr-1 polypeptide, the pitx3 polypeptide, the Imx1a polypeptide, or the combination thereof are from a species other than human.

7. The method of claim 6, wherein the pitx3 polypeptide is a rat pitx3 polypeptide.

8. The method of claim 6, wherein the Imx1a polypeptide is a mouse Imx1a polypeptide.

9. The method of claim 6, wherein the nurr-1 polypeptide is a mouse nurr-1 polypeptide.

10. The method of claim 1, further comprising culturing the adult human olfactory epithelial-derived stem cells before, during, and/or after the introducing step in medium, the medium comprising a Sonic hedgehoge (Shh) polypeptide or a biologically active fragment thereof, retinoic acid (RA) or a biologically active fragment thereof, foskolin (FN) or a biologically active fragment thereof, to induce neuronal differentiation in the adult olfactory epithelial-derived stem cells.

11. The method of claim 1, further comprising:
    transplanting the recombinant dopaminergic neuron into the brain of a subject having a neurological disorder characterized by a loss or degeneration of dopaminergic neurons.

12. The method of claim 11, wherein the neurological disorder is Parkinson's disease.

* * * * *

UNITED STATES PATENT AND TRADEMARK OFFICE
CERTIFICATE OF CORRECTION

Page 1 of 1

PATENT NO. : 9,090,874 B2
APPLICATION NO. : 13/127142
DATED : July 28, 2015
INVENTOR(S) : Fred J. Roisen et al.

It is certified that error appears in the above-identified patent and that said Letters Patent is hereby corrected as shown below:

Title Page

First Page, Column 2, Line 12 (Other Publications), delete "Neuopathology" and insert -- Neuropathology --, therefor.

First Page, Column 2, Line 12 (Abstract), delete "ancllor" and insert -- and/or --, therefor.

Claims

Column 58, Line 14, in Claim 10, delete "hedgehoge" and insert -- hedgehog --, therefor.

Column 58, Line 16, In Claim 10, delete "foskolin" and insert -- forskolin --, therefor.

Signed and Sealed this
Ninth Day of February, 2016

Michelle K. Lee
*Director of the United States Patent and Trademark Office*